US010793608B2

(12) United States Patent
Wei et al.

(10) Patent No.: US 10,793,608 B2
(45) Date of Patent: Oct. 6, 2020

(54) HYPERSENSITIVE RESPONSE ELICITOR-DERIVED PEPTIDES AND USE THEREOF

(71) Applicant: Plant Health Care, Inc., Raleigh, NC (US)

(72) Inventors: Zhongmin Wei, Kirkland, WA (US); Gregory A. Zornetzer, Seattle, WA (US)

(73) Assignee: PLANT HEALTH CARE, INC., Raleigh, NC (US)

( * ) Notice: Subject to any disclaimer, the term of this patent is extended or adjusted under 35 U.S.C. 154(b) by 26 days.

(21) Appl. No.: 15/476,082

(22) Filed: Mar. 31, 2017

(65) Prior Publication Data
US 2017/0291924 A1   Oct. 12, 2017

Related U.S. Application Data

(60) Provisional application No. 62/319,138, filed on Apr. 6, 2016.

(51) Int. Cl.
| | | |
|---|---|---|
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 14/195* | (2006.01) | |
| *A01N 37/46* | (2006.01) | |
| *C12N 15/82* | (2006.01) | |
| *A01N 63/10* | (2020.01) | |

(52) U.S. Cl.
CPC ............ *C07K 14/195* (2013.01); *A01N 37/46* (2013.01); *A01N 63/10* (2020.01); *C12N 15/8273* (2013.01); *C12N 15/8279* (2013.01); *C12N 15/8283* (2013.01); *C12N 15/8285* (2013.01); *C07K 2319/00* (2013.01); *C07K 2319/20* (2013.01); *C07K 2319/50* (2013.01); *Y02A 40/164* (2018.01)

(58) Field of Classification Search
None
See application file for complete search history.

(56) References Cited

U.S. PATENT DOCUMENTS

| | | | |
|---|---|---|---|
| 5,473,039 A | 12/1995 | Dyer et al. | |
| 5,776,889 A | 7/1998 | Wei et al. | |
| 5,859,339 A | 1/1999 | Ronald et al. | |
| 5,977,060 A | 11/1999 | Zitter et al. | |
| 6,235,974 B1 | 5/2001 | Qiu et al. | |
| 6,277,814 B1 | 8/2001 | Qiu et al. | |
| 6,310,176 B1 | 10/2001 | Barra et al. | |
| 6,563,020 B1 | 5/2003 | Simmons et al. | |
| 6,624,139 B1 | 9/2003 | Wei et al. | |
| 6,858,707 B1 | 2/2005 | Wei et al. | |
| 6,960,705 B2 | 11/2005 | Wei et al. | |
| 7,132,393 B2 | 11/2006 | Summerton | |
| 7,132,525 B2 | 11/2006 | Laby et al. | |
| 8,440,881 B2 | 5/2013 | Park et al. | |
| 8,686,224 B2 | 4/2014 | Ryan et al. | |
| 9,109,039 B2 | 8/2015 | Ryan et al. | |
| 2002/0007501 A1 | 1/2002 | Song et al. | |
| 2002/0019337 A1 | 2/2002 | Wei et al. | |
| 2002/0062500 A1 | 2/2002 | Fan et al. | |
| 2002/0059658 A1 | 5/2002 | Wei et al. | |
| 2003/0104979 A1 | 6/2003 | Wei et al. | |
| 2004/0016029 A1 | 1/2004 | Wei | |
| 2004/0073977 A1 | 4/2004 | Misra et al. | |
| 2005/0250699 A1 | 10/2005 | Kristensen et al. | |
| 2006/0248617 A1 | 11/2006 | Imanaka et al. | |
| 2009/0118134 A1 | 5/2009 | Vrijloeb et al. | |

(Continued)

FOREIGN PATENT DOCUMENTS

| | | |
|---|---|---|
| CN | 1793172 | 6/2006 |
| CN | 101284876 | 10/2008 |

(Continued)

OTHER PUBLICATIONS

Niv et al., "New Lytic Peptides Based on the D, L-Amphipathic Helix Motif Preferentially Kill Tumor Cells Compared to Normal Cells," Biochemistry, American Chemical Society 42(31):9346-9354 (2003).

(Continued)

*Primary Examiner* — Larry D Riggs, II
*Assistant Examiner* — Zachary J Miknis
(74) *Attorney, Agent, or Firm* — Troutman Pepper Hamilton Sanders LLP (Rochester)

(57) ABSTRACT

Disclosed are hypersensitive-response eliciting peptides and non-hypersensitive response eliciting peptides that induce active plant responses, and that exhibit improved solubility, stability, resistance to chemical degradation, or a combination of these properties. Use of these peptides or fusion polypeptides, or DNA constructs encoding the same, for modulating plant biochemical signaling, imparting disease resistance to plants, enhancing plant growth, imparting tolerance to biotic stress, imparting tolerance and resistance to abiotic stress, imparting desiccation resistance to cuttings removed from ornamental plants, imparting post-harvest disease or post-harvest desiccation resistance to a fruit or vegetable, or enhancing the longevity of fruit or vegetable ripeness are also disclosed.

43 Claims, 3 Drawing Sheets

Specification includes a Sequence Listing.

(56) References Cited

U.S. PATENT DOCUMENTS

| | | |
|---|---|---|
| 2009/0300802 A1 | 12/2009 | Ryan et al. |
| 2010/0043095 A1 | 2/2010 | Wei |
| 2010/0064386 A1 | 3/2010 | Park et al. |
| 2011/0191896 A1 | 8/2011 | Pitkin et al. |
| 2011/0233469 A1 | 9/2011 | Petersen |
| 2012/0265513 A1 | 10/2012 | Fang et al. |
| 2013/0116119 A1 | 5/2013 | Rees et al. |
| 2013/0125258 A1 | 5/2013 | Emmanuel et al. |
| 2013/0150288 A1 | 6/2013 | Dobson |
| 2013/0172185 A1 | 7/2013 | Wei et al. |
| 2013/0274104 A1 | 10/2013 | Reddig et al. |
| 2013/0298287 A1 | 11/2013 | Park et al. |
| 2014/0090103 A1 | 3/2014 | Pitkin et al. |
| 2014/0227767 A2 | 8/2014 | Yeaman et al. |
| 2015/0218099 A1 | 8/2015 | Mann |
| 2016/0095314 A1 | 4/2016 | Wei et al. |
| 2016/0095315 A1 | 4/2016 | Wei et al. |
| 2016/0297853 A1 | 4/2016 | Wei et al. |
| 2016/0145310 A1 | 5/2016 | Wei et al. |
| 2016/0353735 A1 | 12/2016 | Wei et al. |
| 2016/0353736 A1 | 12/2016 | Wei et al. |

FOREIGN PATENT DOCUMENTS

| | | | |
|---|---|---|---|
| CN | 101892244 | 11/2010 | |
| CN | 103103202 | 5/2013 | |
| CN | 1454989 | 11/2013 | |
| CN | 106831964 | 6/2017 | |
| EP | 1 930 025 A1 | 6/2008 | |
| EP | 1 997 502 A1 | 12/2008 | |
| EP | 2168592 | 3/2010 | |
| WO | 95/31564 | 11/1995 | |
| WO | 98/06748 | 2/1998 | |
| WO | 99/02655 | 7/1998 | |
| WO | WO-9902546 A1 * | 1/1999 | ............. C07K 14/47 |
| WO | 99/37664 | 7/1999 | |
| WO | 00/020452 A2 | 4/2000 | |
| WO | 00/28056 | 5/2000 | |
| WO | 01/055335 A2 | 8/2001 | |
| WO | 01/80639 | 11/2001 | |
| WO | 01/98501 A1 | 12/2001 | |
| WO | 2001/098501 | 12/2001 | |
| WO | 02/12293 A2 | 2/2002 | |
| WO | 2002/022821 | 3/2002 | |
| WO | 2005/017158 | 2/2005 | |
| WO | 2006/077601 A2 | 7/2006 | |
| WO | 2008/104598 A2 | 9/2008 | |
| WO | 2010/019442 | 2/2010 | |
| WO | 2010/042654 A2 | 4/2010 | |
| WO | 2013/102189 | 7/2013 | |

OTHER PUBLICATIONS

Zeitler et al., "De-Novo Design of Antimicrobial Peptides for Plant Protection," PLOS ONE 8(8):E71687 (2013).
Jung-Gun et al., "Mutational Analysis of Xanthomonas Harpin HpaG Identifies a Key Functional Region that Elicits the Hypersensitive Response in Nonhost Plants," Journal of Bacteriology, American Society for Microbiology 186(18):6239-6247 (2004).
Choi et al., "Harpins, Multifunctional Proteins Secreted by Gram-Negative Plant-Pathogenic Bacteria," Molecular Plant-Microbe Interactions 26(10):1115-1122 (2013).
Mur et al., "The Hypersensitive Response; The Centenary is Upon Us But How Much Do We Know?," Journal of Experimental Botany 59(3):501-520 (2007).
Gentilucci et al., "Chemical Modifications Designed to Improve Peptide Stability: Incorporation of Non-Natural Amino Acids, Pseudo-Peptide Bonds, and Cyclization," Current Pharmaceutical Design 16(28):3185-3203 (2010).
Trevino et al., "Measuring and Increasing Protein Solubility," Journal of Pharmaceutical Sciences 97 (10):4155-4166 (2008).
Olsen et al., "Trypsin Cleaves Exclusively C-Terminal to Arginine and Lysine Residues," Mol. and Cell. Proteomics 3.6 3:608-614 (2004).
Kim et al., "HrpW of Erwinia Amylovora, a New Harpin that Contains a domain Homologous to Pectate Lyases of a Distinct Class," J. Bacteriol 180(19):5203-5210 (1998).
Osusky et al., "Transgenic Potatoes Expressing a Novel Cationic Peptide are Resistant to Late Blight and Pink Rot," Transgenic Research 13(2):181-190 (2004).
Yevtushenko et al., "Comparison of Pathogen-Induced Expression and Efficacy of Two Amphibian Antimicrobial Peptides, MsrA2 and Temporin A, for Engineering Wide-Spectrum Disease Resistance in Tobacco," Plant Biotechnology Journal 5(6):720-734 (2007).
Miao et al., "HpaXm from *Xanthomonas citri* Subsp. Malvacearum is a Novel Harpin With Two Heptads for Hypersensitive Response," Journal of Microbiology and Biotechnology 20(1):54-62 (2010).
Chen et al., "Identification of Specific Fragments of HpaG Xooc, a Harpin for Xanthomonas Oryzae Pv. Oryzicola, That Induce Disease Resistance and Enhance Growth in Plants," Phytopathology 98(7):781-791 (2008).
Maget-Dana et al., "Amphiphilic Peptides as Models for Protein-Membrane Interactions: Interfacial Behaviour of Sequential Lys- and Leu-based Peptides and Their Penetration into Lipid Monolayers," Supramolecular Sci. 4:365-368 (1997).
Park et al., "Helix Stability Confers Salt Resistance upon Helical Antimicrobial Peptides," J. Biol. Chem. 279:13896-13901 (2004).
Saito et al., "Synthesis of a Peptide Emulsifier with an Amphiphilic Structure," Bioscience, Biotechnology, and Biochemistry 59:388-392 (1995).
Slechtova et al., "Insight into Trypsin Miscleavage: Comparison of Kinetic Constants of Problematic Peptide Sequences," Analytical Chemistry 87:7636-7643 (2015).
International Search Report for International Application No. PCT/US17/25470 dated Jun. 27, 2017.
Van Loon et al., "Systemic Resistance Induced by Rhizosphere Bacteria," Annu. Rev. Phytopathol. 36:453-83 (1998).
Oliveira et al., "Induced Resistance During the Interaction Pathogen x Plant and the Use of Resistance Inducers," Phytochemistry Letters 15:152-158 (2016).
International Search Report and Written Opinion for PCT/US17/25470 (dated Aug. 25, 2017).
Kim et al., "Mutational Analysis of Xanthomonas Harpin HpaG Identifies a Key Functional Region That Elicits the Hypersensitive Response in Nonhost Plants," J. Bacteriol. 186(18):6239-6247 (2004).
Ji et al., "Two Coiled-Coil Regions of Xanthomonas oryzae pv. Oryzae Harpin Differ in Oligomerization and Hypersensitive Response Induction," Amino Acids 40:381-392 (2011).
Haapalainen et al., "Functional Mapping of Harpin HrpZ of Pseudomonas syringae Reveals the Sites Responsible for Protein Oligomerization, Lipid Interactions, and Plant Defence Induction," Mol. Plant Pathol. 12(2):151-66 (2011).
Lilie et al, "Polyionic and Cysteine-Containing Fusion Peptides as Versatile Protein Tags," Biol. Chem. 394(8):995-1004 (2013).
Li et al., "Complete Regression of Well-Established Tumors Using a Novel Water-Soluble Poly(L-Glutamic Acid)-Paclitaxel Conjugate," Cancer Res. 58: 2404-2409 (1998).
Arlat et al., "PopA1, a Protein Which Induces a Hypersensitivity-Like Response on Specific Petunia Genotypes, is Secreted Via the Hrp Pathway of Pseudomonas Solanacearum," The EMBO J. 13(3)543-553 (1994).
NCBI Reference No. WP_082338630 (Apr. 11, 2017).
NCBI Reference No. WP_014505138.1 (May 19, 2017).
Inoue et al., "The HrpZ and HrpA Genes are Variable, and Useful for Grouping Pseudomonas Syringae Bacteria," Journal of General Plant Pathology 72(1):26-33 (2006).
Shrestha et al., "The Hrp Gene Cluster in Erwinia Pyrifoliae and Determination of HR Active Domain in HrpNEp Protein," ISHS Acta Horticulturae 793: XI International Workshop on Fire Blight.
Lee et al., "Relationship Between Antimicrobial Activity and Amphiphilic Property of Basic Model Peptides," Biochimica Biophysica Acta (BBA)-Biomembranes 862(1):211-219 (1986).

(56) References Cited

OTHER PUBLICATIONS

Shenge et al., "Molecular Characterization of Pseudomonas Syringae pv. Tomato Isolates From Tanzania," Phytoparasitica 36(4):338-351 (2008).
CAS RN 429026-68-6 (2002).
Wang et al., "Hpal is a Type III Translocator in Xanthomonas oryzae pv. Oryzae," BMC Microbiology (18):105 (2018).
Extended Search Report European Patent Application No. 17779572.1 (dated Nov. 21, 2019).
Monaka et al., "Complete Genome Sequence of the Dehalorespiring Bacterium Desulfitobacterium Hafniense Y51 and Comparison with Dehalococcoides Ethenogenes 195", Journal of Bacteriology American Society for Microbiology 188 (6):2262-2274 (2006).
NCBI Accession No. BAE86111 Mar. 22, 2006.
Wei et al., "Harpin, Elicitor of the Hypersensitive Response Produced by the Plant Pathogen Erwinia Amylovora", Science 257:85-88 (1992).
Chen et al., "A fragment of the Xanthomonas oryzae pv. oryzicola harpin HpaGXooc reduces disease and increases yield of rice in extensive grower plantings," Phytopathology 98:792-802 (2008).
Chen et al., "Identification of specific fragments of HpaGXooc, a harpin protein from Xanthomonas oryzae pv. oryzicola, that induce disease resistance and enhance growth in plants," Phytopathology 98:781-791 (2008).

\* cited by examiner

SEQUENCE LISTING

```
<160> NUMBER OF SEQ ID NOS: 549

<210> SEQ ID NO 1
<211> LENGTH: 13
<212> TYPE: PRT
<213> ORGANISM: Artificial
<220> FEATURE:
<223> OTHER INFORMATION: Consensus peptide
<220> FEATURE:
<221> NAME/KEY: MISC_FEATURE
<222> LOCATION: (1)..(1)
<223> OTHER INFORMATION: X at position 1 is L, I, V, or F
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is optional, any amino acid
<220> FEATURE:
<221> NAME/KEY: MISC_FEATURE
<222> LOCATION: (4)..(4)
<223> OTHER INFORMATION: X at position 4 is L, I, V, or F
<220> FEATURE:
<221> NAME/KEY: MISC_FEATURE
<222> LOCATION: (5)..(5)
<223> OTHER INFORMATION: X at position 5 is L, I, V, or F
<220> FEATURE:
<221> NAME/KEY: MISC_FEATURE
<222> LOCATION: (6)..(6)
<223> OTHER INFORMATION: X at position 6 is L, I, V, or F
<220> FEATURE:
<221> NAME/KEY: MISC_FEATURE
<222> LOCATION: (7)..(7)
```

```
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is L, I, V or F
<220> FEATURE:
<221> NAME/KEY: MISC_FEATURE
<222> LOCATION: (9)..(9)
<223> OTHER INFORMATION: X at position 9 is L, I, V or F
<220> FEATURE:
<221> NAME/KEY: MISC_FEATURE
<222> LOCATION: (10)..(10)
<223> OTHER INFORMATION: X at position 10 is any amino acid
<220> FEATURE:
<221> NAME/KEY: MISC_FEATURE
<222> LOCATION: (11)..(11)
<223> OTHER INFORMATION: X at position 11 is any amino acid
<220> FEATURE:
<221> NAME/KEY: MISC_FEATURE
<222> LOCATION: (12)..(12)
<223> OTHER INFORMATION: X at position 12 is any amino acid
<220> FEATURE:
<221> NAME/KEY: MISC_FEATURE
<222> LOCATION: (13)..(13)
<223> OTHER INFORMATION: X at position 13 is L, I, V, or F

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 13
<212> TYPE: PRT
<213> ORGANISM: Artificial
<220> FEATURE:
<223> OTHER INFORMATION: P5 consensus peptide
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is optional, any amino acid
<220> FEATURE:
<221> NAME/KEY: MISC_FEATURE
<222> LOCATION: (7)..(7)
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is F or L
<220> FEATURE:
<221> NAME/KEY: MISC_FEATURE
<222> LOCATION: (9)..(9)
<223> OTHER INFORMATION: X at position 9 is I or L
<220> FEATURE:
<221> NAME/KEY: MISC_FEATURE
<222> LOCATION: (10)..(10)
<223> OTHER INFORMATION: X at position 10 is any amino acid
<220> FEATURE:
<221> NAME/KEY: MISC_FEATURE
<222> LOCATION: (11)..(11)
<223> OTHER INFORMATION: X at position 11 is any amino acid
<220> FEATURE:
<221> NAME/KEY: MISC_FEATURE
<222> LOCATION: (12)..(12)
<223> OTHER INFORMATION: X at position 12 is any amino acid

<400> SEQUENCE: 2

Leu Xaa Xaa Leu Leu Leu Xaa Xaa Xaa Xaa Xaa Xaa Leu
1               5                   10

<210> SEQ ID NO 3
<211> LENGTH: 17
```

```
<212> TYPE: PRT
<213> ORGANISM: Artificial
<220> FEATURE:
<223> OTHER INFORMATION: Consensus peptide
<220> FEATURE:
<221> NAME/KEY: MISC_FEATURE
<222> LOCATION: (1)..(1)
<223> OTHER INFORMATION: X at position 1 is Q or E
<220> FEATURE:
<221> NAME/KEY: MISC_FEATURE
<222> LOCATION: (2)..(2)
<223> OTHER INFORMATION: X at position 2 is Q or E
<220> FEATURE:
<221> NAME/KEY: MISC_FEATURE
<222> LOCATION: (3)..(3)
<223> OTHER INFORMATION: X at position 3 is L, I, V, or F
<220> FEATURE:
<221> NAME/KEY: MISC_FEATURE
<222> LOCATION: (4)..(4)
<223> OTHER INFORMATION: X at position 4 is any amino acid
<220> FEATURE:
<221> NAME/KEY: MISC_FEATURE
<222> LOCATION: (5)..(5)
<223> OTHER INFORMATION: X at position 5 is optional, any amino acid
<220> FEATURE:
<221> NAME/KEY: MISC_FEATURE
<222> LOCATION: (6)..(6)
<223> OTHER INFORMATION: X at position 6 is L, I, V, or F
<220> FEATURE:
<221> NAME/KEY: MISC_FEATURE
<222> LOCATION: (7)..(7)
<223> OTHER INFORMATION: X at position 7 is L, I, V, or F
<220> FEATURE:
<221> NAME/KEY: MISC_FEATURE
<222> LOCATION: (8)..(8)
<223> OTHER INFORMATION: X at position 8 is L, I, V, or F
<220> FEATURE:
<221> NAME/KEY: MISC_FEATURE
<222> LOCATION: (9)..(9)
<223> OTHER INFORMATION: X at position 9 is any amino acid
<220> FEATURE:
<221> NAME/KEY: MISC_FEATURE
<222> LOCATION: (10)..(10)
<223> OTHER INFORMATION: X at position 10 is L, I, V, or F
<220> FEATURE:
<221> NAME/KEY: MISC_FEATURE
<222> LOCATION: (11)..(11)
<223> OTHER INFORMATION: X at position 11 is L, I, V, or F
<220> FEATURE:
<221> NAME/KEY: MISC_FEATURE
<222> LOCATION: (12)..(12)
<223> OTHER INFORMATION: X at position 12 is any amino acid
<220> FEATURE:
<221> NAME/KEY: MISC_FEATURE
<222> LOCATION: (13)..(13)
<223> OTHER INFORMATION: X at position 13 is any amino acid
<220> FEATURE:
<221> NAME/KEY: MISC_FEATURE
<222> LOCATION: (14)..(14)
<223> OTHER INFORMATION: X at position 14 is any amino acid
<220> FEATURE:
<221> NAME/KEY: MISC_FEATURE
<222> LOCATION: (15)..(15)
<223> OTHER INFORMATION: X at position 15 is L, I, V, or F
<220> FEATURE:
<221> NAME/KEY: MISC_FEATURE
<222> LOCATION: (16)..(16)
<223> OTHER INFORMATION: X at position 16 is D, G, Q, or E
<220> FEATURE:
<221> NAME/KEY: MISC_FEATURE
<222> LOCATION: (17)..(17)
<223> OTHER INFORMATION: X at position 17 is D, G, Q, or E

<400> SEQUENCE: 3

Xaa Xaa Xaa Xaa Xaa Xaa Xaa Xaa Xaa Xaa Xaa Xaa Xaa Xaa Xaa
1               5                   10                  15

Xaa
```

```
<210> SEQ ID NO 4
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is L, I, V, or F
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is optional, any amino acid
<220> FEATURE:
<221> NAME/KEY: MISC_FEATURE
<222> LOCATION: (4)..(4)
<223> OTHER INFORMATION: X at position 4 is L, I, V, or F
<220> FEATURE:
<221> NAME/KEY: MISC_FEATURE
<222> LOCATION: (5)..(5)
<223> OTHER INFORMATION: X at position 5 is L, I, V, or F
<220> FEATURE:
<221> NAME/KEY: MISC_FEATURE
<222> LOCATION: (6)..(6)
<223> OTHER INFORMATION: X at position 6 is L, I, V, or F
<220> FEATURE:
<221> NAME/KEY: MISC_FEATURE
<222> LOCATION: (7)..(7)
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is L, I, V, or F
<220> FEATURE:
<221> NAME/KEY: MISC_FEATURE
<222> LOCATION: (9)..(9)
<223> OTHER INFORMATION: X at position 9 is L, I, V, or F
<220> FEATURE:
<221> NAME/KEY: MISC_FEATURE
<222> LOCATION: (10)..(10)
<223> OTHER INFORMATION: X at position 10 is any amino acid
<220> FEATURE:
<221> NAME/KEY: MISC_FEATURE
<222> LOCATION: (11)..(11)
<223> OTHER INFORMATION: X at position 11 is any amino acid
<220> FEATURE:
<221> NAME/KEY: MISC_FEATURE
<222> LOCATION: (12)..(12)
<223> OTHER INFORMATION: X at position 12 is any amino acid
<220> FEATURE:
<221> NAME/KEY: MISC_FEATURE
<222> LOCATION: (13)..(13)
<223> OTHER INFORMATION: X at position 13 is L, I, V, or F
<220> FEATURE:
<221> NAME/KEY: MISC_FEATURE
<222> LOCATION: (14)..(14)
<223> OTHER INFORMATION: X at position 14 is D, G, Q, or E
<220> FEATURE:
<221> NAME/KEY: MISC_FEATURE
<222> LOCATION: (15)..(15)
<223> OTHER INFORMATION: X at position 15 is D, G, Q, or E

<400> SEQUENCE: 4

Xaa Xaa Xaa Xaa Xaa Xaa Xaa Xaa Xaa Xaa Xaa Xaa Xaa Xaa Xaa
1               5                   10                  15

<210> SEQ ID NO 5
<211> LENGTH: 15
<212> TYPE: PRT
<213> ORGANISM: Artificial
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is Q or E
<220> FEATURE:
<221> NAME/KEY: MISC_FEATURE
<222> LOCATION: (2)..(2)
<223> OTHER INFORMATION: X at position 2 is Q or E
<220> FEATURE:
<221> NAME/KEY: MISC_FEATURE
<222> LOCATION: (3)..(3)
<223> OTHER INFORMATION: X at position 3 is L, I, V, or F
<220> FEATURE:
<221> NAME/KEY: MISC_FEATURE
<222> LOCATION: (4)..(4)
<223> OTHER INFORMATION: X at position 4 is any amino acid
<220> FEATURE:
<221> NAME/KEY: MISC_FEATURE
<222> LOCATION: (5)..(5)
<223> OTHER INFORMATION: X at position 5 is optional, any amino acid
<220> FEATURE:
<221> NAME/KEY: MISC_FEATURE
<222> LOCATION: (6)..(6)
<223> OTHER INFORMATION: X at position 6 is L, I, V, or F
<220> FEATURE:
<221> NAME/KEY: MISC_FEATURE
<222> LOCATION: (7)..(7)
<223> OTHER INFORMATION: X at position 7 is L, I, V, or F
<220> FEATURE:
<221> NAME/KEY: MISC_FEATURE
<222> LOCATION: (8)..(8)
<223> OTHER INFORMATION: X at position 8 is L, I, V, or F
<220> FEATURE:
<221> NAME/KEY: MISC_FEATURE
<222> LOCATION: (9)..(9)
<223> OTHER INFORMATION: X at position 9 is any amino acid
<220> FEATURE:
<221> NAME/KEY: MISC_FEATURE
<222> LOCATION: (10)..(10)
<223> OTHER INFORMATION: X at position 10 is L, I, V, or F
<220> FEATURE:
<221> NAME/KEY: MISC_FEATURE
<222> LOCATION: (11)..(11)
<223> OTHER INFORMATION: X at position 11 is L, I, V, or F
<220> FEATURE:
<221> NAME/KEY: MISC_FEATURE
<222> LOCATION: (12)..(12)
<223> OTHER INFORMATION: X at position 12 is any amino acid
<220> FEATURE:
<221> NAME/KEY: MISC_FEATURE
<222> LOCATION: (13)..(13)
<223> OTHER INFORMATION: X at position 13 is any amino acid
<220> FEATURE:
<221> NAME/KEY: MISC_FEATURE
<222> LOCATION: (14)..(14)
<223> OTHER INFORMATION: X at position 14 is any amino acid
<220> FEATURE:
<221> NAME/KEY: MISC_FEATURE
<222> LOCATION: (15)..(15)
<223> OTHER INFORMATION: X at position 15 is L, I, V, or F

<400> SEQUENCE: 5

Xaa Xaa Xaa Xaa Xaa Xaa Xaa Xaa Xaa Xaa Xaa Xaa Xaa Xaa Xaa
1               5                   10                  15

<210> SEQ ID NO 6
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is L, I, V, F, A, or a non-
``` hydrophobic amino acid
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is optional, any amino acid
<220> FEATURE:
<221> NAME/KEY: MISC_FEATURE
<222> LOCATION: (4)..(4)
<223> OTHER INFORMATION: X at position 4 is L, I, V, F, A, or a non-
    hydrophobic amino acid
<220> FEATURE:
<221> NAME/KEY: MISC_FEATURE
<222> LOCATION: (5)..(5)
<223> OTHER INFORMATION: X at position 5 is L, I, V, F, A, or a non-
    hydrophobic amino acid
<220> FEATURE:
<221> NAME/KEY: MISC_FEATURE
<222> LOCATION: (6)..(6)
<223> OTHER INFORMATION: X at position 6 is L, I, V, F, A, or a non-
    hydrophobic amino acid
<220> FEATURE:
<221> NAME/KEY: MISC_FEATURE
<222> LOCATION: (7)..(7)
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is L, I, V, F, A, or a non-
    hydrophobic amino acid
<220> FEATURE:
<221> NAME/KEY: MISC_FEATURE
<222> LOCATION: (9)..(9)
<223> OTHER INFORMATION: X at position 9 is L, I, V, F, A, or a non-
    hydrophobic amino acid
<220> FEATURE:
<221> NAME/KEY: MISC_FEATURE
<222> LOCATION: (10)..(10)
<223> OTHER INFORMATION: X at position 10 is any amino acid
<220> FEATURE:
<221> NAME/KEY: MISC_FEATURE
<222> LOCATION: (11)..(11)
<223> OTHER INFORMATION: X at position 11 is any amino acid
<220> FEATURE:
<221> NAME/KEY: MISC_FEATURE
<222> LOCATION: (12)..(12)
<223> OTHER INFORMATION: X at position 12 is any amino acid
<220> FEATURE:
<221> NAME/KEY: MISC_FEATURE
<222> LOCATION: (13)..(13)
<223> OTHER INFORMATION: X at position 13 is L, I, V, F, A, or a non-
    hydrophobic amino acid

<400> SEQUENCE: 6

Xaa Xaa Xaa Xaa Xaa Xaa Xaa Xaa Xaa Xaa Xaa Xaa Xaa
1               5                   10

<210> SEQ ID NO 7
<211> LENGTH: 22
<212> TYPE: PRT
<213> ORGANISM: Artificial
<220> FEATURE:
<223> OTHER INFORMATION: Wildtype peptide

<400> SEQUENCE: 7

Ser Ala Gly Ser Glu Gln Gln Leu Asp Gln Leu Leu Ala Met Phe Ile
1               5                   10                  15

Met Met Met Leu Gln Gln
            20

<210> SEQ ID NO 8

```
<211> LENGTH: 21
<212> TYPE: PRT
<213> ORGANISM: Artificial
<220> FEATURE:
<223> OTHER INFORMATION: Synthetic peptide

<400> SEQUENCE: 8

Ser Ala Gly Ser Glu Gln Gln Leu Asp Leu Leu Leu Met Phe Ile Met
1               5                   10                  15

Met Met Leu Gln Gln
            20

<210> SEQ ID NO 9
<211> LENGTH: 22
<212> TYPE: PRT
<213> ORGANISM: Artificial
<220> FEATURE:
<223> OTHER INFORMATION: Synthetic peptide

<400> SEQUENCE: 9

Ser Ala Gly Ser Glu Gln Gln Leu Asp Gln Leu Leu Leu Met Phe Ile
1               5                   10                  15

Met Met Met Leu Gln Gln
            20

<210> SEQ ID NO 10
<211> LENGTH: 21
<212> TYPE: PRT
<213> ORGANISM: Artificial
<220> FEATURE:
<223> OTHER INFORMATION: Synthetic peptide

<400> SEQUENCE: 10

Ser Ala Gly Ser Glu Gln Gln Leu Asp Leu Leu Leu Met Phe Ile Ala
1               5                   10                  15

Ala Ala Leu Gln Gln
            20

<210> SEQ ID NO 11
<211> LENGTH: 21
<212> TYPE: PRT
<213> ORGANISM: Artificial
<220> FEATURE:
<223> OTHER INFORMATION: Synthetic peptide

<400> SEQUENCE: 11

Ser Ala Gly Ser Glu Gln Gln Leu Asp Leu Leu Leu Ala Phe Ile Ala
1               5                   10                  15

Ala Ala Leu Gln Gln
            20

<210> SEQ ID NO 12
<211> LENGTH: 21
<212> TYPE: PRT
<213> ORGANISM: Artificial
<220> FEATURE:
<223> OTHER INFORMATION: Synthetic peptide

<400> SEQUENCE: 12

Ser Ala Gly Ser Glu Gln Gln Leu Glu Leu Leu Leu Ala Phe Ile Ala
1               5                   10                  15

Ala Ala Leu Gln Gln
            20
```

```
<210> SEQ ID NO 13
<211> LENGTH: 18
<212> TYPE: PRT
<213> ORGANISM: Artificial
<220> FEATURE:
<223> OTHER INFORMATION: Synthetic peptide

<400> SEQUENCE: 13

Ser Glu Glu Glu Glu Glu Leu Asp Leu Leu Leu Ala Phe Ile Ala Ala
1               5                   10                  15

Ala Leu

<210> SEQ ID NO 14
<211> LENGTH: 20
<212> TYPE: PRT
<213> ORGANISM: Artificial
<220> FEATURE:
<223> OTHER INFORMATION: Synthetic peptide

<400> SEQUENCE: 14

Ser Glu Glu Glu Glu Glu Leu Asp Leu Leu Leu Ala Phe Ile Ala Ala
1               5                   10                  15

Ala Leu Gln Gln
        20

<210> SEQ ID NO 15
<211> LENGTH: 18
<212> TYPE: PRT
<213> ORGANISM: Artificial
<220> FEATURE:
<223> OTHER INFORMATION: Synthetic peptide

<400> SEQUENCE: 15

Leu Asp Leu Leu Leu Ala Phe Ile Ala Ala Ala Leu Glu Glu Glu Glu
1               5                   10                  15

Glu Glu

<210> SEQ ID NO 16
<211> LENGTH: 16
<212> TYPE: PRT
<213> ORGANISM: Artificial
<220> FEATURE:
<223> OTHER INFORMATION: Synthetic peptide

<400> SEQUENCE: 16

Leu Asp Leu Leu Leu Ala Phe Ile Glu Glu Glu Leu Glu Glu Glu Glu
1               5                   10                  15

<210> SEQ ID NO 17
<211> LENGTH: 18
<212> TYPE: PRT
<213> ORGANISM: Artificial
<220> FEATURE:
<223> OTHER INFORMATION: Synthetic peptide

<400> SEQUENCE: 17

Ser Glu Glu Glu Leu Asp Leu Leu Leu Ala Phe Ile Ala Ala Ala Leu
1               5                   10                  15

Glu Glu

<210> SEQ ID NO 18
<211> LENGTH: 18
<212> TYPE: PRT
<213> ORGANISM: Artificial
<220> FEATURE:
```

<223> OTHER INFORMATION: Synthetic peptide

<400> SEQUENCE: 18

Ser Glu Glu Glu Leu Asp Leu Leu Leu Ala Phe Ile Glu Glu Leu
1               5                   10                  15

Glu Glu

<210> SEQ ID NO 19
<211> LENGTH: 18
<212> TYPE: PRT
<213> ORGANISM: Artificial
<220> FEATURE:
<223> OTHER INFORMATION: Synthetic peptide

<400> SEQUENCE: 19

Ser Glu Glu Glu Leu Asp Leu Leu Leu Ala Phe Ile Ala Ala Ala Leu
1               5                   10                  15

Asp Asp

<210> SEQ ID NO 20
<211> LENGTH: 20
<212> TYPE: PRT
<213> ORGANISM: Artificial
<220> FEATURE:
<223> OTHER INFORMATION: Synthetic peptide

<400> SEQUENCE: 20

Ser Glu Glu Glu Glu Glu Leu Asp Leu Leu Leu Ala Phe Ile Ala Ala
1               5                   10                  15

Ala Leu Gly Gly
            20

<210> SEQ ID NO 21
<211> LENGTH: 22
<212> TYPE: PRT
<213> ORGANISM: Artificial
<220> FEATURE:
<223> OTHER INFORMATION: Synthetic peptide

<400> SEQUENCE: 21

Ser Glu Glu Glu Glu Glu Glu Glu Leu Asp Leu Leu Leu Ala Phe Ile
1               5                   10                  15

Ala Ala Ala Leu Ala Ala
            20

<210> SEQ ID NO 22
<211> LENGTH: 21
<212> TYPE: PRT
<213> ORGANISM: Artificial
<220> FEATURE:
<223> OTHER INFORMATION: Synthetic peptide

<400> SEQUENCE: 22

Ser Glu Glu Glu Glu Glu Glu Leu Asp Leu Leu Leu Ala Phe Ile Ala
1               5                   10                  15

Ala Ala Leu Ser Ser
            20

<210> SEQ ID NO 23
<211> LENGTH: 21
<212> TYPE: PRT
<213> ORGANISM: Artificial
<220> FEATURE:
<223> OTHER INFORMATION: Synthetic peptide

<400> SEQUENCE: 23

Ser Ala Gly Ser Glu Gln Gln Leu Asp Leu Leu Leu Gly Phe Ile Gly
1               5                   10                  15

Gly Gly Leu Gln Gln
            20

<210> SEQ ID NO 24
<211> LENGTH: 21
<212> TYPE: PRT
<213> ORGANISM: Artificial
<220> FEATURE:
<223> OTHER INFORMATION: Synthetic peptide

<400> SEQUENCE: 24

Ser Ala Gly Ser Glu Gln Gln Leu Asp Leu Leu Leu Ser Phe Ile Ser
1               5                   10                  15

Ser Ser Leu Gln Gln
            20

<210> SEQ ID NO 25
<211> LENGTH: 19
<212> TYPE: PRT
<213> ORGANISM: Artificial
<220> FEATURE:
<223> OTHER INFORMATION: Synthetic peptide

<400> SEQUENCE: 25

Ser Glu Glu Glu Glu Glu Leu Asp Leu Leu Leu Ala Phe Ile Ala Ala
1               5                   10                  15

Ala Leu Gln

<210> SEQ ID NO 26
<211> LENGTH: 19
<212> TYPE: PRT
<213> ORGANISM: Artificial
<220> FEATURE:
<223> OTHER INFORMATION: Synthetic peptide

<400> SEQUENCE: 26

Ser Glu Glu Glu Glu Glu Leu Asp Leu Leu Leu Ala Phe Ile Ala Ala
1               5                   10                  15

Ala Leu Ser

<210> SEQ ID NO 27
<211> LENGTH: 19
<212> TYPE: PRT
<213> ORGANISM: Artificial
<220> FEATURE:
<223> OTHER INFORMATION: Synthetic peptide

<400> SEQUENCE: 27

Ser Glu Glu Glu Glu Glu Leu Asp Leu Leu Leu Ala Phe Ile Ala Ala
1               5                   10                  15

Ala Leu Ala

<210> SEQ ID NO 28
<211> LENGTH: 19
<212> TYPE: PRT
<213> ORGANISM: Artificial
<220> FEATURE:
<223> OTHER INFORMATION: Synthetic peptide

<400> SEQUENCE: 28

Ser Glu Glu Glu Glu Glu Leu Asp Leu Leu Leu Ala Phe Ile Ala Ala
1               5                   10                  15

Ala Leu Glu

<210> SEQ ID NO 29
<211> LENGTH: 19
<212> TYPE: PRT
<213> ORGANISM: Artificial
<220> FEATURE:
<223> OTHER INFORMATION: Synthetic peptide

<400> SEQUENCE: 29

Ser Glu Leu Glu Leu Leu Leu Ala Phe Ile Ala Ala Ala Leu Glu Glu
1               5                   10                  15

Glu Glu Glu

<210> SEQ ID NO 30
<211> LENGTH: 20
<212> TYPE: PRT
<213> ORGANISM: Artificial
<220> FEATURE:
<223> OTHER INFORMATION: Synthetic peptide

<400> SEQUENCE: 30

Ser Glu Glu Glu Leu Glu Leu Leu Leu Ala Phe Ile Ala Ala Ala Leu
1               5                   10                  15

Glu Glu Glu Glu
            20

<210> SEQ ID NO 31
<211> LENGTH: 19
<212> TYPE: PRT
<213> ORGANISM: Artificial
<220> FEATURE:
<223> OTHER INFORMATION: Synthetic peptide

<400> SEQUENCE: 31

Ser Glu Leu Asp Leu Leu Leu Ala Phe Ile Ala Ala Ala Leu Glu Glu
1               5                   10                  15

Glu Glu Glu

<210> SEQ ID NO 32
<211> LENGTH: 20
<212> TYPE: PRT
<213> ORGANISM: Artificial
<220> FEATURE:
<223> OTHER INFORMATION: Synthetic peptide

<400> SEQUENCE: 32

Ser Glu Glu Glu Glu Glu Leu Asp Leu Leu Leu Ala Leu Ile Ala Ala
1               5                   10                  15

Ala Leu Gln Gln
            20

<210> SEQ ID NO 33
<211> LENGTH: 20
<212> TYPE: PRT
<213> ORGANISM: Artificial
<220> FEATURE:
<223> OTHER INFORMATION: Synthetic peptide

<400> SEQUENCE: 33

Ser Glu Glu Gln Leu Glu Leu Leu Leu Ala Phe Ile Ala Ala Ala Leu

```
1               5                   10                  15
Gln Gln Glu Glu
            20

<210> SEQ ID NO 34
<211> LENGTH: 19
<212> TYPE: PRT
<213> ORGANISM: Artificial
<220> FEATURE:
<223> OTHER INFORMATION: Synthetic peptide

<400> SEQUENCE: 34

Ser Glu Glu Gln Leu Asp Leu Leu Leu Ala Phe Ile Ala Ala Ala Leu
1               5                   10                  15

Gln Glu Glu

<210> SEQ ID NO 35
<211> LENGTH: 16
<212> TYPE: PRT
<213> ORGANISM: Artificial
<220> FEATURE:
<223> OTHER INFORMATION: Synthetic peptide

<400> SEQUENCE: 35

Ser Glu Leu Glu Leu Leu Leu Ala Phe Ile Glu Glu Glu Leu Glu Glu
1               5                   10                  15

<210> SEQ ID NO 36
<211> LENGTH: 16
<212> TYPE: PRT
<213> ORGANISM: Artificial
<220> FEATURE:
<223> OTHER INFORMATION: Synthetic peptide

<400> SEQUENCE: 36

Ser Glu Leu Glu Leu Leu Leu Glu Phe Ile Glu Glu Glu Leu Glu Glu
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic peptide

<400> SEQUENCE: 37

Ser Glu Leu Glu Leu Leu Leu Glu Phe Ile Glu Glu Glu Leu Glu
1               5                   10                  15

<210> SEQ ID NO 38
<211> LENGTH: 15
<212> TYPE: PRT
<213> ORGANISM: Artificial
<220> FEATURE:
<223> OTHER INFORMATION: Synthetic peptide

<400> SEQUENCE: 38

Ser Glu Leu Glu Leu Leu Leu Glu Leu Ile Glu Glu Glu Leu Glu
1               5                   10                  15

<210> SEQ ID NO 39
<211> LENGTH: 20
<212> TYPE: PRT
<213> ORGANISM: Artificial
<220> FEATURE:
<223> OTHER INFORMATION: Synthetic peptide
```

-continued

<400> SEQUENCE: 39

Ser Glu Glu Gln Leu Asp Leu Leu Leu Glu Phe Ile Glu Glu Leu
1               5                   10                  15

Gln Gln Glu Glu
            20

<210> SEQ ID NO 40
<211> LENGTH: 19
<212> TYPE: PRT
<213> ORGANISM: Artificial
<220> FEATURE:
<223> OTHER INFORMATION: Synthetic peptide

<400> SEQUENCE: 40

Ser Glu Leu Asp Leu Leu Leu Ala Phe Ile Asp Asp Leu Glu Glu
1               5                   10                  15

Glu Glu Glu

<210> SEQ ID NO 41
<211> LENGTH: 21
<212> TYPE: PRT
<213> ORGANISM: Artificial
<220> FEATURE:
<223> OTHER INFORMATION: Synthetic peptide

<400> SEQUENCE: 41

Ser Ala Gly Ser Glu Glu Leu Asp Leu Leu Leu Met Phe Ile Met
1               5                   10                  15

Met Met Leu Glu Glu
            20

<210> SEQ ID NO 42
<211> LENGTH: 18
<212> TYPE: PRT
<213> ORGANISM: Artificial
<220> FEATURE:
<223> OTHER INFORMATION: Synthetic peptide

<400> SEQUENCE: 42

Ser Glu Glu Glu Leu Asp Leu Leu Leu Met Phe Ile Met Met Met Leu
1               5                   10                  15

Glu Glu

<210> SEQ ID NO 43
<211> LENGTH: 19
<212> TYPE: PRT
<213> ORGANISM: Artificial
<220> FEATURE:
<223> OTHER INFORMATION: Synthetic peptide

<400> SEQUENCE: 43

Ser Glu Glu Glu Gln Leu Asp Leu Leu Leu Met Phe Ile Met Met Met
1               5                   10                  15

Leu Glu Glu

<210> SEQ ID NO 44
<211> LENGTH: 20
<212> TYPE: PRT
<213> ORGANISM: Artificial
<220> FEATURE:
<223> OTHER INFORMATION: Synthetic peptide

<400> SEQUENCE: 44

```
Ser Glu Glu Gln Leu Asp Leu Leu Leu Met Phe Ile Met Met Met
1               5                   10                  15

Leu Gln Glu Glu
            20

<210> SEQ ID NO 45
<211> LENGTH: 20
<212> TYPE: PRT
<213> ORGANISM: Artificial
<220> FEATURE:
<223> OTHER INFORMATION: Synthetic peptide

<400> SEQUENCE: 45

Ser Glu Glu Gln Leu Asp Leu Leu Leu Met Phe Ile Met Met Leu
1               5                   10                  15

Gln Gln Glu Glu
            20

<210> SEQ ID NO 46
<211> LENGTH: 13
<212> TYPE: PRT
<213> ORGANISM: Artificial
<220> FEATURE:
<223> OTHER INFORMATION: Synthetic peptide

<400> SEQUENCE: 46

Leu Glu Leu Leu Leu Glu Phe Ile Glu Glu Glu Leu Glu
1               5                   10

<210> SEQ ID NO 47
<211> LENGTH: 14
<212> TYPE: PRT
<213> ORGANISM: Artificial
<220> FEATURE:
<223> OTHER INFORMATION: Synthetic peptide

<400> SEQUENCE: 47

Leu Glu Leu Leu Leu Glu Phe Ile Glu Glu Glu Leu Glu Glu
1               5                   10

<210> SEQ ID NO 48
<211> LENGTH: 14
<212> TYPE: PRT
<213> ORGANISM: Artificial
<220> FEATURE:
<223> OTHER INFORMATION: Synthetic peptide

<400> SEQUENCE: 48

Ser Glu Leu Glu Leu Leu Leu Glu Phe Ile Glu Glu Glu Leu
1               5                   10

<210> SEQ ID NO 49
<211> LENGTH: 15
<212> TYPE: PRT
<213> ORGANISM: Artificial
<220> FEATURE:
<223> OTHER INFORMATION: Synthetic peptide

<400> SEQUENCE: 49

Leu Asp Gln Leu Leu Leu Met Phe Ile Met Met Met Leu Gln Gln
1               5                   10                  15

<210> SEQ ID NO 50
<211> LENGTH: 21
<212> TYPE: PRT
```

```
<213> ORGANISM: Artificial
<220> FEATURE:
<223> OTHER INFORMATION: Synthetic peptide

<400> SEQUENCE: 50

Ser Glu Glu Glu Glu Glu Leu Asp Gln Leu Leu Leu Ala Phe Ile Ala
1               5                   10                  15

Ala Ala Leu Gln Gln
            20

<210> SEQ ID NO 51
<211> LENGTH: 19
<212> TYPE: PRT
<213> ORGANISM: Artificial
<220> FEATURE:
<223> OTHER INFORMATION: Synthetic peptide

<400> SEQUENCE: 51

Ser Glu Glu Glu Glu Glu Leu Asp Gln Leu Leu Leu Ala Phe Ile Ala
1               5                   10                  15

Ala Ala Leu

<210> SEQ ID NO 52
<211> LENGTH: 21
<212> TYPE: PRT
<213> ORGANISM: Artificial
<220> FEATURE:
<223> OTHER INFORMATION: Synthetic peptide

<400> SEQUENCE: 52

Ser Glu Glu Glu Glu Gln Leu Asp Gln Leu Leu Leu Ala Phe Ile Ala
1               5                   10                  15

Ala Ala Leu Gln Gln
            20

<210> SEQ ID NO 53
<211> LENGTH: 20
<212> TYPE: PRT
<213> ORGANISM: Artificial
<220> FEATURE:
<223> OTHER INFORMATION: Synthetic peptide

<400> SEQUENCE: 53

Ser Glu Glu Gln Leu Asp Gln Leu Leu Leu Ala Phe Ile Ala Ala Ala
1               5                   10                  15

Leu Gln Glu Glu
        20

<210> SEQ ID NO 54
<211> LENGTH: 19
<212> TYPE: PRT
<213> ORGANISM: Artificial
<220> FEATURE:
<223> OTHER INFORMATION: Synthetic peptide

<400> SEQUENCE: 54

Ser Glu Glu Gln Leu Asp Gln Leu Leu Leu Ala Phe Ile Ala Ala Ala
1               5                   10                  15

Leu Glu Glu

<210> SEQ ID NO 55
<211> LENGTH: 19
<212> TYPE: PRT
<213> ORGANISM: Artificial
```

<220> FEATURE:
<223> OTHER INFORMATION: Synthetic peptide

<400> SEQUENCE: 55

Ser Glu Glu Glu Leu Asp Gln Leu Leu Leu Met Phe Ile Met Met Met
1               5                   10                  15

Leu Glu Glu

<210> SEQ ID NO 56
<211> LENGTH: 20
<212> TYPE: PRT
<213> ORGANISM: Artificial
<220> FEATURE:
<223> OTHER INFORMATION: Synthetic peptide

<400> SEQUENCE: 56

Ser Glu Glu Glu Gln Leu Asp Gln Leu Leu Leu Met Phe Ile Met Met
1               5                   10                  15

Met Leu Glu Glu
            20

<210> SEQ ID NO 57
<211> LENGTH: 21
<212> TYPE: PRT
<213> ORGANISM: Artificial
<220> FEATURE:
<223> OTHER INFORMATION: Synthetic peptide

<400> SEQUENCE: 57

Ser Glu Glu Glu Gln Leu Asp Gln Leu Leu Leu Met Phe Ile Met Met
1               5                   10                  15

Met Leu Gln Glu Glu
            20

<210> SEQ ID NO 58
<211> LENGTH: 21
<212> TYPE: PRT
<213> ORGANISM: Artificial
<220> FEATURE:
<223> OTHER INFORMATION: Synthetic peptide

<400> SEQUENCE: 58

Ser Glu Glu Gln Leu Asp Gln Leu Leu Leu Met Phe Ile Met Met Met
1               5                   10                  15

Leu Gln Gln Glu Glu
            20

<210> SEQ ID NO 59
<211> LENGTH: 15
<212> TYPE: PRT
<213> ORGANISM: Artificial
<220> FEATURE:
<223> OTHER INFORMATION: Synthetic peptide

<400> SEQUENCE: 59

Leu Asp Gln Leu Leu Leu Ala Phe Ile Ala Ala Ala Leu Gln Gln
1               5                   10                  15

<210> SEQ ID NO 60
<211> LENGTH: 15
<212> TYPE: PRT
<213> ORGANISM: Artificial
<220> FEATURE:
<223> OTHER INFORMATION: Synthetic peptide

```
<400> SEQUENCE: 60

Leu Asp Gln Leu Leu Leu Glu Phe Ile Glu Glu Glu Leu Gln Gln
1               5                   10                  15

<210> SEQ ID NO 61
<211> LENGTH: 16
<212> TYPE: PRT
<213> ORGANISM: Artificial
<220> FEATURE:
<223> OTHER INFORMATION: Synthetic peptide

<400> SEQUENCE: 61

Gln Leu Asp Gln Leu Leu Leu Met Phe Ile Met Met Met Leu Gln Gln
1               5                   10                  15

<210> SEQ ID NO 62
<211> LENGTH: 16
<212> TYPE: PRT
<213> ORGANISM: Artificial
<220> FEATURE:
<223> OTHER INFORMATION: Synthetic peptide

<400> SEQUENCE: 62

Gln Leu Asp Gln Leu Leu Leu Ala Phe Ile Ala Ala Ala Leu Gln Gln
1               5                   10                  15

<210> SEQ ID NO 63
<211> LENGTH: 16
<212> TYPE: PRT
<213> ORGANISM: Artificial
<220> FEATURE:
<223> OTHER INFORMATION: Synthetic peptide

<400> SEQUENCE: 63

Gln Leu Asp Gln Leu Leu Leu Glu Phe Ile Glu Glu Glu Leu Gln Gln
1               5                   10                  15

<210> SEQ ID NO 64
<211> LENGTH: 17
<212> TYPE: PRT
<213> ORGANISM: Artificial
<220> FEATURE:
<223> OTHER INFORMATION: Synthetic peptide

<400> SEQUENCE: 64

Gln Gln Leu Asp Gln Leu Leu Leu Met Phe Ile Met Met Met Leu Gln
1               5                   10                  15

Gln

<210> SEQ ID NO 65
<211> LENGTH: 17
<212> TYPE: PRT
<213> ORGANISM: Artificial
<220> FEATURE:
<223> OTHER INFORMATION: Synthetic peptide

<400> SEQUENCE: 65

Gln Gln Leu Asp Gln Leu Leu Leu Ala Phe Ile Ala Ala Ala Leu Gln
1               5                   10                  15

Gln

<210> SEQ ID NO 66
<211> LENGTH: 17
<212> TYPE: PRT
<213> ORGANISM: Artificial
```

```
<220> FEATURE:
<223> OTHER INFORMATION: Synthetic peptide

<400> SEQUENCE: 66

Gln Gln Leu Asp Gln Leu Leu Leu Glu Phe Ile Glu Glu Leu Gln
1               5                   10                  15

Gln

<210> SEQ ID NO 67
<211> LENGTH: 13
<212> TYPE: PRT
<213> ORGANISM: Artificial
<220> FEATURE:
<223> OTHER INFORMATION: Synthetic peptide

<400> SEQUENCE: 67

Leu Asp Gln Leu Leu Leu Met Phe Ile Met Met Met Leu
1               5                   10

<210> SEQ ID NO 68
<211> LENGTH: 13
<212> TYPE: PRT
<213> ORGANISM: Artificial
<220> FEATURE:
<223> OTHER INFORMATION: Synthetic peptide

<400> SEQUENCE: 68

Leu Asp Gln Leu Leu Leu Ala Phe Ile Ala Ala Ala Leu
1               5                   10

<210> SEQ ID NO 69
<211> LENGTH: 13
<212> TYPE: PRT
<213> ORGANISM: Artificial
<220> FEATURE:
<223> OTHER INFORMATION: Synthetic peptide

<400> SEQUENCE: 69

Leu Asp Gln Leu Leu Leu Glu Phe Ile Glu Glu Glu Leu
1               5                   10

<210> SEQ ID NO 70
<211> LENGTH: 22
<212> TYPE: PRT
<213> ORGANISM: Artificial
<220> FEATURE:
<223> OTHER INFORMATION: Synthetic peptide

<400> SEQUENCE: 70

Ser Ala Gly Ser Glu Glu Glu Leu Asp Gln Leu Leu Leu Met Phe Ile
1               5                   10                  15

Met Met Met Leu Glu Glu
            20

<210> SEQ ID NO 71
<211> LENGTH: 21
<212> TYPE: PRT
<213> ORGANISM: Artificial
<220> FEATURE:
<223> OTHER INFORMATION: Synthetic peptide

<400> SEQUENCE: 71

Ser Ala Gly Ser Glu Gln Gln Glu Asp Leu Leu Leu Met Phe Ile Met
1               5                   10                  15

Met Met Leu Gln Gln
```

20

<210> SEQ ID NO 72
<211> LENGTH: 21
<212> TYPE: PRT
<213> ORGANISM: Artificial
<220> FEATURE:
<223> OTHER INFORMATION: Synthetic peptide

<400> SEQUENCE: 72

Ser Ala Gly Ser Glu Gln Gln Leu Asp Glu Leu Leu Met Phe Ile Met
1               5                   10                  15
Met Met Leu Gln Gln
            20

<210> SEQ ID NO 73
<211> LENGTH: 21
<212> TYPE: PRT
<213> ORGANISM: Artificial
<220> FEATURE:
<223> OTHER INFORMATION: Synthetic peptide

<400> SEQUENCE: 73

Ser Ala Gly Ser Glu Gln Gln Leu Asp Leu Glu Leu Met Phe Ile Met
1               5                   10                  15
Met Met Leu Gln Gln
            20

<210> SEQ ID NO 74
<211> LENGTH: 21
<212> TYPE: PRT
<213> ORGANISM: Artificial
<220> FEATURE:
<223> OTHER INFORMATION: Synthetic peptide

<400> SEQUENCE: 74

Ser Ala Gly Ser Glu Gln Gln Leu Asp Leu Leu Glu Met Phe Ile Met
1               5                   10                  15
Met Met Leu Gln Gln
            20

<210> SEQ ID NO 75
<211> LENGTH: 21
<212> TYPE: PRT
<213> ORGANISM: Artificial
<220> FEATURE:
<223> OTHER INFORMATION: Synthetic peptide

<400> SEQUENCE: 75

Ser Ala Gly Ser Glu Gln Gln Leu Asp Leu Leu Leu Glu Phe Ile Met
1               5                   10                  15
Met Met Leu Gln Gln
            20

<210> SEQ ID NO 76
<211> LENGTH: 21
<212> TYPE: PRT
<213> ORGANISM: Artificial
<220> FEATURE:
<223> OTHER INFORMATION: Synthetic peptide

<400> SEQUENCE: 76

Ser Ala Gly Ser Glu Gln Gln Leu Asp Leu Leu Leu Met Glu Ile Met
1               5                   10                  15

```
Met Met Leu Gln Gln
            20

<210> SEQ ID NO 77
<211> LENGTH: 21
<212> TYPE: PRT
<213> ORGANISM: Artificial
<220> FEATURE:
<223> OTHER INFORMATION: Synthetic peptide

<400> SEQUENCE: 77

Ser Ala Gly Ser Glu Gln Gln Leu Asp Leu Leu Leu Met Phe Glu Met
1               5                   10                  15

Met Met Leu Gln Gln
            20

<210> SEQ ID NO 78
<211> LENGTH: 21
<212> TYPE: PRT
<213> ORGANISM: Artificial
<220> FEATURE:
<223> OTHER INFORMATION: Synthetic peptide

<400> SEQUENCE: 78

Ser Ala Gly Ser Glu Gln Gln Leu Asp Leu Leu Leu Met Phe Ile Glu
1               5                   10                  15

Met Met Leu Gln Gln
            20

<210> SEQ ID NO 79
<211> LENGTH: 21
<212> TYPE: PRT
<213> ORGANISM: Artificial
<220> FEATURE:
<223> OTHER INFORMATION: Synthetic peptide

<400> SEQUENCE: 79

Ser Ala Gly Ser Glu Gln Gln Leu Asp Leu Leu Leu Met Phe Ile Met
1               5                   10                  15

Glu Met Leu Gln Gln
            20

<210> SEQ ID NO 80
<211> LENGTH: 21
<212> TYPE: PRT
<213> ORGANISM: Artificial
<220> FEATURE:
<223> OTHER INFORMATION: Synthetic peptide

<400> SEQUENCE: 80

Ser Ala Gly Ser Glu Gln Gln Leu Asp Leu Leu Leu Met Phe Ile Met
1               5                   10                  15

Met Glu Leu Gln Gln
            20

<210> SEQ ID NO 81
<211> LENGTH: 21
<212> TYPE: PRT
<213> ORGANISM: Artificial
<220> FEATURE:
<223> OTHER INFORMATION: Synthetic peptide

<400> SEQUENCE: 81

Ser Ala Gly Ser Glu Gln Gln Leu Asp Leu Leu Leu Met Phe Ile Met
1               5                   10                  15
```

Met Met Glu Gln Gln
            20

<210> SEQ ID NO 82
<211> LENGTH: 21
<212> TYPE: PRT
<213> ORGANISM: Artificial
<220> FEATURE:
<223> OTHER INFORMATION: Synthetic peptide

<400> SEQUENCE: 82

Ser Ala Gly Ser Glu Gln Gln Leu Lys Leu Leu Leu Met Phe Ile Met
1               5                   10                  15

Met Met Leu Gln Gln
            20

<210> SEQ ID NO 83
<211> LENGTH: 21
<212> TYPE: PRT
<213> ORGANISM: Artificial
<220> FEATURE:
<223> OTHER INFORMATION: Synthetic peptide

<400> SEQUENCE: 83

Ser Ala Gly Ser Glu Ser Ser Leu Asp Leu Leu Leu Met Phe Ile Met
1               5                   10                  15

Met Met Leu Gln Gln
            20

<210> SEQ ID NO 84
<211> LENGTH: 21
<212> TYPE: PRT
<213> ORGANISM: Artificial
<220> FEATURE:
<223> OTHER INFORMATION: Synthetic peptide

<400> SEQUENCE: 84

Ser Ala Gly Ser Glu Gln Gln Leu Asp Leu Leu Leu Met Phe Ile Met
1               5                   10                  15

Met Met Leu Ser Ser
            20

<210> SEQ ID NO 85
<211> LENGTH: 21
<212> TYPE: PRT
<213> ORGANISM: Artificial
<220> FEATURE:
<223> OTHER INFORMATION: Synthetic peptide

<400> SEQUENCE: 85

Ser Ala Gly Ser Glu Gly Gly Leu Asp Leu Leu Leu Met Phe Ile Met
1               5                   10                  15

Met Met Leu Gln Gln
            20

<210> SEQ ID NO 86
<211> LENGTH: 21
<212> TYPE: PRT
<213> ORGANISM: Artificial
<220> FEATURE:
<223> OTHER INFORMATION: Synthetic peptide

<400> SEQUENCE: 86

Ser Ala Gly Ser Glu Gln Gln Leu Asp Leu Leu Leu Met Phe Ile Met

```
1               5                   10                  15

Met Met Leu Gly Gly
            20

<210> SEQ ID NO 87
<211> LENGTH: 21
<212> TYPE: PRT
<213> ORGANISM: Artificial
<220> FEATURE:
<223> OTHER INFORMATION: Synthetic peptide

<400> SEQUENCE: 87

Ser Ala Gly Ser Glu Gln Gln Val Asp Leu Leu Leu Met Phe Ile Met
1               5                   10                  15

Met Met Leu Gln Gln
            20

<210> SEQ ID NO 88
<211> LENGTH: 21
<212> TYPE: PRT
<213> ORGANISM: Artificial
<220> FEATURE:
<223> OTHER INFORMATION: Synthetic peptide

<400> SEQUENCE: 88

Ser Ala Gly Ser Glu Gln Gln Leu Asp Val Leu Leu Met Phe Ile Met
1               5                   10                  15

Met Met Leu Gln Gln
            20

<210> SEQ ID NO 89
<211> LENGTH: 21
<212> TYPE: PRT
<213> ORGANISM: Artificial
<220> FEATURE:
<223> OTHER INFORMATION: Synthetic peptide

<400> SEQUENCE: 89

Ser Ala Gly Ser Glu Gln Gln Leu Asp Leu Val Leu Met Phe Ile Met
1               5                   10                  15

Met Met Leu Gln Gln
            20

<210> SEQ ID NO 90
<211> LENGTH: 21
<212> TYPE: PRT
<213> ORGANISM: Artificial
<220> FEATURE:
<223> OTHER INFORMATION: Synthetic peptide

<400> SEQUENCE: 90

Ser Ala Gly Ser Glu Gln Gln Leu Asp Leu Leu Val Met Phe Ile Met
1               5                   10                  15

Met Met Leu Gln Gln
            20

<210> SEQ ID NO 91
<211> LENGTH: 21
<212> TYPE: PRT
<213> ORGANISM: Artificial
<220> FEATURE:
<223> OTHER INFORMATION: Synthetic peptide

<400> SEQUENCE: 91
```

Ser Ala Gly Ser Glu Gln Gln Leu Asp Leu Leu Val Phe Ile Met
1               5                   10                  15

Met Met Leu Gln Gln
            20

<210> SEQ ID NO 92
<211> LENGTH: 21
<212> TYPE: PRT
<213> ORGANISM: Artificial
<220> FEATURE:
<223> OTHER INFORMATION: Synthetic peptide

<400> SEQUENCE: 92

Ser Ala Gly Ser Glu Gln Gln Leu Asp Leu Leu Met Val Ile Met
1               5                   10                  15

Met Met Leu Gln Gln
            20

<210> SEQ ID NO 93
<211> LENGTH: 21
<212> TYPE: PRT
<213> ORGANISM: Artificial
<220> FEATURE:
<223> OTHER INFORMATION: Synthetic peptide

<400> SEQUENCE: 93

Ser Ala Gly Ser Glu Gln Gln Leu Asp Leu Leu Leu Met Phe Val Met
1               5                   10                  15

Met Met Leu Gln Gln
            20

<210> SEQ ID NO 94
<211> LENGTH: 21
<212> TYPE: PRT
<213> ORGANISM: Artificial
<220> FEATURE:
<223> OTHER INFORMATION: Synthetic peptide

<400> SEQUENCE: 94

Ser Ala Gly Ser Glu Gln Gln Leu Asp Leu Leu Leu Met Phe Ile Val
1               5                   10                  15

Met Met Leu Gln Gln
            20

<210> SEQ ID NO 95
<211> LENGTH: 21
<212> TYPE: PRT
<213> ORGANISM: Artificial
<220> FEATURE:
<223> OTHER INFORMATION: Synthetic peptide

<400> SEQUENCE: 95

Ser Ala Gly Ser Glu Gln Gln Leu Asp Leu Leu Leu Met Phe Ile Met
1               5                   10                  15

Val Met Leu Gln Gln
            20

<210> SEQ ID NO 96
<211> LENGTH: 21
<212> TYPE: PRT
<213> ORGANISM: Artificial
<220> FEATURE:
<223> OTHER INFORMATION: Synthetic peptide

<400> SEQUENCE: 96

```
Ser Ala Gly Ser Glu Gln Gln Leu Asp Leu Leu Leu Met Phe Ile Met
1               5                   10                  15

Met Val Leu Gln Gln
            20
```

<210> SEQ ID NO 97
<211> LENGTH: 21
<212> TYPE: PRT
<213> ORGANISM: Artificial
<220> FEATURE:
<223> OTHER INFORMATION: Synthetic peptide

<400> SEQUENCE: 97

```
Ser Ala Gly Ser Glu Gln Gln Leu Asp Leu Leu Leu Met Phe Ile Met
1               5                   10                  15

Met Met Val Gln Gln
            20
```

<210> SEQ ID NO 98
<211> LENGTH: 22
<212> TYPE: PRT
<213> ORGANISM: Artificial
<220> FEATURE:
<223> OTHER INFORMATION: Synthetic peptide

<400> SEQUENCE: 98

```
Ser Ala Gly Ser Glu Gln Gln Glu Asp Gln Leu Leu Leu Met Phe Ile
1               5                   10                  15

Met Met Met Leu Gln Gln
            20
```

<210> SEQ ID NO 99
<211> LENGTH: 22
<212> TYPE: PRT
<213> ORGANISM: Artificial
<220> FEATURE:
<223> OTHER INFORMATION: Synthetic peptide

<400> SEQUENCE: 99

```
Ser Ala Gly Ser Glu Gln Gln Leu Asp Gln Glu Leu Leu Met Phe Ile
1               5                   10                  15

Met Met Met Leu Gln Gln
            20
```

<210> SEQ ID NO 100
<211> LENGTH: 22
<212> TYPE: PRT
<213> ORGANISM: Artificial
<220> FEATURE:
<223> OTHER INFORMATION: Synthetic peptide

<400> SEQUENCE: 100

```
Ser Ala Gly Ser Glu Gln Gln Leu Asp Gln Leu Glu Leu Met Phe Ile
1               5                   10                  15

Met Met Met Leu Gln Gln
            20
```

<210> SEQ ID NO 101
<211> LENGTH: 22
<212> TYPE: PRT
<213> ORGANISM: Artificial
<220> FEATURE:
<223> OTHER INFORMATION: Synthetic peptide

```
<400> SEQUENCE: 101

Ser Ala Gly Ser Glu Gln Gln Leu Asp Gln Leu Leu Glu Met Phe Ile
1               5                   10                  15

Met Met Met Leu Gln Gln
            20

<210> SEQ ID NO 102
<211> LENGTH: 22
<212> TYPE: PRT
<213> ORGANISM: Artificial
<220> FEATURE:
<223> OTHER INFORMATION: Synthetic peptide

<400> SEQUENCE: 102

Ser Ala Gly Ser Glu Gln Gln Leu Asp Gln Leu Leu Leu Glu Phe Ile
1               5                   10                  15

Met Met Met Leu Gln Gln
            20

<210> SEQ ID NO 103
<211> LENGTH: 22
<212> TYPE: PRT
<213> ORGANISM: Artificial
<220> FEATURE:
<223> OTHER INFORMATION: Synthetic peptide

<400> SEQUENCE: 103

Ser Ala Gly Ser Glu Gln Gln Leu Asp Gln Leu Leu Leu Met Glu Ile
1               5                   10                  15

Met Met Met Leu Gln Gln
            20

<210> SEQ ID NO 104
<211> LENGTH: 22
<212> TYPE: PRT
<213> ORGANISM: Artificial
<220> FEATURE:
<223> OTHER INFORMATION: Synthetic peptide

<400> SEQUENCE: 104

Ser Ala Gly Ser Glu Gln Gln Leu Asp Gln Leu Leu Leu Met Phe Glu
1               5                   10                  15

Met Met Met Leu Gln Gln
            20

<210> SEQ ID NO 105
<211> LENGTH: 22
<212> TYPE: PRT
<213> ORGANISM: Artificial
<220> FEATURE:
<223> OTHER INFORMATION: Synthetic peptide

<400> SEQUENCE: 105

Ser Ala Gly Ser Glu Gln Gln Leu Asp Gln Leu Leu Leu Met Phe Ile
1               5                   10                  15

Glu Met Met Leu Gln Gln
            20

<210> SEQ ID NO 106
<211> LENGTH: 22
<212> TYPE: PRT
<213> ORGANISM: Artificial
<220> FEATURE:
<223> OTHER INFORMATION: Synthetic peptide
```

```
<400> SEQUENCE: 106

Ser Ala Gly Ser Glu Gln Gln Leu Asp Gln Leu Leu Leu Met Phe Ile
1               5                   10                  15

Met Glu Met Leu Gln Gln
            20

<210> SEQ ID NO 107
<211> LENGTH: 22
<212> TYPE: PRT
<213> ORGANISM: Artificial
<220> FEATURE:
<223> OTHER INFORMATION: Synthetic peptide

<400> SEQUENCE: 107

Ser Ala Gly Ser Glu Gln Gln Leu Asp Gln Leu Leu Leu Met Phe Ile
1               5                   10                  15

Met Met Glu Leu Gln Gln
            20

<210> SEQ ID NO 108
<211> LENGTH: 22
<212> TYPE: PRT
<213> ORGANISM: Artificial
<220> FEATURE:
<223> OTHER INFORMATION: Synthetic peptide

<400> SEQUENCE: 108

Ser Ala Gly Ser Glu Gln Gln Leu Asp Gln Leu Leu Leu Met Phe Ile
1               5                   10                  15

Met Met Met Glu Gln Gln
            20

<210> SEQ ID NO 109
<211> LENGTH: 22
<212> TYPE: PRT
<213> ORGANISM: Artificial
<220> FEATURE:
<223> OTHER INFORMATION: Synthetic peptide

<400> SEQUENCE: 109

Ser Ala Gly Ser Glu Gln Gln Leu Lys Gln Leu Leu Leu Met Phe Ile
1               5                   10                  15

Met Met Met Leu Gln Gln
            20

<210> SEQ ID NO 110
<211> LENGTH: 22
<212> TYPE: PRT
<213> ORGANISM: Artificial
<220> FEATURE:
<223> OTHER INFORMATION: Synthetic peptide

<400> SEQUENCE: 110

Ser Ala Gly Ser Glu Gln Gln Leu Asp Glu Leu Leu Leu Met Phe Ile
1               5                   10                  15

Met Met Met Leu Gln Gln
            20

<210> SEQ ID NO 111
<211> LENGTH: 22
<212> TYPE: PRT
<213> ORGANISM: Artificial
<220> FEATURE:
```

<223> OTHER INFORMATION: Synthetic peptide

<400> SEQUENCE: 111

Ser Ala Gly Ser Glu Gln Gln Leu Asp Ser Leu Leu Leu Met Phe Ile
1               5                   10                  15
Met Met Met Leu Gln Gln
            20

<210> SEQ ID NO 112
<211> LENGTH: 22
<212> TYPE: PRT
<213> ORGANISM: Artificial
<220> FEATURE:
<223> OTHER INFORMATION: Synthetic peptide

<400> SEQUENCE: 112

Ser Ala Gly Ser Glu Gln Gln Leu Asp Ala Leu Leu Leu Met Phe Ile
1               5                   10                  15
Met Met Met Leu Gln Gln
            20

<210> SEQ ID NO 113
<211> LENGTH: 22
<212> TYPE: PRT
<213> ORGANISM: Artificial
<220> FEATURE:
<223> OTHER INFORMATION: Synthetic peptide

<400> SEQUENCE: 113

Ser Ala Gly Ser Glu Ser Ser Leu Asp Gln Leu Leu Leu Met Phe Ile
1               5                   10                  15
Met Met Met Leu Gln Gln
            20

<210> SEQ ID NO 114
<211> LENGTH: 22
<212> TYPE: PRT
<213> ORGANISM: Artificial
<220> FEATURE:
<223> OTHER INFORMATION: Synthetic peptide

<400> SEQUENCE: 114

Ser Ala Gly Ser Glu Gln Gln Leu Asp Gln Leu Leu Leu Met Phe Ile
1               5                   10                  15
Met Met Met Leu Ser Ser
            20

<210> SEQ ID NO 115
<211> LENGTH: 22
<212> TYPE: PRT
<213> ORGANISM: Artificial
<220> FEATURE:
<223> OTHER INFORMATION: Synthetic peptide

<400> SEQUENCE: 115

Ser Ala Gly Ser Glu Gly Gly Leu Asp Gln Leu Leu Leu Met Phe Ile
1               5                   10                  15
Met Met Met Leu Gln Gln
            20

<210> SEQ ID NO 116
<211> LENGTH: 22
<212> TYPE: PRT
<213> ORGANISM: Artificial

```
<220> FEATURE:
<223> OTHER INFORMATION: Synthetic peptide

<400> SEQUENCE: 116

Ser Ala Gly Ser Glu Gln Gln Leu Asp Gln Leu Leu Leu Met Phe Ile
1               5                   10                  15

Met Met Met Leu Gly Gly
            20

<210> SEQ ID NO 117
<211> LENGTH: 22
<212> TYPE: PRT
<213> ORGANISM: Artificial
<220> FEATURE:
<223> OTHER INFORMATION: Synthetic peptide

<400> SEQUENCE: 117

Ser Ala Gly Ser Glu Gln Gln Val Asp Gln Leu Leu Leu Met Phe Ile
1               5                   10                  15

Met Met Met Leu Gln Gln
            20

<210> SEQ ID NO 118
<211> LENGTH: 22
<212> TYPE: PRT
<213> ORGANISM: Artificial
<220> FEATURE:
<223> OTHER INFORMATION: Synthetic peptide

<400> SEQUENCE: 118

Ser Ala Gly Ser Glu Gln Gln Leu Asp Gln Val Leu Leu Met Phe Ile
1               5                   10                  15

Met Met Met Leu Gln Gln
            20

<210> SEQ ID NO 119
<211> LENGTH: 22
<212> TYPE: PRT
<213> ORGANISM: Artificial
<220> FEATURE:
<223> OTHER INFORMATION: Synthetic peptide

<400> SEQUENCE: 119

Ser Ala Gly Ser Glu Gln Gln Leu Asp Gln Leu Val Leu Met Phe Ile
1               5                   10                  15

Met Met Met Leu Gln Gln
            20

<210> SEQ ID NO 120
<211> LENGTH: 22
<212> TYPE: PRT
<213> ORGANISM: Artificial
<220> FEATURE:
<223> OTHER INFORMATION: Synthetic peptide

<400> SEQUENCE: 120

Ser Ala Gly Ser Glu Gln Gln Leu Asp Gln Leu Leu Val Met Phe Ile
1               5                   10                  15

Met Met Met Leu Gln Gln
            20

<210> SEQ ID NO 121
<211> LENGTH: 22
<212> TYPE: PRT
```

<213> ORGANISM: Artificial
<220> FEATURE:
<223> OTHER INFORMATION: Synthetic peptide

<400> SEQUENCE: 121

Ser Ala Gly Ser Glu Gln Gln Leu Asp Gln Leu Leu Leu Val Phe Ile
1               5                   10                  15

Met Met Met Leu Gln Gln
            20

<210> SEQ ID NO 122
<211> LENGTH: 22
<212> TYPE: PRT
<213> ORGANISM: Artificial
<220> FEATURE:
<223> OTHER INFORMATION: Synthetic peptide

<400> SEQUENCE: 122

Ser Ala Gly Ser Glu Gln Gln Leu Asp Gln Leu Leu Leu Met Val Ile
1               5                   10                  15

Met Met Met Leu Gln Gln
            20

<210> SEQ ID NO 123
<211> LENGTH: 22
<212> TYPE: PRT
<213> ORGANISM: Artificial
<220> FEATURE:
<223> OTHER INFORMATION: Synthetic peptide

<400> SEQUENCE: 123

Ser Ala Gly Ser Glu Gln Gln Leu Asp Gln Leu Leu Leu Met Phe Val
1               5                   10                  15

Met Met Met Leu Gln Gln
            20

<210> SEQ ID NO 124
<211> LENGTH: 22
<212> TYPE: PRT
<213> ORGANISM: Artificial
<220> FEATURE:
<223> OTHER INFORMATION: Synthetic peptide

<400> SEQUENCE: 124

Ser Ala Gly Ser Glu Gln Gln Leu Asp Gln Leu Leu Leu Met Phe Ile
1               5                   10                  15

Val Met Met Leu Gln Gln
            20

<210> SEQ ID NO 125
<211> LENGTH: 22
<212> TYPE: PRT
<213> ORGANISM: Artificial
<220> FEATURE:
<223> OTHER INFORMATION: Synthetic peptide

<400> SEQUENCE: 125

Ser Ala Gly Ser Glu Gln Gln Leu Asp Gln Leu Leu Leu Met Phe Ile
1               5                   10                  15

Met Val Met Leu Gln Gln
            20

<210> SEQ ID NO 126
<211> LENGTH: 22

```
<212> TYPE: PRT
<213> ORGANISM: Artificial
<220> FEATURE:
<223> OTHER INFORMATION: Synthetic peptide

<400> SEQUENCE: 126

Ser Ala Gly Ser Glu Gln Gln Leu Asp Gln Leu Leu Leu Met Phe Ile
1               5                   10                  15

Met Met Val Leu Gln Gln
            20

<210> SEQ ID NO 127
<211> LENGTH: 22
<212> TYPE: PRT
<213> ORGANISM: Artificial
<220> FEATURE:
<223> OTHER INFORMATION: Synthetic peptide

<400> SEQUENCE: 127

Ser Ala Gly Ser Glu Gln Gln Leu Asp Gln Leu Leu Leu Met Phe Ile
1               5                   10                  15

Met Met Met Val Gln Gln
            20

<210> SEQ ID NO 128
<211> LENGTH: 20
<212> TYPE: PRT
<213> ORGANISM: Artificial
<220> FEATURE:
<223> OTHER INFORMATION: Synthetic peptide

<400> SEQUENCE: 128

Ser Ala Gly Ser Glu Gln Gln Leu Asp Gln Leu Leu Leu Met Phe Ile
1               5                   10                  15

Met Met Met Leu
            20

<210> SEQ ID NO 129
<211> LENGTH: 15
<212> TYPE: PRT
<213> ORGANISM: Artificial
<220> FEATURE:
<223> OTHER INFORMATION: Synthetic peptide

<400> SEQUENCE: 129

Gln Gln Leu Asp Gln Leu Leu Leu Met Phe Ile Met Met Met Leu
1               5                   10                  15

<210> SEQ ID NO 130
<211> LENGTH: 22
<212> TYPE: PRT
<213> ORGANISM: Artificial
<220> FEATURE:
<223> OTHER INFORMATION: Synthetic peptide

<400> SEQUENCE: 130

Ser Ala Gly Ser Glu Gln Gln Leu Asp Gln Leu Leu Leu Ala Phe Ile
1               5                   10                  15

Ala Ala Ala Leu Gln Gln
            20

<210> SEQ ID NO 131
<211> LENGTH: 22
<212> TYPE: PRT
<213> ORGANISM: Artificial
```

```
<220> FEATURE:
<223> OTHER INFORMATION: Synthetic peptide

<400> SEQUENCE: 131

Ser Ala Gly Ser Glu Gln Gln Leu Asp Gln Leu Leu Glu Phe Ile
1               5                   10                  15

Glu Glu Glu Leu Gln Gln
            20

<210> SEQ ID NO 132
<211> LENGTH: 16
<212> TYPE: PRT
<213> ORGANISM: Artificial
<220> FEATURE:
<223> OTHER INFORMATION: Synthetic peptide

<400> SEQUENCE: 132

Gln Gln Leu Asp Leu Leu Leu Met Phe Ile Met Met Met Leu Gln Gln
1               5                   10                  15

<210> SEQ ID NO 133
<211> LENGTH: 14
<212> TYPE: PRT
<213> ORGANISM: Artificial
<220> FEATURE:
<223> OTHER INFORMATION: Synthetic peptide

<400> SEQUENCE: 133

Leu Asp Leu Leu Leu Met Phe Ile Met Met Met Leu Gln Gln
1               5                   10

<210> SEQ ID NO 134
<211> LENGTH: 19
<212> TYPE: PRT
<213> ORGANISM: Artificial
<220> FEATURE:
<223> OTHER INFORMATION: Synthetic peptide

<400> SEQUENCE: 134

Ser Ala Gly Ser Glu Gln Gln Leu Asp Leu Leu Leu Met Phe Ile Met
1               5                   10                  15

Met Met Leu

<210> SEQ ID NO 135
<211> LENGTH: 15
<212> TYPE: PRT
<213> ORGANISM: Artificial
<220> FEATURE:
<223> OTHER INFORMATION: Synthetic peptide

<400> SEQUENCE: 135

Gln Gln Leu Asp Leu Leu Leu Met Phe Ile Ile Met Met Met Leu
1               5                   10                  15

<210> SEQ ID NO 136
<211> LENGTH: 12
<212> TYPE: PRT
<213> ORGANISM: Artificial
<220> FEATURE:
<223> OTHER INFORMATION: Synthetic peptide

<400> SEQUENCE: 136

Leu Asp Leu Leu Leu Met Phe Ile Met Met Met Leu
1               5                   10
```

```
<210> SEQ ID NO 137
<211> LENGTH: 21
<212> TYPE: PRT
<213> ORGANISM: Artificial
<220> FEATURE:
<223> OTHER INFORMATION: Synthetic peptide

<400> SEQUENCE: 137

Ser Ala Gly Ser Glu Gln Gln Leu Asp Leu Leu Glu Phe Ile Glu
1               5                   10                  15

Glu Glu Leu Gln Gln
            20

<210> SEQ ID NO 138
<211> LENGTH: 23
<212> TYPE: PRT
<213> ORGANISM: Artificial
<220> FEATURE:
<223> OTHER INFORMATION: Synthetic peptide

<400> SEQUENCE: 138

His His His His His His Arg Gln Gln Leu Asp Leu Leu Leu Ala Phe
1               5                   10                  15

Ile Ala Ala Ala Leu Gln Gln
            20

<210> SEQ ID NO 139
<211> LENGTH: 15
<212> TYPE: PRT
<213> ORGANISM: Artificial
<220> FEATURE:
<223> OTHER INFORMATION: Synthetic peptide

<400> SEQUENCE: 139

Gln Leu Glu Leu Leu Leu Ala Phe Ile Ala Ala Ala Leu Gln Gln
1               5                   10                  15

<210> SEQ ID NO 140
<211> LENGTH: 19
<212> TYPE: PRT
<213> ORGANISM: Artificial
<220> FEATURE:
<223> OTHER INFORMATION: Synthetic peptide

<400> SEQUENCE: 140

Ser Ala Gly Ser Glu Gln Gln Leu Asp Leu Leu Leu Ala Phe Ile Ala
1               5                   10                  15

Ala Ala Leu

<210> SEQ ID NO 141
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E

<400> SEQUENCE: 141

Leu Asp Leu Leu Leu Xaa Phe Ile Met Met Met Leu
1               5                   10

<210> SEQ ID NO 142
<211> LENGTH: 12
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E

<400> SEQUENCE: 142

Leu Asp Leu Leu Leu Met Phe Ile Xaa Met Met Leu
1               5                   10

<210> SEQ ID NO 143
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E

<400> SEQUENCE: 143

Leu Asp Leu Leu Leu Met Phe Ile Met Xaa Met Leu
1               5                   10

<210> SEQ ID NO 144
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E

<400> SEQUENCE: 144

Leu Asp Leu Leu Leu Met Phe Ile Met Met Xaa Leu
1               5                   10

<210> SEQ ID NO 145
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E

<400> SEQUENCE: 145

Leu Asp Leu Leu Leu Xaa Phe Ile Xaa Met Met Leu
1               5                   10

<210> SEQ ID NO 146
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
```

```
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 146

Leu Asp Leu Leu Leu Xaa Phe Ile Met Xaa Met Leu
1               5                   10

<210> SEQ ID NO 147
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 147

Leu Asp Leu Leu Leu Xaa Phe Ile Met Met Xaa Leu
1               5                   10

<210> SEQ ID NO 148
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 148

Leu Asp Leu Leu Leu Met Phe Ile Xaa Xaa Met Leu
1               5                   10

<210> SEQ ID NO 149
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 149

Leu Asp Leu Leu Leu Met Phe Ile Xaa Met Xaa Leu
1               5                   10

<210> SEQ ID NO 150
<211> LENGTH: 12
<212> TYPE: PRT
<213> ORGANISM: Artificial
```

```
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 150

Leu Asp Leu Leu Leu Met Phe Ile Met Xaa Xaa Leu
1               5                   10

<210> SEQ ID NO 151
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 151

Leu Asp Leu Leu Leu Met Phe Ile Xaa Xaa Xaa Leu
1               5                   10

<210> SEQ ID NO 152
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 152

Leu Asp Leu Leu Leu Xaa Phe Ile Met Xaa Xaa Leu
1               5                   10

<210> SEQ ID NO 153
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
```

```
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 153

Leu Asp Leu Leu Leu Xaa Phe Ile Xaa Met Xaa Leu
1               5                   10

<210> SEQ ID NO 154
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 154

Leu Asp Leu Leu Leu Xaa Phe Ile Xaa Xaa Met Leu
1               5                   10

<210> SEQ ID NO 155
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 155

Leu Asp Leu Leu Leu Xaa Phe Ile Xaa Xaa Xaa Leu
1               5                   10

<210> SEQ ID NO 156
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E

<400> SEQUENCE: 156
```

```
Leu Asp Gln Leu Leu Leu Xaa Phe Ile Met Met Met Leu
1               5                   10

<210> SEQ ID NO 157
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E

<400> SEQUENCE: 157

Leu Asp Gln Leu Leu Leu Met Phe Ile Xaa Met Met Leu
1               5                   10

<210> SEQ ID NO 158
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E

<400> SEQUENCE: 158

Leu Asp Gln Leu Leu Leu Met Phe Ile Met Xaa Met Leu
1               5                   10

<210> SEQ ID NO 159
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: X at position 12 is A or E

<400> SEQUENCE: 159

Leu Asp Gln Leu Leu Leu Met Phe Ile Met Met Xaa Leu
1               5                   10

<210> SEQ ID NO 160
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 160

Leu Asp Gln Leu Leu Leu Xaa Phe Ile Xaa Met Met Leu
1               5                   10

<210> SEQ ID NO 161
<211> LENGTH: 13
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 161

Leu Asp Gln Leu Leu Leu Xaa Phe Ile Met Xaa Met Leu
1               5                   10

<210> SEQ ID NO 162
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 162

Leu Asp Gln Leu Leu Leu Xaa Phe Ile Met Met Xaa Leu
1               5                   10

<210> SEQ ID NO 163
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 163

Leu Asp Gln Leu Leu Leu Met Phe Ile Xaa Xaa Met Leu
1               5                   10

<210> SEQ ID NO 164
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 164

Leu Asp Gln Leu Leu Leu Met Phe Ile Xaa Met Xaa Leu
```

```
1               5                   10
```

<210> SEQ ID NO 165
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 165

```
Leu Asp Gln Leu Leu Leu Met Phe Ile Met Xaa Xaa Leu
1               5                   10
```

<210> SEQ ID NO 166
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 166

```
Leu Asp Gln Leu Leu Leu Met Phe Ile Xaa Xaa Xaa Leu
1               5                   10
```

<210> SEQ ID NO 167
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 167

```
Leu Asp Gln Leu Leu Leu Xaa Phe Ile Met Xaa Xaa Leu
1               5                   10
```

<210> SEQ ID NO 168
<211> LENGTH: 13
<212> TYPE: PRT
<213> ORGANISM: Artificial
<220> FEATURE:

```
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 168

Leu Asp Gln Leu Leu Leu Xaa Phe Ile Xaa Met Xaa Leu
1               5                   10

<210> SEQ ID NO 169
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 169

Leu Asp Gln Leu Leu Leu Xaa Phe Ile Xaa Xaa Met Leu
1               5                   10

<210> SEQ ID NO 170
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 170

Leu Asp Gln Leu Leu Leu Xaa Phe Ile Xaa Xaa Xaa Leu
1               5                   10

<210> SEQ ID NO 171
<211> LENGTH: 12
<212> TYPE: PRT
<213> ORGANISM: Artificial
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V

<400> SEQUENCE: 171

Xaa Asp Leu Leu Leu Met Phe Ile Met Met Met Leu
1               5                   10

<210> SEQ ID NO 172
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (6)..(6)
<223> OTHER INFORMATION: X at position 6 is A or E

<400> SEQUENCE: 172

Xaa Asp Leu Leu Leu Xaa Phe Ile Met Met Met Leu
1               5                   10

<210> SEQ ID NO 173
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 173

Xaa Asp Leu Leu Leu Met Phe Ile Xaa Met Met Leu
1               5                   10

<210> SEQ ID NO 174
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 174

Xaa Asp Leu Leu Leu Met Phe Ile Met Xaa Met Leu
1               5                   10

<210> SEQ ID NO 175
<211> LENGTH: 12
<212> TYPE: PRT
<213> ORGANISM: Artificial
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 175

Xaa Asp Leu Leu Leu Met Phe Ile Met Met Xaa Leu
1               5                   10

<210> SEQ ID NO 176
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E

<400> SEQUENCE: 176

Xaa Asp Leu Leu Leu Xaa Phe Ile Xaa Met Met Leu
1               5                   10

<210> SEQ ID NO 177
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 177

Xaa Asp Leu Leu Leu Xaa Phe Ile Met Xaa Met Leu
1               5                   10

<210> SEQ ID NO 178
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
```

```
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 178

Xaa Asp Leu Leu Leu Xaa Phe Ile Met Met Xaa Leu
1               5                   10

<210> SEQ ID NO 179
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 179

Xaa Asp Leu Leu Leu Met Phe Ile Xaa Xaa Met Leu
1               5                   10

<210> SEQ ID NO 180
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 180

Xaa Asp Leu Leu Leu Met Phe Ile Xaa Met Xaa Leu
1               5                   10

<210> SEQ ID NO 181
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
```

<222> LOCATION: (11)..(11)
<223> OTHER INFORMATION: X at position 11 is A or E

<400> SEQUENCE: 181

Xaa Asp Leu Leu Leu Met Phe Ile Met Xaa Xaa Leu
1               5                   10

<210> SEQ ID NO 182
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 182

Xaa Asp Leu Leu Leu Met Phe Ile Xaa Xaa Xaa Leu
1               5                   10

<210> SEQ ID NO 183
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 183

Xaa Asp Leu Leu Leu Xaa Phe Ile Met Xaa Xaa Leu
1               5                   10

<210> SEQ ID NO 184
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE

```
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 184

Xaa Asp Leu Leu Leu Xaa Phe Ile Xaa Met Xaa Leu
1               5                   10

<210> SEQ ID NO 185
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 185

Xaa Asp Leu Leu Leu Xaa Phe Ile Xaa Xaa Met Leu
1               5                   10

<210> SEQ ID NO 186
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 186

Xaa Asp Leu Leu Leu Xaa Phe Ile Xaa Xaa Xaa Leu
1               5                   10
```

```
<210> SEQ ID NO 187
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V

<400> SEQUENCE: 187

Xaa Asp Gln Leu Leu Leu Met Phe Ile Met Met Met Leu
 1               5                  10

<210> SEQ ID NO 188
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E

<400> SEQUENCE: 188

Xaa Asp Gln Leu Leu Leu Xaa Phe Ile Met Met Met Leu
 1               5                  10

<210> SEQ ID NO 189
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 189

Xaa Asp Gln Leu Leu Leu Met Phe Ile Xaa Met Met Leu
 1               5                  10

<210> SEQ ID NO 190
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 190

Xaa Asp Gln Leu Leu Leu Met Phe Ile Met Xaa Met Leu
 1               5                  10
```

```
<210> SEQ ID NO 191
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 191

Xaa Asp Gln Leu Leu Leu Met Phe Ile Met Met Xaa Leu
1               5                   10

<210> SEQ ID NO 192
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 192

Xaa Asp Gln Leu Leu Leu Xaa Phe Ile Xaa Met Met Leu
1               5                   10

<210> SEQ ID NO 193
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 193

Xaa Asp Gln Leu Leu Leu Xaa Phe Ile Met Xaa Met Leu
1               5                   10

<210> SEQ ID NO 194
<211> LENGTH: 13
<212> TYPE: PRT
<213> ORGANISM: Artificial
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 194

Xaa Asp Gln Leu Leu Leu Xaa Phe Ile Met Met Xaa Leu
1               5                   10

<210> SEQ ID NO 195
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 195

Xaa Asp Gln Leu Leu Leu Met Phe Ile Xaa Xaa Met Leu
1               5                   10

<210> SEQ ID NO 196
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 196

Xaa Asp Gln Leu Leu Leu Met Phe Ile Xaa Met Xaa Leu
1               5                   10

<210> SEQ ID NO 197
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
```

```
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 197

Xaa Asp Gln Leu Leu Leu Met Phe Ile Met Xaa Xaa Leu
1               5                   10

<210> SEQ ID NO 198
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 198

Xaa Asp Gln Leu Leu Leu Met Phe Ile Xaa Xaa Xaa Leu
1               5                   10

<210> SEQ ID NO 199
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 199

Xaa Asp Gln Leu Leu Leu Xaa Phe Ile Met Xaa Xaa Leu
1               5                   10

<210> SEQ ID NO 200
<211> LENGTH: 13
<212> TYPE: PRT
<213> ORGANISM: Artificial
<220> FEATURE:
<223> OTHER INFORMATION: Synthetic peptide
<220> FEATURE:
```

<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 200

Xaa Asp Gln Leu Leu Leu Xaa Phe Ile Xaa Met Xaa Leu
1               5                   10

<210> SEQ ID NO 201
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 201

Xaa Asp Gln Leu Leu Leu Xaa Phe Ile Xaa Xaa Met Leu
1               5                   10

<210> SEQ ID NO 202
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X at position 1 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 202

```
Xaa Asp Gln Leu Leu Leu Xaa Phe Ile Xaa Xaa Xaa Leu
1               5                   10

<210> SEQ ID NO 203
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V

<400> SEQUENCE: 203

Leu Asp Xaa Leu Leu Met Phe Ile Met Met Met Leu
1               5                   10

<210> SEQ ID NO 204
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E

<400> SEQUENCE: 204

Leu Asp Xaa Leu Leu Xaa Phe Ile Met Met Met Leu
1               5                   10

<210> SEQ ID NO 205
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 205

Leu Asp Xaa Leu Leu Met Phe Ile Xaa Met Met Leu
1               5                   10

<210> SEQ ID NO 206
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (10)..(10)
<223> OTHER INFORMATION: X at position 10 is A or E
```

```
<400> SEQUENCE: 206

Leu Asp Xaa Leu Leu Met Phe Ile Met Xaa Met Leu
1               5                   10

<210> SEQ ID NO 207
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 207

Leu Asp Xaa Leu Leu Met Phe Ile Met Met Xaa Leu
1               5                   10

<210> SEQ ID NO 208
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E

<400> SEQUENCE: 208

Leu Asp Xaa Leu Leu Xaa Phe Ile Xaa Met Met Leu
1               5                   10

<210> SEQ ID NO 209
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 209

Leu Asp Xaa Leu Leu Xaa Phe Ile Met Xaa Met Leu
1               5                   10

<210> SEQ ID NO 210
<211> LENGTH: 12
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 210

Leu Asp Xaa Leu Leu Xaa Phe Ile Met Met Xaa Leu
1               5                   10

<210> SEQ ID NO 211
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 211

Leu Asp Xaa Leu Leu Met Phe Ile Xaa Xaa Met Leu
1               5                   10

<210> SEQ ID NO 212
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 212

Leu Asp Xaa Leu Leu Met Phe Ile Xaa Met Xaa Leu
1               5                   10

<210> SEQ ID NO 213
<211> LENGTH: 12
<212> TYPE: PRT
<213> ORGANISM: Artificial
<220> FEATURE:
<223> OTHER INFORMATION: Synthetic peptide
```

-continued

```
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 213

Leu Asp Xaa Leu Leu Met Phe Ile Met Xaa Xaa Leu
1               5                   10

<210> SEQ ID NO 214
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 214

Leu Asp Xaa Leu Leu Met Phe Ile Xaa Xaa Xaa Leu
1               5                   10

<210> SEQ ID NO 215
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 215

Leu Asp Xaa Leu Leu Xaa Phe Ile Met Xaa Xaa Leu
1               5                   10

<210> SEQ ID NO 216
<211> LENGTH: 12
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 216

Leu Asp Xaa Leu Leu Xaa Phe Ile Xaa Met Xaa Leu
1               5                   10

<210> SEQ ID NO 217
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 217

Leu Asp Xaa Leu Leu Xaa Phe Ile Xaa Xaa Met Leu
1               5                   10

<210> SEQ ID NO 218
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
```

```
<221> NAME/KEY: MISC_FEATURE
<222> LOCATION: (11)..(11)
<223> OTHER INFORMATION: X at position 11 is A or E

<400> SEQUENCE: 218

Leu Asp Xaa Leu Leu Xaa Phe Ile Xaa Xaa Xaa Leu
1               5                   10

<210> SEQ ID NO 219
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V

<400> SEQUENCE: 219

Leu Asp Gln Xaa Leu Leu Met Phe Ile Met Met Met Leu
1               5                   10

<210> SEQ ID NO 220
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E

<400> SEQUENCE: 220

Leu Asp Gln Xaa Leu Leu Xaa Phe Ile Met Met Met Leu
1               5                   10

<210> SEQ ID NO 221
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 221

Leu Asp Gln Xaa Leu Leu Met Phe Ile Xaa Met Met Leu
1               5                   10

<210> SEQ ID NO 222
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
```

```
<220> FEATURE:
<221> NAME/KEY: MISC_FEATURE
<222> LOCATION: (11)..(11)
<223> OTHER INFORMATION: X at position 11 is A or E

<400> SEQUENCE: 222

Leu Asp Gln Xaa Leu Leu Met Phe Ile Met Xaa Met Leu
1               5                   10

<210> SEQ ID NO 223
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 223

Leu Asp Gln Xaa Leu Leu Met Phe Ile Met Met Xaa Leu
1               5                   10

<210> SEQ ID NO 224
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 224

Leu Asp Gln Xaa Leu Leu Xaa Phe Ile Xaa Met Met Leu
1               5                   10

<210> SEQ ID NO 225
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 225

Leu Asp Gln Xaa Leu Leu Xaa Phe Ile Met Xaa Met Leu
```

```
<210> SEQ ID NO 226
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 226

Leu Asp Gln Xaa Leu Leu Xaa Phe Ile Met Met Xaa Leu
1               5                   10

<210> SEQ ID NO 227
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 227

Leu Asp Gln Xaa Leu Leu Met Phe Ile Xaa Xaa Met Leu
1               5                   10

<210> SEQ ID NO 228
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 228

Leu Asp Gln Xaa Leu Leu Met Phe Ile Xaa Met Xaa Leu
1               5                   10

<210> SEQ ID NO 229
```

```
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 229

Leu Asp Gln Xaa Leu Leu Met Phe Ile Met Xaa Xaa Leu
1               5                   10

<210> SEQ ID NO 230
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 230

Leu Asp Gln Xaa Leu Leu Met Phe Ile Xaa Xaa Xaa Leu
1               5                   10

<210> SEQ ID NO 231
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 231

Leu Asp Gln Xaa Leu Leu Xaa Phe Ile Met Xaa Xaa Leu
```

```
1               5                   10

<210> SEQ ID NO 232
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 232

Leu Asp Gln Xaa Leu Leu Xaa Phe Ile Xaa Met Xaa Leu
1               5                   10

<210> SEQ ID NO 233
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 233

Leu Asp Gln Xaa Leu Leu Xaa Phe Ile Xaa Xaa Met Leu
1               5                   10

<210> SEQ ID NO 234
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
```

```
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 234

Leu Asp Gln Xaa Leu Leu Xaa Phe Ile Xaa Xaa Xaa Leu
1               5                   10

<210> SEQ ID NO 235
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V

<400> SEQUENCE: 235

Leu Asp Leu Xaa Leu Met Phe Ile Met Met Met Leu
1               5                   10

<210> SEQ ID NO 236
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (6)..(6)
<223> OTHER INFORMATION: X at position 6 is A or E

<400> SEQUENCE: 236

Leu Asp Leu Xaa Leu Xaa Phe Ile Met Met Met Leu
1               5                   10

<210> SEQ ID NO 237
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 237

Leu Asp Leu Xaa Leu Met Phe Ile Xaa Met Met Leu
1               5                   10

<210> SEQ ID NO 238
<211> LENGTH: 12
<212> TYPE: PRT
<213> ORGANISM: Artificial
<220> FEATURE:
```

<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 238

Leu Asp Leu Xaa Leu Met Phe Ile Met Xaa Met Leu
1               5                   10

<210> SEQ ID NO 239
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 239

Leu Asp Leu Xaa Leu Met Phe Ile Met Met Xaa Leu
1               5                   10

<210> SEQ ID NO 240
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E

<400> SEQUENCE: 240

Leu Asp Leu Xaa Leu Xaa Phe Ile Xaa Met Met Leu
1               5                   10

<210> SEQ ID NO 241
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)

```
<223> OTHER INFORMATION: X at position 10 is A or E

<400> SEQUENCE: 241

Leu Asp Leu Xaa Leu Xaa Phe Ile Met Xaa Met Leu
1               5                   10

<210> SEQ ID NO 242
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 242

Leu Asp Leu Xaa Leu Xaa Phe Ile Met Met Xaa Leu
1               5                   10

<210> SEQ ID NO 243
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 243

Leu Asp Leu Xaa Leu Met Phe Ile Xaa Xaa Met Leu
1               5                   10

<210> SEQ ID NO 244
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 244
```

```
Leu Asp Leu Xaa Leu Met Phe Ile Xaa Met Xaa Leu
1               5                   10
```

<210> SEQ ID NO 245
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 245

```
Leu Asp Leu Xaa Leu Met Phe Ile Met Xaa Xaa Leu
1               5                   10
```

<210> SEQ ID NO 246
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 246

```
Leu Asp Leu Xaa Leu Met Phe Ile Xaa Xaa Xaa Leu
1               5                   10
```

<210> SEQ ID NO 247
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)

```
<223> OTHER INFORMATION: X at position 12 is A or E

<400> SEQUENCE: 247

Leu Asp Leu Xaa Leu Leu Xaa Phe Ile Met Xaa Xaa Leu
1               5                   10

<210> SEQ ID NO 248
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 248

Leu Asp Leu Xaa Leu Leu Xaa Phe Ile Xaa Met Xaa Leu
1               5                   10

<210> SEQ ID NO 249
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 249

Leu Asp Leu Xaa Leu Leu Xaa Phe Ile Xaa Xaa Met Leu
1               5                   10

<210> SEQ ID NO 250
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X at position 4 is E or V
<220> FEATURE:
<221> NAME/KEY: MISC_FEATURE
<222> LOCATION: (6)..(6)
```

```
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 250

Leu Asp Leu Xaa Leu Xaa Phe Ile Xaa Xaa Xaa Leu
1               5                   10

<210> SEQ ID NO 251
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V

<400> SEQUENCE: 251

Leu Asp Gln Leu Xaa Leu Met Phe Ile Met Met Met Leu
1               5                   10

<210> SEQ ID NO 252
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (7)..(7)
<223> OTHER INFORMATION: X at position 7 is A or E

<400> SEQUENCE: 252

Leu Asp Gln Leu Xaa Leu Xaa Phe Ile Met Met Met Leu
1               5                   10

<210> SEQ ID NO 253
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 253

Leu Asp Gln Leu Xaa Leu Met Phe Ile Xaa Met Met Leu
1               5                   10
```

```
<210> SEQ ID NO 254
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 254

Leu Asp Gln Leu Xaa Leu Met Phe Ile Met Xaa Met Leu
1               5                   10

<210> SEQ ID NO 255
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 255

Leu Asp Gln Leu Xaa Leu Met Phe Ile Met Met Xaa Leu
1               5                   10

<210> SEQ ID NO 256
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 256

Leu Asp Gln Leu Xaa Leu Xaa Phe Ile Xaa Met Met Leu
1               5                   10

<210> SEQ ID NO 257
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
```

```
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 257

Leu Asp Gln Leu Xaa Leu Xaa Phe Ile Met Xaa Met Leu
1               5                   10

<210> SEQ ID NO 258
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 258

Leu Asp Gln Leu Xaa Leu Xaa Phe Ile Met Met Xaa Leu
1               5                   10

<210> SEQ ID NO 259
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 259

Leu Asp Gln Leu Xaa Leu Met Phe Ile Xaa Xaa Met Leu
1               5                   10

<210> SEQ ID NO 260
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
```

-continued

```
<222> LOCATION: (12)..(12)
<223> OTHER INFORMATION: X at position 12 is A or E

<400> SEQUENCE: 260

Leu Asp Gln Leu Xaa Leu Met Phe Ile Xaa Met Xaa Leu
1               5                   10

<210> SEQ ID NO 261
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 261

Leu Asp Gln Leu Xaa Leu Met Phe Ile Met Xaa Xaa Leu
1               5                   10

<210> SEQ ID NO 262
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 262

Leu Asp Gln Leu Xaa Leu Met Phe Ile Xaa Xaa Xaa Leu
1               5                   10

<210> SEQ ID NO 263
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (8)..(8)
<223> OTHER INFORMATION: X at position 8 is A or E
<220> FEATURE:
<221> NAME/KEY: MISC_FEATURE
```

<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is A or E

<400> SEQUENCE: 263

Leu Asp Gln Leu Xaa Leu Leu Xaa Phe Ile Met Xaa Xaa Leu
1               5                   10

<210> SEQ ID NO 264
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (8)..(8)
<223> OTHER INFORMATION: X at position 8 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is A or E

<400> SEQUENCE: 264

Leu Asp Gln Leu Xaa Leu Leu Xaa Phe Ile Xaa Met Xaa Leu
1               5                   10

<210> SEQ ID NO 265
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (8)..(8)
<223> OTHER INFORMATION: X at position 8 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 265

Leu Asp Gln Leu Xaa Leu Leu Xaa Phe Ile Xaa Xaa Met Leu
1               5                   10

<210> SEQ ID NO 266
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE

```
<222> LOCATION: (5)..(5)
<223> OTHER INFORMATION: X at position 5 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 266

Leu Asp Gln Leu Xaa Leu Xaa Phe Ile Xaa Xaa Xaa Leu
1               5                   10

<210> SEQ ID NO 267
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V

<400> SEQUENCE: 267

Leu Asp Leu Leu Xaa Met Phe Ile Met Met Met Leu
1               5                   10

<210> SEQ ID NO 268
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (6)..(6)
<223> OTHER INFORMATION: X at position 6 is A or E

<400> SEQUENCE: 268

Leu Asp Leu Leu Xaa Xaa Phe Ile Met Met Met Leu
1               5                   10

<210> SEQ ID NO 269
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 269
```

```
Leu Asp Leu Leu Xaa Met Phe Ile Xaa Met Met Leu
1               5                   10

<210> SEQ ID NO 270
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 270

Leu Asp Leu Leu Xaa Met Phe Ile Met Xaa Met Leu
1               5                   10

<210> SEQ ID NO 271
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 271

Leu Asp Leu Leu Xaa Met Phe Ile Met Met Xaa Leu
1               5                   10

<210> SEQ ID NO 272
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E

<400> SEQUENCE: 272

Leu Asp Leu Leu Xaa Xaa Phe Ile Xaa Met Met Leu
1               5                   10

<210> SEQ ID NO 273
<211> LENGTH: 12
<212> TYPE: PRT
<213> ORGANISM: Artificial
<220> FEATURE:
<223> OTHER INFORMATION: Synthetic peptide
<220> FEATURE:
```

```
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 273

Leu Asp Leu Leu Xaa Xaa Phe Ile Met Xaa Met Leu
1               5                   10

<210> SEQ ID NO 274
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 274

Leu Asp Leu Leu Xaa Xaa Phe Ile Met Met Xaa Leu
1               5                   10

<210> SEQ ID NO 275
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 275

Leu Asp Leu Leu Xaa Met Phe Ile Xaa Xaa Met Leu
1               5                   10

<210> SEQ ID NO 276
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
```

```
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 276

Leu Asp Leu Leu Xaa Met Phe Ile Xaa Met Xaa Leu
1               5                   10

<210> SEQ ID NO 277
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 277

Leu Asp Leu Leu Xaa Met Phe Ile Met Xaa Xaa Leu
1               5                   10

<210> SEQ ID NO 278
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 278

Leu Asp Leu Leu Xaa Met Phe Ile Xaa Xaa Xaa Leu
1               5                   10

<210> SEQ ID NO 279
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
```

```
<221> NAME/KEY: MISC_FEATURE
<222> LOCATION: (8)..(8)
<223> OTHER INFORMATION: X at position 8 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is A or E

<400> SEQUENCE: 279

Leu Asp Leu Leu Xaa Leu Leu Xaa Phe Ile Met Xaa Xaa Leu
1               5                   10

<210> SEQ ID NO 280
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (8)..(8)
<223> OTHER INFORMATION: X at position 8 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is A or E

<400> SEQUENCE: 280

Leu Asp Leu Leu Xaa Leu Leu Xaa Phe Ile Xaa Met Xaa Leu
1               5                   10

<210> SEQ ID NO 281
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (8)..(8)
<223> OTHER INFORMATION: X at position 8 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 281

Leu Asp Leu Leu Xaa Leu Leu Xaa Phe Ile Xaa Xaa Met Leu
1               5                   10

<210> SEQ ID NO 282
<211> LENGTH: 12
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X at position 5 is E or V
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 10 is A or E

<400> SEQUENCE: 282

Leu Asp Leu Leu Xaa Xaa Phe Ile Xaa Xaa Xaa Leu
1               5                   10

<210> SEQ ID NO 283
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V

<400> SEQUENCE: 283

Leu Asp Gln Leu Leu Xaa Met Phe Ile Met Met Met Leu
1               5                   10

<210> SEQ ID NO 284
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (7)..(7)
<223> OTHER INFORMATION: X at position 7 is A or E

<400> SEQUENCE: 284

Leu Asp Gln Leu Leu Xaa Xaa Phe Ile Met Met Met Leu
1               5                   10

<210> SEQ ID NO 285
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
```

```
<221> NAME/KEY: MISC_FEATURE
<222> LOCATION: (10)..(10)
<223> OTHER INFORMATION: X at position 10 is A or E

<400> SEQUENCE: 285

Leu Asp Gln Leu Leu Xaa Met Phe Ile Xaa Met Met Leu
1               5                   10

<210> SEQ ID NO 286
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 286

Leu Asp Gln Leu Leu Xaa Met Phe Ile Met Xaa Met Leu
1               5                   10

<210> SEQ ID NO 287
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 287

Leu Asp Gln Leu Leu Xaa Met Phe Ile Met Met Xaa Leu
1               5                   10

<210> SEQ ID NO 288
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 288

Leu Asp Gln Leu Leu Xaa Xaa Phe Ile Xaa Met Met Leu
1               5                   10

<210> SEQ ID NO 289
<211> LENGTH: 13
```

<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 289

Leu Asp Gln Leu Leu Xaa Xaa Phe Ile Met Xaa Met Leu
1               5                   10

<210> SEQ ID NO 290
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 290

Leu Asp Gln Leu Leu Xaa Xaa Phe Ile Met Met Xaa Leu
1               5                   10

<210> SEQ ID NO 291
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 291

Leu Asp Gln Leu Leu Xaa Met Phe Ile Xaa Xaa Met Leu
1               5                   10

<210> SEQ ID NO 292
<211> LENGTH: 13
<212> TYPE: PRT
<213> ORGANISM: Artificial
<220> FEATURE:
<223> OTHER INFORMATION: Synthetic peptide

```
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 292

Leu Asp Gln Leu Leu Xaa Met Phe Ile Xaa Met Xaa Leu
1               5                   10

<210> SEQ ID NO 293
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 293

Leu Asp Gln Leu Leu Xaa Met Phe Ile Met Xaa Xaa Leu
1               5                   10

<210> SEQ ID NO 294
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 294

Leu Asp Gln Leu Leu Xaa Met Phe Ile Xaa Xaa Xaa Leu
1               5                   10

<210> SEQ ID NO 295
<211> LENGTH: 15
<212> TYPE: PRT
<213> ORGANISM: Artificial
<220> FEATURE:
<223> OTHER INFORMATION: Synthetic peptide
```

```
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: 'X at position 9 is A or E
<220> FEATURE:
<221> NAME/KEY: MISC_FEATURE
<222> LOCATION: (13)..(13)
<223> OTHER INFORMATION: 'X at position 13 is A or E
<220> FEATURE:
<221> NAME/KEY: MISC_FEATURE
<222> LOCATION: (14)..(14)
<223> OTHER INFORMATION: 'X at position 14 is A or E

<400> SEQUENCE: 295

Leu Asp Gln Leu Leu Xaa Leu Leu Xaa Phe Ile Met Xaa Xaa Leu
 1               5                  10                  15

<210> SEQ ID NO 296
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (14)..(14)
<223> OTHER INFORMATION: X at position 14 is A or E

<400> SEQUENCE: 296

Leu Asp Gln Leu Leu Xaa Leu Leu Xaa Phe Ile Xaa Met Xaa Leu
 1               5                  10                  15

<210> SEQ ID NO 297
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is A or E

<400> SEQUENCE: 297

Leu Asp Gln Leu Leu Xaa Leu Leu Xaa Phe Ile Xaa Xaa Met Leu
 1               5                  10                  15
```

```
<210> SEQ ID NO 298
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 298

Leu Asp Gln Leu Leu Xaa Xaa Phe Ile Xaa Xaa Xaa Leu
1               5                   10

<210> SEQ ID NO 299
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: 'X at position 6 is E or V

<400> SEQUENCE: 299

Leu Asp Leu Leu Leu Xaa Phe Ile Met Met Met Leu
1               5                   10

<210> SEQ ID NO 300
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 300

Leu Asp Leu Leu Leu Xaa Phe Ile Xaa Met Met Leu
1               5                   10

<210> SEQ ID NO 301
<211> LENGTH: 12
<212> TYPE: PRT
<213> ORGANISM: Artificial
<220> FEATURE:
<223> OTHER INFORMATION: Synthetic peptide
```

```
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 301

Leu Asp Leu Leu Leu Xaa Phe Ile Met Xaa Met Leu
1               5                   10

<210> SEQ ID NO 302
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 302

Leu Asp Leu Leu Leu Xaa Phe Ile Met Met Xaa Leu
1               5                   10

<210> SEQ ID NO 303
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 303

Leu Asp Leu Leu Leu Xaa Phe Ile Xaa Xaa Met Leu
1               5                   10

<210> SEQ ID NO 304
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E
```

<400> SEQUENCE: 304

Leu Asp Leu Leu Leu Xaa Phe Ile Xaa Met Xaa Leu
1               5                   10

<210> SEQ ID NO 305
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 305

Leu Asp Leu Leu Leu Xaa Phe Ile Met Xaa Xaa Leu
1               5                   10

<210> SEQ ID NO 306
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 306

Leu Asp Leu Leu Leu Xaa Phe Ile Xaa Xaa Xaa Leu
1               5                   10

<210> SEQ ID NO 307
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V

<400> SEQUENCE: 307

Leu Asp Gln Leu Leu Leu Xaa Phe Ile Met Met Met Leu
1               5                   10

<210> SEQ ID NO 308

```
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 308

Leu Asp Gln Leu Leu Leu Xaa Phe Ile Xaa Met Met Leu
1               5                   10

<210> SEQ ID NO 309
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 309

Leu Asp Gln Leu Leu Leu Xaa Phe Ile Met Xaa Met Leu
1               5                   10

<210> SEQ ID NO 310
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 310

Leu Asp Gln Leu Leu Leu Xaa Phe Ile Met Met Xaa Leu
1               5                   10

<210> SEQ ID NO 311
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
```

```
<223> OTHER INFORMATION: X at position 11 is A or E

<400> SEQUENCE: 311

Leu Asp Gln Leu Leu Leu Xaa Phe Ile Xaa Xaa Met Leu
1               5                   10

<210> SEQ ID NO 312
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 312

Leu Asp Gln Leu Leu Leu Xaa Phe Ile Xaa Met Xaa Leu
1               5                   10

<210> SEQ ID NO 313
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 313

Leu Asp Gln Leu Leu Leu Xaa Phe Ile Met Xaa Xaa Leu
1               5                   10

<210> SEQ ID NO 314
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
```

```
<223> OTHER INFORMATION: X at position 12 is A or E

<400> SEQUENCE: 314

Leu Asp Gln Leu Leu Leu Xaa Phe Ile Xaa Xaa Xaa Leu
1               5                   10

<210> SEQ ID NO 315
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V

<400> SEQUENCE: 315

Leu Asp Leu Leu Leu Met Xaa Ile Met Met Met Leu
1               5                   10

<210> SEQ ID NO 316
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V

<400> SEQUENCE: 316

Leu Asp Leu Leu Leu Xaa Xaa Ile Met Met Met Leu
1               5                   10

<210> SEQ ID NO 317
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 317

Leu Asp Leu Leu Leu Met Xaa Ile Xaa Met Met Leu
1               5                   10

<210> SEQ ID NO 318
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
```

```
<222> LOCATION: (10)..(10)
<223> OTHER INFORMATION: X at position 10 is A or E

<400> SEQUENCE: 318

Leu Asp Leu Leu Leu Met Xaa Ile Met Xaa Met Leu
1               5                   10

<210> SEQ ID NO 319
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 319

Leu Asp Leu Leu Leu Met Xaa Ile Met Met Xaa Leu
1               5                   10

<210> SEQ ID NO 320
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 320

Leu Asp Leu Leu Leu Xaa Xaa Ile Xaa Met Met Leu
1               5                   10

<210> SEQ ID NO 321
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 321

Leu Asp Leu Leu Leu Xaa Xaa Ile Met Xaa Met Leu
1               5                   10
```

```
<210> SEQ ID NO 322
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 322

Leu Asp Leu Leu Leu Xaa Xaa Ile Met Met Xaa Leu
1               5                   10

<210> SEQ ID NO 323
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 323

Leu Asp Leu Leu Leu Met Xaa Ile Xaa Xaa Met Leu
1               5                   10

<210> SEQ ID NO 324
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 324

Leu Asp Leu Leu Leu Met Xaa Ile Xaa Met Xaa Leu
1               5                   10

<210> SEQ ID NO 325
<211> LENGTH: 12
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 325

Leu Asp Leu Leu Leu Met Xaa Ile Met Xaa Xaa Leu
1               5                   10

<210> SEQ ID NO 326
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 326

Leu Asp Leu Leu Leu Xaa Xaa Ile Met Xaa Xaa Leu
1               5                   10

<210> SEQ ID NO 327
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 327

Leu Asp Leu Leu Leu Xaa Xaa Ile Xaa Met Xaa Leu
1               5                   10
```

```
<210> SEQ ID NO 328
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 328

Leu Asp Leu Leu Leu Xaa Xaa Ile Xaa Xaa Met Leu
1               5                   10

<210> SEQ ID NO 329
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 329

Leu Asp Leu Leu Leu Met Xaa Ile Xaa Xaa Xaa Leu
1               5                   10

<210> SEQ ID NO 330
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V

<400> SEQUENCE: 330

Leu Asp Gln Leu Leu Leu Met Xaa Ile Met Met Met Leu
1               5                   10

<210> SEQ ID NO 331
<211> LENGTH: 13
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V

<400> SEQUENCE: 331

Leu Asp Gln Leu Leu Leu Xaa Xaa Ile Met Met Met Leu
1               5                   10

<210> SEQ ID NO 332
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 332

Leu Asp Gln Leu Leu Leu Met Xaa Ile Xaa Met Met Leu
1               5                   10

<210> SEQ ID NO 333
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 333

Leu Asp Gln Leu Leu Leu Met Xaa Ile Met Xaa Met Leu
1               5                   10

<210> SEQ ID NO 334
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 334

Leu Asp Gln Leu Leu Leu Met Xaa Ile Met Met Xaa Leu
1               5                   10
```

```
<210> SEQ ID NO 335
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 335

Leu Asp Gln Leu Leu Leu Xaa Xaa Ile Xaa Met Met Leu
1               5                   10

<210> SEQ ID NO 336
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 336

Leu Asp Gln Leu Leu Leu Xaa Xaa Ile Met Xaa Met Leu
1               5                   10

<210> SEQ ID NO 337
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 337

Leu Asp Gln Leu Leu Leu Xaa Xaa Ile Met Met Xaa Leu
1               5                   10

<210> SEQ ID NO 338
<211> LENGTH: 13
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 338

Leu Asp Gln Leu Leu Leu Met Xaa Ile Xaa Xaa Met Leu
1               5                   10

<210> SEQ ID NO 339
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 339

Leu Asp Gln Leu Leu Leu Met Xaa Ile Xaa Met Xaa Leu
1               5                   10

<210> SEQ ID NO 340
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 340

Leu Asp Gln Leu Leu Leu Met Xaa Ile Met Xaa Xaa Leu
1               5                   10

<210> SEQ ID NO 341
<211> LENGTH: 13
<212> TYPE: PRT
<213> ORGANISM: Artificial
<220> FEATURE:
<223> OTHER INFORMATION: Synthetic peptide
```

```
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 341

Leu Asp Gln Leu Leu Leu Xaa Xaa Ile Met Xaa Xaa Leu
1               5                   10

<210> SEQ ID NO 342
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 342

Leu Asp Gln Leu Leu Leu Xaa Xaa Ile Xaa Met Xaa Leu
1               5                   10

<210> SEQ ID NO 343
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 343

Leu Asp Gln Leu Leu Leu Xaa Xaa Ile Xaa Xaa Met Leu
1               5                   10
```

```
<210> SEQ ID NO 344
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 344

Leu Asp Gln Leu Leu Leu Met Xaa Ile Xaa Xaa Xaa Leu
1               5                   10

<210> SEQ ID NO 345
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V

<400> SEQUENCE: 345

Leu Asp Leu Leu Leu Met Phe Xaa Met Met Met Leu
1               5                   10

<210> SEQ ID NO 346
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V

<400> SEQUENCE: 346

Leu Asp Leu Leu Leu Xaa Phe Xaa Met Met Met Leu
1               5                   10

<210> SEQ ID NO 347
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
```

```
<220> FEATURE:
<221> NAME/KEY: MISC_FEATURE
<222> LOCATION: (9)..(9)
<223> OTHER INFORMATION: X at position 9 is A or E

<400> SEQUENCE: 347

Leu Asp Leu Leu Leu Met Phe Xaa Xaa Met Met Leu
1               5                   10

<210> SEQ ID NO 348
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 348

Leu Asp Leu Leu Leu Met Phe Xaa Met Xaa Met Leu
1               5                   10

<210> SEQ ID NO 349
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 349

Leu Asp Leu Leu Leu Met Phe Xaa Met Met Xaa Leu
1               5                   10

<210> SEQ ID NO 350
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E

<400> SEQUENCE: 350

Leu Asp Leu Leu Leu Xaa Phe Xaa Xaa Met Met Leu
1               5                   10

<210> SEQ ID NO 351
```

```
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 351

Leu Asp Leu Leu Leu Xaa Phe Xaa Met Xaa Met Leu
1               5                   10

<210> SEQ ID NO 352
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 352

Leu Asp Leu Leu Leu Xaa Phe Xaa Met Met Xaa Leu
1               5                   10

<210> SEQ ID NO 353
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 353

Leu Asp Leu Leu Leu Met Phe Xaa Xaa Xaa Met Leu
1               5                   10

<210> SEQ ID NO 354
<211> LENGTH: 12
<212> TYPE: PRT
<213> ORGANISM: Artificial
<220> FEATURE:
```

<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 354

Leu Asp Leu Leu Leu Met Phe Xaa Xaa Met Xaa Leu
1               5                   10

<210> SEQ ID NO 355
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 355

Leu Asp Leu Leu Leu Met Phe Xaa Met Xaa Xaa Leu
1               5                   10

<210> SEQ ID NO 356
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 356

Leu Asp Leu Leu Leu Met Phe Xaa Xaa Xaa Xaa Leu
1               5                   10

<210> SEQ ID NO 357
<211> LENGTH: 12
<212> TYPE: PRT
<213> ORGANISM: Artificial
<220> FEATURE:

<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 357

Leu Asp Leu Leu Leu Xaa Phe Xaa Met Xaa Xaa Leu
1               5                   10

<210> SEQ ID NO 358
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 358

Leu Asp Leu Leu Leu Xaa Phe Xaa Xaa Met Xaa Leu
1               5                   10

<210> SEQ ID NO 359
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 359

Leu Asp Leu Leu Leu Xaa Phe Xaa Xaa Xaa Met Leu

<210> SEQ ID NO 360
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (8)..(8)
<223> OTHER INFORMATION: X at position 8 is E or V
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 360

Leu Asp Leu Leu Leu Xaa Phe Xaa Xaa Xaa Xaa Leu
1               5                   10

<210> SEQ ID NO 361
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V

<400> SEQUENCE: 361

Leu Asp Gln Leu Leu Leu Met Phe Xaa Met Met Met Leu
1               5                   10

<210> SEQ ID NO 362
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V

<400> SEQUENCE: 362

Leu Asp Gln Leu Leu Leu Xaa Phe Xaa Met Met Met Leu
1               5                   10

<210> SEQ ID NO 363
<211> LENGTH: 13
<212> TYPE: PRT
<213> ORGANISM: Artificial
<220> FEATURE:

```
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 363

Leu Asp Gln Leu Leu Leu Met Phe Xaa Xaa Met Met Leu
1               5                   10

<210> SEQ ID NO 364
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 364

Leu Asp Gln Leu Leu Leu Met Phe Xaa Met Xaa Met Leu
1               5                   10

<210> SEQ ID NO 365
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 365

Leu Asp Gln Leu Leu Leu Met Phe Xaa Met Met Xaa Leu
1               5                   10

<210> SEQ ID NO 366
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 366
```

Leu Asp Gln Leu Leu Leu Xaa Phe Xaa Xaa Met Met Leu
1               5                   10

<210> SEQ ID NO 367
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 367

Leu Asp Gln Leu Leu Leu Xaa Phe Xaa Met Xaa Met Leu
1               5                   10

<210> SEQ ID NO 368
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 368

Leu Asp Gln Leu Leu Leu Xaa Phe Xaa Met Met Xaa Leu
1               5                   10

<210> SEQ ID NO 369
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 369

Leu Asp Gln Leu Leu Leu Met Phe Xaa Xaa Xaa Met Leu
1               5                   10

```
<210> SEQ ID NO 370
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 370

Leu Asp Gln Leu Leu Leu Met Phe Xaa Xaa Met Xaa Leu
1               5                   10

<210> SEQ ID NO 371
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 371

Leu Asp Gln Leu Leu Leu Met Phe Xaa Met Xaa Xaa Leu
1               5                   10

<210> SEQ ID NO 372
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 372

Leu Asp Gln Leu Leu Leu Met Phe Xaa Xaa Xaa Xaa Leu
1               5                   10
```

```
<210> SEQ ID NO 373
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 373

Leu Asp Gln Leu Leu Leu Xaa Phe Xaa Met Xaa Xaa Leu
1               5                   10

<210> SEQ ID NO 374
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 374

Leu Asp Gln Leu Leu Leu Xaa Phe Xaa Xaa Met Xaa Leu
1               5                   10

<210> SEQ ID NO 375
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
```

<223> OTHER INFORMATION: X at position 11 is A or E

<400> SEQUENCE: 375

Leu Asp Gln Leu Leu Leu Xaa Phe Xaa Xaa Xaa Met Leu
1               5                   10

<210> SEQ ID NO 376
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 376

Leu Asp Gln Leu Leu Leu Xaa Phe Xaa Xaa Xaa Xaa Leu
1               5                   10

<210> SEQ ID NO 377
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V

<400> SEQUENCE: 377

Leu Asp Leu Leu Leu Met Phe Ile Xaa Met Met Leu
1               5                   10

<210> SEQ ID NO 378
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is E or V

<400> SEQUENCE: 378

Leu Asp Leu Leu Leu Xaa Phe Ile Xaa Met Met Leu
1               5                   10

```
<210> SEQ ID NO 379
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 379

Leu Asp Leu Leu Leu Met Phe Ile Xaa Xaa Met Leu
1               5                   10

<210> SEQ ID NO 380
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 380

Leu Asp Leu Leu Leu Met Phe Ile Xaa Met Xaa Leu
1               5                   10

<210> SEQ ID NO 381
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 381

Leu Asp Leu Leu Leu Xaa Phe Ile Xaa Xaa Met Leu
1               5                   10

<210> SEQ ID NO 382
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
```

<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E

<400> SEQUENCE: 382

Leu Asp Leu Leu Leu Xaa Phe Ile Xaa Xaa Met Leu
1               5                   10

<210> SEQ ID NO 383
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 383

Leu Asp Leu Leu Leu Xaa Phe Ile Xaa Met Xaa Leu
1               5                   10

<210> SEQ ID NO 384
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 384

Leu Asp Leu Leu Leu Met Phe Ile Xaa Xaa Xaa Leu
1               5                   10

<210> SEQ ID NO 385
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is E or V
<220> FEATURE:
<221> NAME/KEY: MISC_FEATURE

```
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 385

Leu Asp Leu Leu Leu Xaa Phe Ile Xaa Xaa Xaa Leu
1               5                   10

<210> SEQ ID NO 386
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is E or V

<400> SEQUENCE: 386

Leu Asp Gln Leu Leu Leu Met Phe Ile Xaa Met Met Leu
1               5                   10

<210> SEQ ID NO 387
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is E or V

<400> SEQUENCE: 387

Leu Asp Gln Leu Leu Leu Xaa Phe Ile Xaa Met Met Leu
1               5                   10

<210> SEQ ID NO 388
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 388

Leu Asp Gln Leu Leu Leu Met Phe Ile Xaa Xaa Met Leu
1               5                   10

<210> SEQ ID NO 389
<211> LENGTH: 13
<212> TYPE: PRT
<213> ORGANISM: Artificial
<220> FEATURE:
<223> OTHER INFORMATION: Synthetic peptide
<220> FEATURE:
```

-continued

```
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 389

Leu Asp Gln Leu Leu Leu Met Phe Ile Xaa Met Xaa Leu
1               5                   10

<210> SEQ ID NO 390
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 390

Leu Asp Gln Leu Leu Leu Xaa Phe Ile Xaa Xaa Met Leu
1               5                   10

<210> SEQ ID NO 391
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 391

Leu Asp Gln Leu Leu Leu Xaa Phe Ile Xaa Met Xaa Leu
1               5                   10

<210> SEQ ID NO 392
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E
<220> FEATURE:
```

```
<221> NAME/KEY: MISC_FEATURE
<222> LOCATION: (12)..(12)
<223> OTHER INFORMATION: X at position 12 is A or E

<400> SEQUENCE: 392

Leu Asp Gln Leu Leu Leu Met Phe Ile Xaa Xaa Xaa Leu
1               5                   10

<210> SEQ ID NO 393
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 393

Leu Asp Gln Leu Leu Leu Xaa Phe Ile Xaa Xaa Xaa Leu
1               5                   10

<210> SEQ ID NO 394
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is E or V

<400> SEQUENCE: 394

Leu Asp Leu Leu Leu Met Phe Ile Met Xaa Met Leu
1               5                   10

<210> SEQ ID NO 395
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is E or V

<400> SEQUENCE: 395

Leu Asp Leu Leu Leu Xaa Phe Ile Met Xaa Met Leu
1               5                   10

<210> SEQ ID NO 396
<211> LENGTH: 12
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 396

Leu Asp Leu Leu Leu Met Phe Ile Met Xaa Xaa Leu
1               5                   10

<210> SEQ ID NO 397
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is E or V

<400> SEQUENCE: 397

Leu Asp Leu Leu Leu Met Phe Ile Xaa Xaa Met Leu
1               5                   10

<210> SEQ ID NO 398
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 398

Leu Asp Leu Leu Leu Xaa Phe Ile Met Xaa Xaa Leu
1               5                   10

<210> SEQ ID NO 399
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
```

```
<220> FEATURE:
<221> NAME/KEY: MISC_FEATURE
<222> LOCATION: (10)..(10)
<223> OTHER INFORMATION: X at position 10 is E or V

<400> SEQUENCE: 399

Leu Asp Leu Leu Leu Xaa Phe Ile Xaa Xaa Met Leu
1               5                   10

<210> SEQ ID NO 400
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 400

Leu Asp Leu Leu Leu Met Phe Ile Xaa Xaa Xaa Leu
1               5                   10

<210> SEQ ID NO 401
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is E or V
<220> FEATURE:
<221> NAME/KEY: MISC_FEATURE
<222> LOCATION: (11)..(11)
<223> OTHER INFORMATION: X at position 11 is A or E

<400> SEQUENCE: 401

Leu Asp Leu Leu Leu Xaa Phe Ile Xaa Xaa Xaa Leu
1               5                   10

<210> SEQ ID NO 402
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is E or V

<400> SEQUENCE: 402

Leu Asp Gln Leu Leu Leu Met Phe Ile Met Xaa Met Leu
```

```
1               5                   10
```

<210> SEQ ID NO 403
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 403

```
Leu Asp Gln Leu Leu Leu Xaa Phe Ile Met Xaa Met Leu
1               5                   10
```

<210> SEQ ID NO 404
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 404

```
Leu Asp Gln Leu Leu Leu Met Phe Ile Met Xaa Xaa Leu
1               5                   10
```

<210> SEQ ID NO 405
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 405

```
Leu Asp Gln Leu Leu Leu Met Phe Ile Xaa Xaa Met Leu
1               5                   10
```

<210> SEQ ID NO 406
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)

<223> OTHER INFORMATION: X at position 11 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 406

Leu Asp Gln Leu Leu Leu Xaa Phe Ile Met Xaa Xaa Leu
1               5                   10

<210> SEQ ID NO 407
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 407

Leu Asp Gln Leu Leu Leu Xaa Phe Ile Xaa Xaa Met Leu
1               5                   10

<210> SEQ ID NO 408
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 408

Leu Asp Gln Leu Leu Leu Met Phe Ile Xaa Xaa Xaa Leu
1               5                   10

<210> SEQ ID NO 409
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)

<223> OTHER INFORMATION: X at position 11 is E or V
<220> FEATURE:
<221> NAME/KEY: MISC_FEATURE
<222> LOCATION: (12)..(12)
<223> OTHER INFORMATION: X at position 12 is A or E

<400> SEQUENCE: 409

Leu Asp Gln Leu Leu Leu Xaa Phe Ile Xaa Xaa Xaa Leu
1               5                   10

<210> SEQ ID NO 410
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is E or V

<400> SEQUENCE: 410

Leu Asp Leu Leu Leu Met Phe Ile Met Met Xaa Leu
1               5                   10

<210> SEQ ID NO 411
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 411

Leu Asp Leu Leu Leu Xaa Phe Ile Met Met Xaa Leu
1               5                   10

<210> SEQ ID NO 412
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 412

Leu Asp Leu Leu Leu Met Phe Ile Xaa Met Xaa Leu
1               5                   10

<210> SEQ ID NO 413
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE

```
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 413

Leu Asp Leu Leu Leu Met Phe Ile Met Xaa Xaa Leu
1               5                   10

<210> SEQ ID NO 414
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 414

Leu Asp Leu Leu Leu Xaa Phe Ile Xaa Met Xaa Leu
1               5                   10

<210> SEQ ID NO 415
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 415

Leu Asp Leu Leu Leu Xaa Phe Ile Met Xaa Xaa Leu
1               5                   10

<210> SEQ ID NO 416
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
```

```
<222> LOCATION: (11)..(11)
<223> OTHER INFORMATION: X at position 11 is E or V

<400> SEQUENCE: 416

Leu Asp Leu Leu Leu Met Phe Ile Xaa Xaa Xaa Leu
1               5                   10

<210> SEQ ID NO 417
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is E or V

<400> SEQUENCE: 417

Leu Asp Leu Leu Leu Xaa Phe Ile Xaa Xaa Xaa Leu
1               5                   10

<210> SEQ ID NO 418
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: X at position 12 is E or V

<400> SEQUENCE: 418

Leu Asp Gln Leu Leu Leu Met Phe Ile Met Met Xaa Leu
1               5                   10

<210> SEQ ID NO 419
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 419

Leu Asp Gln Leu Leu Leu Xaa Phe Ile Met Met Xaa Leu
1               5                   10

<210> SEQ ID NO 420
<211> LENGTH: 13
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 420

Leu Asp Gln Leu Leu Leu Met Phe Ile Xaa Met Xaa Leu
1               5                   10

<210> SEQ ID NO 421
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 421

Leu Asp Gln Leu Leu Leu Met Phe Ile Met Xaa Xaa Leu
1               5                   10

<210> SEQ ID NO 422
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 422

Leu Asp Gln Leu Leu Leu Xaa Phe Ile Xaa Met Xaa Leu
1               5                   10

<210> SEQ ID NO 423
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
```

```
<221> NAME/KEY: MISC_FEATURE
<222> LOCATION: (12)..(12)
<223> OTHER INFORMATION: X at position 12 is E or V

<400> SEQUENCE: 423

Leu Asp Gln Leu Leu Leu Xaa Phe Ile Met Xaa Xaa Leu
1               5                   10

<210> SEQ ID NO 424
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 424

Leu Asp Gln Leu Leu Leu Met Phe Ile Xaa Xaa Xaa Leu
1               5                   10

<210> SEQ ID NO 425
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 425

Leu Asp Gln Leu Leu Leu Xaa Phe Ile Xaa Xaa Xaa Leu
1               5                   10

<210> SEQ ID NO 426
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: X at position 12 is E or V

<400> SEQUENCE: 426

Leu Asp Leu Leu Leu Met Phe Ile Met Met Met Xaa
1               5                   10
```

<210> SEQ ID NO 427
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 427

Leu Asp Leu Leu Leu Xaa Phe Ile Met Met Met Xaa
1               5                   10

<210> SEQ ID NO 428
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 428

Leu Asp Leu Leu Leu Met Phe Ile Xaa Met Met Xaa
1               5                   10

<210> SEQ ID NO 429
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 429

Leu Asp Leu Leu Leu Met Phe Ile Met Xaa Met Xaa
1               5                   10

<210> SEQ ID NO 430
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 430

Leu Asp Leu Leu Leu Met Phe Ile Met Met Xaa Xaa
1               5                   10

<210> SEQ ID NO 431
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 431

Leu Asp Leu Leu Leu Xaa Phe Ile Xaa Met Met Xaa
1               5                   10

<210> SEQ ID NO 432
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 432

Leu Asp Leu Leu Leu Xaa Phe Ile Met Xaa Met Xaa
1               5                   10

<210> SEQ ID NO 433
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 433

Leu Asp Leu Leu Leu Xaa Phe Ile Met Met Xaa Xaa

```
1               5                  10
```

<210> SEQ ID NO 434
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 434

```
Leu Asp Leu Leu Leu Met Phe Ile Xaa Xaa Met Xaa
1               5                  10
```

<210> SEQ ID NO 435
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 435

```
Leu Asp Leu Leu Leu Met Phe Ile Xaa Met Xaa Xaa
1               5                  10
```

<210> SEQ ID NO 436
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 436

```
Leu Asp Leu Leu Leu Met Phe Ile Met Xaa Xaa Xaa
1               5                  10
```

<210> SEQ ID NO 437

```
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 437

Leu Asp Leu Leu Leu Met Phe Ile Xaa Xaa Xaa Xaa
1               5                   10

<210> SEQ ID NO 438
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 438

Leu Asp Leu Leu Leu Xaa Phe Ile Met Xaa Xaa Xaa
1               5                   10

<210> SEQ ID NO 439
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V
```

<400> SEQUENCE: 439

Leu Asp Leu Leu Leu Xaa Phe Ile Xaa Met Xaa Xaa
1               5                   10

<210> SEQ ID NO 440
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 440

Leu Asp Leu Leu Leu Xaa Phe Ile Xaa Xaa Met Xaa
1               5                   10

<210> SEQ ID NO 441
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 441

Leu Asp Leu Leu Leu Xaa Phe Ile Xaa Xaa Xaa Xaa
1               5                   10

<210> SEQ ID NO 442
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: X at position 13 is E or V

<400> SEQUENCE: 442

Leu Asp Gln Leu Leu Leu Met Phe Ile Met Met Met Xaa
1               5                   10

<210> SEQ ID NO 443
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 443

Leu Asp Gln Leu Leu Leu Xaa Phe Ile Met Met Met Xaa
1               5                   10

<210> SEQ ID NO 444
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 444

Leu Asp Gln Leu Leu Leu Met Phe Ile Xaa Met Met Xaa
1               5                   10

<210> SEQ ID NO 445
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 445

Leu Asp Gln Leu Leu Leu Met Phe Ile Met Xaa Met Xaa
1               5                   10

<210> SEQ ID NO 446
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(12)

<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 446

Leu Asp Gln Leu Leu Leu Met Phe Ile Met Met Xaa Xaa
1               5                   10

<210> SEQ ID NO 447
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 447

Leu Asp Gln Leu Leu Leu Xaa Phe Ile Xaa Met Met Xaa
1               5                   10

<210> SEQ ID NO 448
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 448

Leu Asp Gln Leu Leu Leu Xaa Phe Ile Met Xaa Met Xaa
1               5                   10

<210> SEQ ID NO 449
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)

<223> OTHER INFORMATION: X at position 13 is E or V

<400> SEQUENCE: 449

Leu Asp Gln Leu Leu Leu Xaa Phe Ile Met Met Xaa Xaa
1               5                   10

<210> SEQ ID NO 450
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 450

Leu Asp Gln Leu Leu Leu Met Phe Ile Xaa Xaa Met Xaa
1               5                   10

<210> SEQ ID NO 451
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 451

Leu Asp Gln Leu Leu Leu Met Phe Ile Xaa Met Xaa Xaa
1               5                   10

<210> SEQ ID NO 452
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 452

```
Leu Asp Gln Leu Leu Leu Met Phe Ile Met Xaa Xaa Xaa
1               5                   10
```

<210> SEQ ID NO 453
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 453

```
Leu Asp Gln Leu Leu Leu Met Phe Ile Xaa Xaa Xaa Xaa
1               5                   10
```

<210> SEQ ID NO 454
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 454

```
Leu Asp Gln Leu Leu Leu Xaa Phe Ile Met Xaa Xaa Xaa
1               5                   10
```

<210> SEQ ID NO 455
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)

```
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 455

Leu Asp Gln Leu Leu Leu Xaa Phe Ile Xaa Met Xaa Xaa
1               5                   10

<210> SEQ ID NO 456
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 456

Leu Asp Gln Leu Leu Leu Xaa Phe Ile Xaa Xaa Met Xaa
1               5                   10

<210> SEQ ID NO 457
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 457

Leu Asp Gln Leu Leu Leu Xaa Phe Ile Xaa Xaa Xaa Xaa
1               5                   10

<210> SEQ ID NO 458
<211> LENGTH: 12
<212> TYPE: PRT
<213> ORGANISM: Artificial
<220> FEATURE:
```

<223> OTHER INFORMATION: Synthetic peptide

<400> SEQUENCE: 458

Leu Lys Leu Leu Leu Met Phe Ile Met Met Met Leu
1               5                   10

<210> SEQ ID NO 459
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E

<400> SEQUENCE: 459

Leu Lys Leu Leu Leu Xaa Phe Ile Met Met Met Leu
1               5                   10

<210> SEQ ID NO 460
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E

<400> SEQUENCE: 460

Leu Lys Leu Leu Leu Met Phe Ile Xaa Met Met Leu
1               5                   10

<210> SEQ ID NO 461
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E

<400> SEQUENCE: 461

Leu Lys Leu Leu Leu Met Phe Ile Met Xaa Met Leu
1               5                   10

<210> SEQ ID NO 462
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E

<400> SEQUENCE: 462

Leu Lys Leu Leu Leu Met Phe Ile Met Met Xaa Leu
1               5                   10

<210> SEQ ID NO 463
<211> LENGTH: 12
<212> TYPE: PRT

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E

<400> SEQUENCE: 463

Leu Lys Leu Leu Leu Xaa Phe Ile Xaa Met Met Leu
1               5                   10

<210> SEQ ID NO 464
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 464

Leu Lys Leu Leu Leu Xaa Phe Ile Met Xaa Met Leu
1               5                   10

<210> SEQ ID NO 465
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 465

Leu Lys Leu Leu Leu Xaa Phe Ile Met Met Xaa Leu
1               5                   10

<210> SEQ ID NO 466
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 466

Leu Lys Leu Leu Leu Met Phe Ile Xaa Xaa Met Leu
1               5                   10
```

```
<210> SEQ ID NO 467
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 467

Leu Lys Leu Leu Leu Met Phe Ile Xaa Met Xaa Leu
1               5                   10

<210> SEQ ID NO 468
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 468

Leu Lys Leu Leu Leu Met Phe Ile Met Xaa Xaa Leu
1               5                   10

<210> SEQ ID NO 469
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 469

Leu Lys Leu Leu Leu Met Phe Ile Xaa Xaa Xaa Leu
1               5                   10

<210> SEQ ID NO 470
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
```

<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 470

Leu Lys Leu Leu Leu Xaa Phe Ile Met Xaa Xaa Xaa
1               5                   10

<210> SEQ ID NO 471
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 471

Leu Lys Leu Leu Leu Xaa Phe Ile Xaa Met Xaa Xaa
1               5                   10

<210> SEQ ID NO 472
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is E or V

<400> SEQUENCE: 472

Leu Lys Leu Leu Leu Xaa Phe Ile Xaa Xaa Met Xaa
1               5                   10

<210> SEQ ID NO 473
<211> LENGTH: 12

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at position 6 is A or E
<220> FEATURE:
<221> NAME/KEY: MISC_FEATURE
<222> LOCATION: (9)..(9)
<223> OTHER INFORMATION: X at position 9 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 473

Leu Lys Leu Leu Leu Xaa Phe Ile Xaa Xaa Xaa Leu
1               5                   10

<210> SEQ ID NO 474
<211> LENGTH: 13
<212> TYPE: PRT
<213> ORGANISM: Artificial
<220> FEATURE:
<223> OTHER INFORMATION: Synthetic peptide

<400> SEQUENCE: 474

Leu Lys Gln Leu Leu Leu Met Phe Ile Met Met Met Leu
1               5                   10

<210> SEQ ID NO 475
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E

<400> SEQUENCE: 475

Leu Lys Gln Leu Leu Leu Xaa Phe Ile Met Met Met Leu
1               5                   10

<210> SEQ ID NO 476
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E

<400> SEQUENCE: 476

Leu Lys Gln Leu Leu Leu Met Phe Ile Xaa Met Met Leu
1               5                   10

<210> SEQ ID NO 477
<211> LENGTH: 13
<212> TYPE: PRT
<213> ORGANISM: Artificial
<220> FEATURE:
```

<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E

<400> SEQUENCE: 477

Leu Lys Gln Leu Leu Leu Met Phe Ile Met Xaa Met Leu
1               5                   10

<210> SEQ ID NO 478
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: X at position 12 is A or E

<400> SEQUENCE: 478

Leu Lys Gln Leu Leu Leu Met Phe Ile Met Met Xaa Leu
1               5                   10

<210> SEQ ID NO 479
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 479

Leu Lys Gln Leu Leu Leu Xaa Phe Ile Xaa Met Met Leu
1               5                   10

<210> SEQ ID NO 480
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 480

Leu Lys Gln Leu Leu Leu Xaa Phe Ile Met Xaa Met Leu
1               5                   10

<210> SEQ ID NO 481
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE

```
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 481

Leu Lys Gln Leu Leu Leu Xaa Phe Ile Met Met Xaa Leu
1               5                   10

<210> SEQ ID NO 482
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 482

Leu Lys Gln Leu Leu Leu Met Phe Ile Xaa Xaa Met Leu
1               5                   10

<210> SEQ ID NO 483
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 483

Leu Lys Gln Leu Leu Leu Met Phe Ile Xaa Met Xaa Leu
1               5                   10

<210> SEQ ID NO 484
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 484

Leu Lys Gln Leu Leu Leu Met Phe Ile Met Xaa Xaa Leu
1               5                   10

<210> SEQ ID NO 485
<211> LENGTH: 13
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 485

Leu Lys Gln Leu Leu Leu Met Phe Ile Xaa Xaa Xaa Leu
1               5                   10

<210> SEQ ID NO 486
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 486

Leu Lys Gln Leu Leu Leu Xaa Phe Ile Met Xaa Xaa Xaa
1               5                   10

<210> SEQ ID NO 487
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 487

Leu Lys Gln Leu Leu Leu Xaa Phe Ile Xaa Met Xaa Xaa
1               5                   10
```

```
<210> SEQ ID NO 488
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (13)..(13)
<223> OTHER INFORMATION: X at position 13 is E or V

<400> SEQUENCE: 488

Leu Lys Gln Leu Leu Leu Xaa Phe Ile Xaa Xaa Met Xaa
1               5                   10

<210> SEQ ID NO 489
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 489

Leu Lys Gln Leu Leu Leu Xaa Phe Ile Xaa Xaa Xaa Leu
1               5                   10

<210> SEQ ID NO 490
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A

<400> SEQUENCE: 490

Leu Asp Xaa Leu Leu Leu Met Phe Ile Met Met Met Leu
1               5                   10

<210> SEQ ID NO 491
<211> LENGTH: 13
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E

<400> SEQUENCE: 491

Leu Asp Xaa Leu Leu Leu Xaa Phe Ile Met Met Met Leu
1               5                   10

<210> SEQ ID NO 492
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (10)..(10)
<223> OTHER INFORMATION: X at position 10 is A or E

<400> SEQUENCE: 492

Leu Asp Xaa Leu Leu Leu Met Phe Ile Xaa Met Met Leu
1               5                   10

<210> SEQ ID NO 493
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (11)..(11)
<223> OTHER INFORMATION: X at position 11 is A or E

<400> SEQUENCE: 493

Leu Asp Xaa Leu Leu Leu Met Phe Ile Met Xaa Met Leu
1               5                   10

<210> SEQ ID NO 494
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (12)..(12)
<223> OTHER INFORMATION: X at position 12 is A or E

<400> SEQUENCE: 494

Leu Asp Xaa Leu Leu Leu Met Phe Ile Met Met Xaa Leu
1               5                   10
```

<210> SEQ ID NO 495
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E

<400> SEQUENCE: 495

Leu Asp Xaa Leu Leu Leu Xaa Phe Ile Xaa Met Met Leu
1               5                   10

<210> SEQ ID NO 496
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 496

Leu Asp Xaa Leu Leu Leu Xaa Phe Ile Met Xaa Met Leu
1               5                   10

<210> SEQ ID NO 497
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 497

Leu Asp Xaa Leu Leu Leu Xaa Phe Ile Met Met Xaa Leu
1               5                   10

<210> SEQ ID NO 498
<211> LENGTH: 13

<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 498

Leu Asp Xaa Leu Leu Leu Met Phe Ile Xaa Xaa Met Leu
1               5                   10

<210> SEQ ID NO 499
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 499

Leu Asp Xaa Leu Leu Leu Met Phe Ile Xaa Met Xaa Leu
1               5                   10

<210> SEQ ID NO 500
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 500

Leu Asp Xaa Leu Leu Leu Met Phe Ile Met Xaa Xaa Leu
1               5                   10

<210> SEQ ID NO 501
<211> LENGTH: 13
<212> TYPE: PRT
<213> ORGANISM: Artificial
<220> FEATURE:
<223> OTHER INFORMATION: Synthetic peptide

```
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 501

Leu Asp Xaa Leu Leu Leu Met Phe Ile Xaa Xaa Xaa Leu
1               5                   10

<210> SEQ ID NO 502
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 502

Leu Asp Xaa Leu Leu Leu Xaa Phe Ile Met Xaa Xaa Leu
1               5                   10

<210> SEQ ID NO 503
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 503

Leu Asp Xaa Leu Leu Leu Xaa Phe Ile Xaa Met Xaa Leu
1               5                   10
```

```
<210> SEQ ID NO 504
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E

<400> SEQUENCE: 504

Leu Asp Xaa Leu Leu Leu Xaa Phe Ile Xaa Xaa Met Leu
1               5                   10

<210> SEQ ID NO 505
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X at position 3 is E, S, or A
<220> FEATURE:
<221> NAME/KEY: MISC_FEATURE
<222> LOCATION: (7)..(7)
<223> OTHER INFORMATION: X at position 7 is A or E
<220> FEATURE:
<221> NAME/KEY: MISC_FEATURE
<222> LOCATION: (10)..(10)
<223> OTHER INFORMATION: X at position 10 is A or E
<220> FEATURE:
<221> NAME/KEY: MISC_FEATURE
<222> LOCATION: (11)..(11)
<223> OTHER INFORMATION: X at position 11 is A or E
<220> FEATURE:
<221> NAME/KEY: MISC_FEATURE
<222> LOCATION: (12)..(12)
<223> OTHER INFORMATION: X at position 12 is A or E

<400> SEQUENCE: 505

Leu Asp Xaa Leu Leu Leu Xaa Phe Ile Xaa Xaa Xaa Leu
1               5                   10

<210> SEQ ID NO 506
<211> LENGTH: 63
<212> TYPE: DNA
<213> ORGANISM: Artificial
<220> FEATURE:
<223> OTHER INFORMATION: P5 in E. coli

<400> SEQUENCE: 506
agcgcaggta gcgaacagca gctggatctg ctgctgatgt ttattatgat gatgctgcag      60
cag                                                                   63

<210> SEQ ID NO 507
```

-continued

```
<210> SEQ ID NO 507
<211> LENGTH: 60
<212> TYPE: DNA
<213> ORGANISM: Artificial
<220> FEATURE:
<223> OTHER INFORMATION: P5-21 in E. coli

<400> SEQUENCE: 507
agcgaagaac agctggaact gctgctggca tttattgcag cagcactgca gcaggaagaa      60

<210> SEQ ID NO 508
<211> LENGTH: 63
<212> TYPE: DNA
<213> ORGANISM: Artificial
<220> FEATURE:
<223> OTHER INFORMATION: P5 in Zea mays

<400> SEQUENCE: 508
tccgccggct ccgagcagca gctggacctg ctgctgatgt tcatcatgat gatgctgcag      60
cag                                                                   63

<210> SEQ ID NO 509
<211> LENGTH: 60
<212> TYPE: DNA
<213> ORGANISM: Artificial
<220> FEATURE:
<223> OTHER INFORMATION: P5-21 in Zea mays

<400> SEQUENCE: 509
tccgaggagc agctggagct gctgctggcc ttcatcgccg ccgccctgca gcaggaggag      60

<210> SEQ ID NO 510
<211> LENGTH: 21
<212> TYPE: PRT
<213> ORGANISM: Artificial
<220> FEATURE:
<223> OTHER INFORMATION: Synthetic peptide

<400> SEQUENCE: 510

Ser Ala Gly Ser Glu Gln Gln Glu Asp Leu Leu Ala Phe Ile Ala
1               5                   10                  15

Ala Ala Leu Gln Gln
            20

<210> SEQ ID NO 511
<211> LENGTH: 21
<212> TYPE: PRT
<213> ORGANISM: Artificial
<220> FEATURE:
<223> OTHER INFORMATION: Synthetic peptide

<400> SEQUENCE: 511

Ser Ala Gly Ser Glu Gln Gln Leu Asp Glu Leu Leu Ala Phe Ile Ala
1               5                   10                  15

Ala Ala Leu Gln Gln
            20

<210> SEQ ID NO 512
<211> LENGTH: 21
<212> TYPE: PRT
<213> ORGANISM: Artificial
<220> FEATURE:
<223> OTHER INFORMATION: Synthetic peptide

<400> SEQUENCE: 512

Ser Ala Gly Ser Glu Gln Gln Glu Asp Glu Leu Leu Ala Phe Ile Ala
```

-continued

```
1               5                   10                  15

Ala Ala Leu Gln Gln
            20

<210> SEQ ID NO 513
<211> LENGTH: 21
<212> TYPE: PRT
<213> ORGANISM: Artificial
<220> FEATURE:
<223> OTHER INFORMATION: Synthetic peptide

<400> SEQUENCE: 513

Ser Ala Gly Ser Glu Gln Gln Glu Asp Glu Leu Leu Met Phe Ile Met
1               5                   10                  15

Met Met Leu Gln Gln
            20

<210> SEQ ID NO 514
<211> LENGTH: 20
<212> TYPE: PRT
<213> ORGANISM: Artificial
<220> FEATURE:
<223> OTHER INFORMATION: Synthetic peptide

<400> SEQUENCE: 514

Ser Glu Glu Gln Glu Glu Leu Leu Leu Ala Phe Ile Ala Ala Ala Leu
1               5                   10                  15

Gln Gln Glu Glu
            20

<210> SEQ ID NO 515
<211> LENGTH: 20
<212> TYPE: PRT
<213> ORGANISM: Artificial
<220> FEATURE:
<223> OTHER INFORMATION: Synthetic peptide

<400> SEQUENCE: 515

Ser Glu Glu Gln Leu Glu Glu Leu Leu Ala Phe Ile Ala Ala Ala Leu
1               5                   10                  15

Gln Gln Glu Glu
            20

<210> SEQ ID NO 516
<211> LENGTH: 20
<212> TYPE: PRT
<213> ORGANISM: Artificial
<220> FEATURE:
<223> OTHER INFORMATION: Synthetic peptide

<400> SEQUENCE: 516

Ser Glu Glu Gln Glu Glu Glu Leu Leu Ala Phe Ile Ala Ala Ala Leu
1               5                   10                  15

Gln Gln Glu Glu
            20

<210> SEQ ID NO 517
<211> LENGTH: 22
<212> TYPE: PRT
<213> ORGANISM: Artificial
<220> FEATURE:
<223> OTHER INFORMATION: Synthetic peptide

<400> SEQUENCE: 517
```

```
Ser Ala Gly Ser Glu Gln Gln Leu Asp Leu Leu Met Phe Ile Met
1               5                   10                  15
Met Met Leu Gln Gln Arg
            20
```

<210> SEQ ID NO 518
<211> LENGTH: 21
<212> TYPE: PRT
<213> ORGANISM: Artificial
<220> FEATURE:
<223> OTHER INFORMATION: Synthetic peptide

<400> SEQUENCE: 518

```
Ser Glu Glu Gln Leu Glu Leu Leu Leu Ala Phe Ile Ala Ala Ala Leu
1               5                   10                  15
Gln Gln Glu Glu Arg
            20
```

<210> SEQ ID NO 519
<211> LENGTH: 19
<212> TYPE: PRT
<213> ORGANISM: Artificial
<220> FEATURE:
<223> OTHER INFORMATION: Synthetic peptide

<400> SEQUENCE: 519

```
Ser Ala Gly Ser Glu Gln Gln Glu Asp Leu Leu Leu Ala Phe Ile Ala
1               5                   10                  15
Leu Gln Gln
```

<210> SEQ ID NO 520
<211> LENGTH: 19
<212> TYPE: PRT
<213> ORGANISM: Artificial
<220> FEATURE:
<223> OTHER INFORMATION: Synthetic peptide

<400> SEQUENCE: 520

```
Ser Ala Gly Ser Glu Gln Gln Leu Asp Glu Leu Leu Ala Phe Ile Ala
1               5                   10                  15
Leu Gln Gln
```

<210> SEQ ID NO 521
<211> LENGTH: 19
<212> TYPE: PRT
<213> ORGANISM: Artificial
<220> FEATURE:
<223> OTHER INFORMATION: Synthetic peptide

<400> SEQUENCE: 521

```
Ser Ala Gly Ser Glu Gln Gln Leu Asp Leu Leu Leu Glu Phe Ile Ala
1               5                   10                  15
Leu Gln Gln
```

<210> SEQ ID NO 522
<211> LENGTH: 19
<212> TYPE: PRT
<213> ORGANISM: Artificial
<220> FEATURE:
<223> OTHER INFORMATION: Synthetic peptide

<400> SEQUENCE: 522

```
Ser Ala Gly Ser Glu Gln Gln Leu Asp Leu Leu Leu Ala Glu Ile Ala
1               5                   10                  15
```

Leu Gln Gln

<210> SEQ ID NO 523
<211> LENGTH: 20
<212> TYPE: PRT
<213> ORGANISM: Artificial
<220> FEATURE:
<223> OTHER INFORMATION: Synthetic peptide

<400> SEQUENCE: 523

Ser Ala Gly Ser Glu Gln Gln Leu Asp Leu Leu Leu Ala Phe Ile Glu
1               5                   10                  15

Ala Leu Gln Gln
            20

<210> SEQ ID NO 524
<211> LENGTH: 21
<212> TYPE: PRT
<213> ORGANISM: Artificial
<220> FEATURE:
<223> OTHER INFORMATION: Synthetic peptide

<400> SEQUENCE: 524

Ser Ala Gly Ser Glu Gln Gln Leu Asp Leu Leu Leu Ala Phe Ile Ala
1               5                   10                  15

Glu Ala Leu Gln Gln
            20

<210> SEQ ID NO 525
<211> LENGTH: 21
<212> TYPE: PRT
<213> ORGANISM: Artificial
<220> FEATURE:
<223> OTHER INFORMATION: Synthetic peptide

<400> SEQUENCE: 525

Ser Ala Gly Ser Glu Gln Gln Leu Asp Leu Leu Leu Ala Phe Ile Glu
1               5                   10                  15

Ala Ala Leu Gln Gln
            20

<210> SEQ ID NO 526
<211> LENGTH: 21
<212> TYPE: PRT
<213> ORGANISM: Artificial
<220> FEATURE:
<223> OTHER INFORMATION: Synthetic peptide

<400> SEQUENCE: 526

Ser Ala Gly Ser Glu Gln Gln Leu Asp Leu Leu Leu Ala Phe Ile Ala
1               5                   10                  15

Ala Glu Leu Gln Gln
            20

<210> SEQ ID NO 527
<211> LENGTH: 21
<212> TYPE: PRT
<213> ORGANISM: Artificial
<220> FEATURE:
<223> OTHER INFORMATION: Synthetic peptide

<400> SEQUENCE: 527

Ser Ala Gly Ser Glu Gln Gln Leu Asp Leu Leu Leu Ala Glu Ile Ala
1               5                   10                  15

Ala Ala Leu Gln Gln
            20

<210> SEQ ID NO 528
<211> LENGTH: 21
<212> TYPE: PRT
<213> ORGANISM: Artificial
<220> FEATURE:
<223> OTHER INFORMATION: Synthetic peptide

<400> SEQUENCE: 528

Ser Ala Gly Ser Glu Gln Gln Leu Asp Leu Leu Glu Phe Ile Ala
1               5                   10                  15

Ala Ala Leu Gln Gln
            20

<210> SEQ ID NO 529
<211> LENGTH: 21
<212> TYPE: PRT
<213> ORGANISM: Artificial
<220> FEATURE:
<223> OTHER INFORMATION: Synthetic peptide

<400> SEQUENCE: 529

Ser Ala Gly Ser Glu Gln Gln Glu Asp Leu Leu Leu Ala Phe Ile Ala
1               5                   10                  15

Ala Ala Leu Gln Gln
            20

<210> SEQ ID NO 530
<211> LENGTH: 21
<212> TYPE: PRT
<213> ORGANISM: Artificial
<220> FEATURE:
<223> OTHER INFORMATION: Synthetic peptide

<400> SEQUENCE: 530

Ser Ala Gly Ser Glu Gln Gln Leu Asp Glu Leu Leu Ala Phe Ile Ala
1               5                   10                  15

Ala Ala Leu Gln Gln
            20

<210> SEQ ID NO 531
<211> LENGTH: 21
<212> TYPE: PRT
<213> ORGANISM: Artificial
<220> FEATURE:
<223> OTHER INFORMATION: Synthetic peptide

<400> SEQUENCE: 531

Ser Gln Ala Gly Ser Glu Gln Leu Asp Leu Leu Leu Met Phe Ile Met
1               5                   10                  15

Met Met Leu Gln Gln
            20

<210> SEQ ID NO 532
<211> LENGTH: 21
<212> TYPE: PRT
<213> ORGANISM: Artificial
<220> FEATURE:
<223> OTHER INFORMATION: Synthetic peptide

<400> SEQUENCE: 532

Ala Glu Gln Gly Ser Ser Gln Leu Asp Leu Leu Leu Met Phe Ile Met

Met Met Leu Gln Gln
            20

<210> SEQ ID NO 533
<211> LENGTH: 23
<212> TYPE: PRT
<213> ORGANISM: Artificial
<220> FEATURE:
<223> OTHER INFORMATION: Synthetic peptide

<400> SEQUENCE: 533

Asn Gln Gly Ile Ser Glu Lys Gln Gln Leu Asp Leu Leu Leu Met Phe
1               5                   10                  15

Ile Met Met Met Leu Gln Gln
            20

<210> SEQ ID NO 534
<211> LENGTH: 23
<212> TYPE: PRT
<213> ORGANISM: Artificial
<220> FEATURE:
<223> OTHER INFORMATION: Synthetic peptide

<400> SEQUENCE: 534

Asn Gln Gly Ile Ser Glu Lys Gln Gln Leu Asp Leu Leu Leu Ala Phe
1               5                   10                  15

Ile Ala Ala Ala Leu Gln Gln
            20

<210> SEQ ID NO 535
<211> LENGTH: 34
<212> TYPE: PRT
<213> ORGANISM: Artificial
<220> FEATURE:
<223> OTHER INFORMATION: Synthetic peptide

<400> SEQUENCE: 535

Asn Phe Gly Thr Pro Asp Ser Thr Val Gln Asn Pro Gln Asp Ala Ser
1               5                   10                  15

Lys Pro Asn Gln Leu Asp Leu Leu Leu Met Phe Ile Met Met Met Leu
            20                  25                  30

Gln Gln

<210> SEQ ID NO 536
<211> LENGTH: 34
<212> TYPE: PRT
<213> ORGANISM: Artificial
<220> FEATURE:
<223> OTHER INFORMATION: Synthetic peptide

<400> SEQUENCE: 536

Asn Phe Gly Thr Pro Asp Ser Thr Val Gln Asn Pro Gln Asp Ala Ser
1               5                   10                  15

Lys Pro Asn Gln Leu Asp Leu Leu Leu Ala Phe Ile Ala Ala Ala Leu
            20                  25                  30

Gln Gln

<210> SEQ ID NO 537
<211> LENGTH: 30
<212> TYPE: PRT
<213> ORGANISM: Artificial
<220> FEATURE:

<223> OTHER INFORMATION: Synthetic peptide

<400> SEQUENCE: 537

Ile Thr Pro Asp Gly Gln Gly Gly Gly Gln Ile Gly Asp Asn Pro Gln
1               5                   10                  15

Leu Asp Leu Leu Leu Met Phe Ile Met Met Leu Gln Gln
            20                  25                  30

<210> SEQ ID NO 538
<211> LENGTH: 30
<212> TYPE: PRT
<213> ORGANISM: Artificial
<220> FEATURE:
<223> OTHER INFORMATION: Synthetic peptide

<400> SEQUENCE: 538

Ile Thr Pro Asp Gly Gln Gly Gly Gly Gln Ile Gly Asp Asn Pro Gln
1               5                   10                  15

Leu Asp Leu Leu Leu Ala Phe Ile Ala Ala Ala Leu Gln Gln
            20                  25                  30

<210> SEQ ID NO 539
<211> LENGTH: 20
<212> TYPE: PRT
<213> ORGANISM: Artificial
<220> FEATURE:
<223> OTHER INFORMATION: Synthetic peptide

<400> SEQUENCE: 539

Ser Glu Glu Gln Leu Asp Leu Leu Leu Ala Phe Ile Ala Ala Ala Leu
1               5                   10                  15

Gln Gln Glu Glu
            20

<210> SEQ ID NO 540
<211> LENGTH: 19
<212> TYPE: PRT
<213> ORGANISM: Artificial
<220> FEATURE:
<223> OTHER INFORMATION: Synthetic peptide

<400> SEQUENCE: 540

Ser Glu Glu Gln Leu Glu Leu Leu Leu Ala Phe Ile Ala Ala Ala Leu
1               5                   10                  15

Gln Glu Glu

<210> SEQ ID NO 541
<211> LENGTH: 21
<212> TYPE: PRT
<213> ORGANISM: Artificial
<220> FEATURE:
<223> OTHER INFORMATION: Synthetic peptide

<400> SEQUENCE: 541

Ser Ala Gly Ser Glu Glu Glu Leu Asp Leu Leu Leu Met Phe Ile Met
1               5                   10                  15

Met Met Leu Gln Gln
            20

```
<210> SEQ ID NO 542
<211> LENGTH: 21
<212> TYPE: PRT
<213> ORGANISM: Artificial
<220> FEATURE:
<223> OTHER INFORMATION: Synthetic peptide

<400> SEQUENCE: 542

Ser Ala Gly Ser Glu Gln Gln Leu Asp Leu Leu Met Phe Ile Met
1               5                   10                  15

Met Met Leu Glu Glu
            20

<210> SEQ ID NO 543
<211> LENGTH: 21
<212> TYPE: PRT
<213> ORGANISM: Artificial
<220> FEATURE:
<223> OTHER INFORMATION: Synthetic peptide

<400> SEQUENCE: 543

Ser Glu Glu Gln Gln Leu Asp Leu Leu Leu Met Phe Ile Met Met
1               5                   10                  15

Leu Gln Gln Glu Glu
            20

<210> SEQ ID NO 544
<211> LENGTH: 22
<212> TYPE: PRT
<213> ORGANISM: Artificial
<220> FEATURE:
<223> OTHER INFORMATION: Synthetic peptide

<400> SEQUENCE: 544

Ser Glu Glu Glu Glu Gln Leu Asp Gln Leu Leu Leu Ala Phe Ile Ala
1               5                   10                  15

Ala Ala Leu Gln Gln Arg
            20

<210> SEQ ID NO 545
<211> LENGTH: 15
<212> TYPE: PRT
<213> ORGANISM: Artificial
<220> FEATURE:
<223> OTHER INFORMATION: Synthetic peptide

<400> SEQUENCE: 545

Gln Leu Glu Gln Leu Leu Ala Phe Ile Ala Ala Ala Leu Gln Gln
1               5                   10                  15

<210> SEQ ID NO 546
<211> LENGTH: 15
<212> TYPE: PRT
<213> ORGANISM: Artificial
<220> FEATURE:
<223> OTHER INFORMATION: Synthetic peptide

<400> SEQUENCE: 546

Gln Leu Asp Leu Leu Leu Ala Phe Ile Ala Ala Ala Leu Gln Gln
1               5                   10                  15

<210> SEQ ID NO 547
<211> LENGTH: 5
<212> TYPE: PRT
<213> ORGANISM: Artificial
<220> FEATURE:
```

```
<223> OTHER INFORMATION: Enterokinase cleavage site

<400> SEQUENCE: 547

Asp Asp Asp Asp Lys
1               5

<210> SEQ ID NO 548
<211> LENGTH: 4
<212> TYPE: PRT
<213> ORGANISM: Artificial
<220> FEATURE:
<223> OTHER INFORMATION: Xa cleavage site
<220> FEATURE:
<221> NAME/KEY: MISC_FEATURE
<222> LOCATION: (2)..(2)
<223> OTHER INFORMATION: X at position 2 is G or D

<400> SEQUENCE: 548

Ile Xaa Gly Arg
1

<210> SEQ ID NO 549
<211> LENGTH: 6
<212> TYPE: PRT
<213> ORGANISM: Artificial
<220> FEATURE:
<223> OTHER INFORMATION: Genenase I cleavage site

<400> SEQUENCE: 549

Pro Gly Ala Ala His Tyr
1               5
```

HYPERSENSITIVE RESPONSE ELICITOR-DERIVED PEPTIDES AND USE THEREOF

This application claims the priority benefit of U.S. Provisional Patent Application Ser. No. 62/319,138, filed Apr. 6, 2016, which is hereby incorporated by reference in its entirety.

FIELD OF THE INVENTION

The present invention relates to novel hypersensitive response elicitor peptides and their use for inducing active plant responses including, among others, growth enhancement, disease resistance, pest or insect resistance, and stress resistance.

BACKGROUND OF THE INVENTION

The identification and isolation of harpin proteins came from basic research at Cornell University attempting to understand how plant pathogenic bacteria interact with plants. A first line of defense is the hypersensitive response (HR), a localized plant cell death at the site of infection. Cell death creates a physical barrier to movement of the pathogen and in some plants dead cells can release compounds toxic to the invading pathogen. Research had indicated that pathogenic bacteria were likely to have a single factor that was responsible for triggering the HR. A basic aim of the Cornell research was to identify a specific bacterial protein responsible for eliciting the HR. The target protein was known to be encoded by one of a group of bacteria genes called the Hypersensitive Response and Pathogenicity (hrp) gene cluster. The hrp cluster in the bacterium *Erwinia amylovora* (Ea), which causes fire blight in pear and apple, was dissected and a single protein was identified that elicited HR in certain plants. This protein was given the name harpin (and, later, harpin$_{Ea}$ and the corresponding gene designated hrpN. This was the first example of such a protein and gene identified from any bacterial species.

A number of different harpin proteins have since been identified from *Erwinia*, *Pseudomonas*, *Ralstonia*, *Xanthomonas*, and *Pantoea* species, among others. Harpin proteins, while diverse at the primary amino acid sequence level, share common biochemical and biophysical characteristics as well as biological functions. Based on their unique properties, the harpin proteins are regarded in the literature as belonging to a single class of proteins.

Subsequent to their identification and isolation, it was thereafter discovered that harpins could elicit disease resistance in plants and increase plant growth. An important early finding was that application of purified harpin protein made a plant resistant to a subsequent pathogen attack, and in locations on the plant well away from the injection site. This meant that harpin proteins can trigger a Systemic Acquired Resistance (SAR), a plant defense mechanism that provides resistance to a variety of viral, bacterial, and fungal pathogens.

In crop protection, there is a continuous need for compositions that improve the health of plants. Healthier plants are desirable since they result in better yields and/or a better quality of the plants or crops. Healthier plants also better resist biotic and abiotic stress. A high resistance against biotic stresses in turn allows the growers to reduce the quantity of pesticides applied and consequently to slow down the development of resistances against the respective pesticides.

Harpin$_{\alpha\beta}$ is a fusion protein that is derived from several different harpins. Harpin$_{\alpha\beta}$ has been shown to suppress nematode egg production, enhance the growth, quality and yield of a plant, and increase a plant's vigor. Its amino acid and nucleotide sequences are described in detail in U.S. Application Publ. No. 2010/0043095.

To date, harpin and harpin$_{\alpha\beta}$ production and their use in agricultural and horticultural applications have been as a powdered solid coated on starch. This limits the use and versatility of the harpin proteins, because liquid suspensions of the powdered harpin proteins in water have an effective useful life of only 48-72 hours before significant degradation and loss of activity occurs. Another problem with harpin solutions is protein solubility and stability.

It would be desirable to identify synthetic and derivative harpin peptides that are readily soluble in aqueous solution, stable, resistant to chemical degradation, and effective in initiating one or more active plant responses including, without limitation, the hypersensitive plant response.

The present invention is directed to overcoming these and other limitations in the art.

SUMMARY OF THE INVENTION

A first aspect of the invention relates to an isolated peptide comprising the amino acid sequence of (i)
```
                                            (SEQ ID NO: 1)
(L/I/V/F)-X-X-(L/I/V/F)-(L/I/V/F)-(L/I/V/F)-X-
(L/I/V/F)-(L/I/V/F)-X-X-X-(L/I/V/F),
```
or (ii)
```
                                            (SEQ ID NO: 2)
L-X-X-L-L-L-X-(F/L)-(I/L)-X-X-X-L,
``` wherein for both SEQ ID NO: 1 and 2, X at position 3 is optional and, when present, is any amino acid; and each X at positions 2, 7, 10, 11, and 12 is any amino acid. In one embodiment, X at position 3 is present. In another embodiment, X at position 3 is not present. In other embodiments, the isolated peptide is free of cysteine or free of both cysteine and methionine. In certain embodiments, the isolated peptide further includes a hydrophilic amino acid sequence that is located N-terminal or C-terminal to SEQ ID NO: 1 or SEQ ID NO: 2.

One set of peptides according to the first aspect of the invention have the amino acid sequence of:

```
                                            (SEQ ID NO: 3)
(Q/E)-(Q/E)-(L/I/V/F)-X-X-(L/I/V/F)-(L/I/V/F)-
(L/I/V/F)-X-(L/I/V/F)-(L/I/V/F)-X-X-X-(L/I/V/F)-
(D/G/Q/E)-(D/G/Q/E),,
``` wherein X at position 5 is optional and, when present, is any amino acid; and each X at positions 4, 9, 12, 13, and 14 is any amino acid. In one embodiment, X at position 5 is present. In another embodiment, X at position 5 is not present.

Another set of peptides according to the first aspect of the invention have the amino acid of:

(L/I/V/F)-X-X-(L/I/V/F)-(L/IN/V/F)-(L/I/V/F)-X-
(L/I/V/F)-(L/I/V/F)-X-X-X-(L/I/V/F)-(D/G/Q/E)-
(D/G/Q/E), ,
(SEQ ID NO: 4)

wherein X at position 3 is optional and, when present, is any amino acid; and each X at positions 2, 7, 10, 11, and 12 is any amino acid. In one embodiment, X at position 3 is present. In another embodiment, X at position 3 is not present.

A further set of peptides according to the first aspect of the invention have the amino acid sequence of:

(Q/E)-(Q/E)-(L/I/V/F)-X-X-(L/I/V/F)-(L/I/V/F)-
(L/I/V/F)-X-(L/I/V/F)-(L/I/V/F)-X-X-X-(L/I/V/F), ,
(SEQ ID NO: 5)

wherein X at position 5 is optional and, when present, is any amino acid; and each X at positions 4, 9, 12, 13, and 14 is any amino acid. In one embodiment, X at position 5 is present. In another embodiment, X at position 5 is not present.

A second aspect of the invention relates to an isolated peptide comprising the amino acid sequence of

J-X-X-J-J-J-X-J-J-X-X-X-J
(SEQ ID NO: 6)

wherein X at position 3 is optional and, when present, is any amino acid; and each X at positions 2, 7, 10, 11, and 12 is any amino acid; one to three of the J residues at positions 1, 4, 5, 6, 8, 9, and 13 is a non-hydrophobic amino acid or A, and all other of the J residues are L, I, V, or F, and the peptide induces an active plant response, but does not induce a hypersensitive response, when applied to plant tissue.

A third aspect of the invention relates to a fusion protein that includes one of the peptides of the first or second aspect of the invention along with one or more of a purification tag, a solubility tag, or a second peptide according to the first or second aspect of the invention.

A fourth aspect of the invention relates to a composition that includes one or more peptides according to the first or second aspect of the invention, or a fusion protein according to the third aspect of the invention, and a carrier.

A fifth aspect of the invention relates to a method of imparting disease resistance to plants. This method includes: applying an effective amount of an isolated peptide according to the first or second aspect of the invention, a fusion protein according to the third aspect of the invention, or a composition according to the fourth aspect of the invention to a plant or plant seed or the locus where the plant is growing or is expected to grow, wherein said applying is effective to impart disease resistance.

A sixth aspect of the invention relates to a method of enhancing plant growth. This method includes: applying an effective amount of an isolated peptide according to the first or second aspect of the invention, a fusion protein according to the third aspect of the invention, or a composition according to the fourth aspect of the invention to a plant or plant seed or the locus where the plant is growing or is expected to grow, wherein said applying is effective to enhance plant growth.

A seventh aspect of the invention relates to a method of increasing a plant's tolerance and resistance to biotic stressors. This method includes: applying an effective amount of an isolated peptide according to the first or second aspect of the invention, a fusion protein according to the third aspect of the invention, or a composition according to the fourth aspect of the invention to a plant or plant seed or the locus where the plant is growing or is expected to grow, wherein said applying is effective to increase the plant's tolerance and resistance to biotic stress factors selected from the group consisting of pests such as insects, arachnids, nematodes, weeds, and combinations thereof.

An eighth aspect of the invention relates to a method of increasing a plant's tolerance to abiotic stress. This method includes: applying an effective amount of an isolated peptide according to the first or second aspect of the invention, a fusion protein according to the third aspect of the invention, or a composition according to the fourth aspect of the invention to a plant or plant seed or the locus where the plant is growing or is expected to grow, wherein said applying is effective to increase the plant's tolerance to abiotic stress factors selected from the group consisting of salt stress, water stress (including drought and flooding), ozone stress, heavy metal stress, cold stress, heat stress, nutritional stress (phosphate, potassium, nitrogen deficiency), bleaching and light-induced stress, and combinations thereof.

A ninth aspect of the invention relates to a method imparting desiccation resistance to cuttings removed from ornamental plants. This method includes: applying an isolated peptide according to the first or second aspect of the invention, a fusion protein according to the third aspect of the invention, or a composition according to the fourth aspect of the invention to a plant or the locus where the plant is growing, wherein said applying is effective to impart desiccation resistance to cuttings removed from the ornamental plant.

A tenth aspect of the invention relates to a method of imparting post-harvest disease or post-harvest desiccation resistance to a fruit or vegetable. This method includes: applying an effective amount of an isolated peptide according to the first or second aspect of the invention, a fusion protein according to the third aspect of the invention, or a composition according to the fourth aspect of the invention to a plant containing a fruit or vegetable or the locus where the plant is growing; or applying an effective amount of the isolated peptide, the fusion protein, or the composition to a harvested fruit or vegetable, wherein said applying is effective to impart post-harvest disease resistance or desiccation resistance to the fruit or vegetable.

An eleventh aspect of the invention relates to a method of enhancing the longevity of fruit or vegetable ripeness. This method includes: applying an effective amount of an isolated peptide according to the first or second aspect of the invention, a fusion protein according to the third aspect of the invention, or a composition according to the fourth aspect of the invention to a plant containing a fruit or vegetable or the locus where the plant is growing; or applying an effective amount of the isolated peptide, the fusion protein, or the composition to a harvested fruit or vegetable, wherein said applying is effective to enhance the longevity of fruit or vegetable ripeness.

A twelfth aspect of the invention relates to a method of modulating one or more biological signaling processes of a plant. This method includes: applying an effective amount of an isolated peptide according to the first or second aspect of the invention, a fusion protein according to the third aspect of the invention, or a composition according to the fourth aspect of the invention to a plant or the locus where the plant is growing, wherein said applying is effective in modulating one or more biochemical signaling processes.

A thirteenth aspect of the invention relates to a DNA construct including a first nucleic acid molecule encoding a polypeptide according to the first or second aspect of the invention or a fusion protein according to the third aspect of the invention; and a promoter-effective nucleic acid molecule operably coupled to the first nucleic acid molecule. This aspect of the invention also encompasses a recombinant expression vector containing the DNA construct, a recombinant host cell containing the DNA construct, as well as transgenic plants or plant seeds that include a recombinant plant cell of the invention (which contains the DNA construct).

A fourteenth aspect of the invention relates to a method of imparting disease resistance to plants, enhancing plant growth, imparting tolerance and resistance to biotic stressors, imparting tolerance to abiotic stress, or modulating plant biochemical signaling. This method includes providing a transgenic plant transformed with a DNA construct according to the thirteenth aspect of the invention; and growing the plant under conditions effective to permit the DNA construct to express the peptide or the fusion polypeptide to impart disease resistance, enhance plant growth, impart tolerance to biotic stress, impart tolerance to abiotic stress, or modulate biochemical signaling to the transgenic plant.

A fifteenth aspect of the invention relates to a method of imparting desiccation resistance to cuttings removed from ornamental plants, imparting post-harvest disease or post-harvest desiccation resistance to a fruit or vegetable, or enhancing the longevity of fruit or vegetable ripeness. The method includes providing a transgenic plant transformed with a DNA construct including a first nucleic acid molecule encoding a polypeptide according to the first or second aspect of the invention or a fusion protein according to the third aspect of the invention; and growing the plant under conditions effective to permit the DNA construct to express the peptide or the fusion polypeptide to impart desiccation resistance to cuttings removed from a transgenic ornamental plant, impart post-harvest disease resistance or desiccation resistance to a fruit or vegetable removed from the transgenic plant, or enhance longevity of ripeness for a fruit or vegetable removed from the transgenic plant.

A sixteenth aspect of the invention relates to a method of imparting disease resistance to plants, enhancing plant growth, imparting tolerance and resistance to biotic stressors, imparting tolerance to abiotic stress, or modulating biochemical signaling. This method includes providing a transgenic plant seed transformed with a DNA construct according to the thirteenth aspect of the invention; planting the transgenic plant seed in soil; and propagating a transgenic plant from the transgenic plant seed to permit the DNA construct to express the peptide or the fusion polypeptide to impart disease resistance, enhance plant growth, impart tolerance to biotic stress, or impart tolerance to abiotic stress to the transgenic plant.

A seventeenth aspect of the invention relates to a method of imparting desiccation resistance to cuttings removed from ornamental plants, imparting post-harvest disease or post-harvest desiccation resistance to a fruit or vegetable, or enhancing the longevity of fruit or vegetable ripeness. The method includes providing a transgenic plant seed transformed with a DNA construct according to the thirteenth aspect of the invention; planting the transgenic plant seed in soil; and propagating a transgenic plant from the transgenic plant seed to permit the DNA construct to express the peptide or the fusion polypeptide to impart desiccation resistance to cuttings removed from a transgenic ornamental plant, impart post-harvest disease resistance or desiccation resistance to a fruit or vegetable removed from the transgenic plant, or enhance longevity of ripeness for a fruit or vegetable removed from the transgenic plant.

By providing HR-eliciting peptides and active but non-HR-eliciting peptides that exhibit improved solubility, stability, resistance to chemical degradation, or a combination of these properties, it will afford growers with greater flexibility in preparing, handling, and delivering to plants in their fields or greenhouses effective amounts of compositions containing these HR-eliciting and non-HR-eliciting peptides. Simplifying the application process for growers will lead to greater compliance and, thus, improved results with respect to one or more of disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These and other benefits are described herein, and the utility of these peptides is demonstrated by the accompanying Examples where resistance to tobacco mosaic virus was shown in tobacco, resistance to nematodes was demonstrated in soy and tomato, and drought resistance was demonstrated in soy and corn.

DETAILED DESCRIPTION OF THE INVENTION

Figure 1:
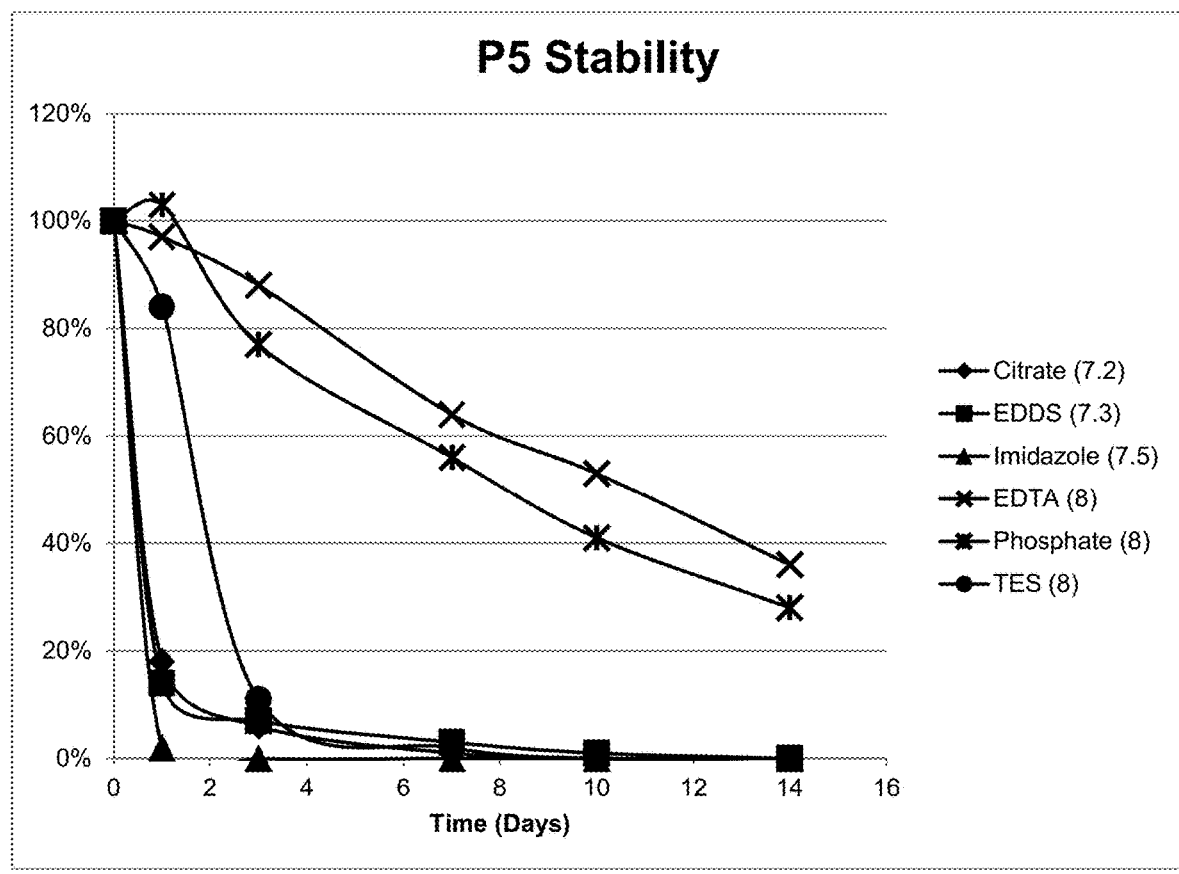
FIG. 1 shows a solubility and stability test of peptide P5 (SEQ ID NO: 8) in the following 50 mM buffer solutions: citrate, pH 7.2; EDDS, pH 7.3; imidazole, pH 7.5; EDTA, pH 8.0; sodium phosphate, pH 8.0; and TES, pH 8.0. Peptide P5 exhibited poor solubility below pH 7.0, and exhibited its best results in an EDTA buffer at pH 8.0 (about 40% remaining after 14 days).

One aspect of the invention relates to novel peptides that possess the ability to either induce a hypersensitive response in plants or promote active plant responses (or both) that afford one or more of the following attributes: disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. The induction of these plant responses involves modulating plant biochemical signaling.

As used herein, naturally occurring amino acids are identified throughout by the conventional three-letter and/or one-letter abbreviations, corresponding to the trivial name of the amino acid, in accordance with the following list: Alanine (Ala, A), Arginine (Arg, R), Asparagine (Asn, N), Aspartic acid (Asp, D), Cysteine (Cys, C), Glutamic acid (Glu, E), Glutamine (Gln, Q), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). The abbreviations are accepted in the peptide art and are recommended by the IUPAC-IUB commission in biochemical nomenclature. Naturally occurring variations of these amino acids are well known and include, without limitation, gamma-glutamate (g-Glu) and isoaspartate (iso-Asp or isoD).

The term "amino acid" further includes analogues, derivatives, and congeners of any specific amino acid referred to herein, as well as C-terminal or N-terminal protected amino acid derivatives (e.g., modified with an N-terminal, C-terminal, or side-chain protecting group, including but not limited to acetylation, formylation, methylation, amidation, esterification, PEGylation, and addition of lipids. Non-naturally occurring amino acids are well known and can be introduced into peptides of the present invention using solid phase synthesis as described below. Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations. In one embodiment, a peptide comprises all L-amino acids.

In certain embodiments, peptides are identified to "consist of" a recited sequence, in which case the peptide includes only the recited amino acid sequence(s) without any extraneous amino acids at the N- or C-terminal ends thereof. To the extent that a recited sequence is in the form of a consensus sequence where one or more of the denoted X or Xaa residues can be any of one or more amino acids, then multiple peptide sequences are embraced by a peptide consisting of such a recited sequence.

In certain other embodiments, peptides are identified to "consist essentially of" a recited sequence, in which case the peptide includes the recited amino acid sequence(s) optionally with one or more extraneous amino acids at the N- and/or C-terminal ends thereof, which extraneous amino acids do not materially alter one or more of the following properties: (i) the ability of the peptide to induce a hypersensitive response or other active response in plants, (ii) solubility of the peptide in water or aqueous solutions, (iii) stability of the peptide dissolved in water or aqueous solution at 50° C. over a period of time (e.g., 3 weeks), and (iv) resistance of the peptide to chemical degradation in the presence of an aqueous buffered solution that includes a biocidal agent (e.g., Proxel®GXL) at 50° C. over a period of time (e.g., 3 weeks).

Briefly, the stability and resistance to chemical degradation of peptides can be assessed as follows using peptide samples having an initial purity of at least about 80%, at least about 82%, at least about 84%, at least about 86%, at least about 88%, at least about 90%, at least about 92%, at least about 94%, at least about 96%, or at least about 98%. For water stability, the peptide is dissolved directly in de-ionized water. For chemical degradation tests, the peptide is dissolved in an aqueous solution containing 50 mM pH buffer and 0.25% Proxel GXL. Exemplary pH buffers include, without limitation: (i) Citrate pH 5.6; (ii) MES pH 6.0; (iii) MOPS pH 6.5; (iv) imidazole pH 7.5; (v) Citrate pH 7.2; (vi) EDDS, pH 7.3; (vii) EDTA pH 8.0; (viii) sodium phosphate pH 8.0; or (ix) TES pH 8.0. Peptides are first dissolved in the aqueous solution at a concentration of 0.5 mg/ml. The samples are incubated at 50° C. to allow for accelerated degradation. An initial sample of the peptide is removed, diluted 10× with water, and analyzed by reverse-phase HPLC. Briefly, 20 µl of the sample is injected into the solvent flow of an HPLC instrument and analyzed on a C18 HPLC column (YMC ProPack C18, YMC, Japan, or C18 Stablebond, Agilent Technologies, USA) using either a triethylamine phosphate in water/acetonitrile gradient or a 0.1% TFA in water/0.1% TFA in acetonitrile gradient to separate different peptide species. Eluting peptides are monitored by UV absorbance at 218 nm and quantified based on the area under the peak. The area under the peak for the initial peptide sample is treated as the standard for relative quantification in subsequent runs. At regular intervals (e.g., 1, 3, 7, 10, and 14 days), each peptide sample is surveyed and analyzed by HPLC as described above. If necessary to observe degradation (i.e., where the peptide exhibits a high degree of chemical stability), this protocol can be extended by several weeks to observe degradation. The quantification of subsequent peptide runs is expressed as a percentage of the original (day 0) HPLC result.

A peptide that is at least partially soluble in water or aqueous solution exhibits a solubility of greater than 0.1 mg/ml, preferably at least about 1.0 mg/ml, at least about 2.0 mg/ml, at least about 3.0 mg/ml, or at least about 4.0 mg/ml. In certain embodiments, the peptide exhibits high solubility in water or aqueous solution, with a solubility of at least about 5.0 mg/ml, at least about 10.0 mg/ml, at least about 15.0 mg/ml, or at least about 20 mg/ml.

A peptide that is stable in water or aqueous solution exhibits at least about 66%, at least about 68%, at least about 70%, at least about 72%, at least about 74%, at least about 76%, at least about 78%, at least about 80%, at least about 82%, at least about 84%, at least about 86%, at least about 88%, or at least about 90% of the original peptide concentration over the designated period of time incubated at 50° C. In certain embodiments, the designated period of time is 3 days, 7 days, 14 days, 21 days, 28 days, one month, two months, three months, or four months.

A peptide that is resistant to chemical degradation exhibits at least about 66%, at least about 68%, at least about 70%, at least about 72%, at least about 74%, at least about 76%, at least about 78%, at least about 80%, at least about 82%, at least about 84%, at least about 86%, at least about 88%, or at least about 90% of the original peptide concentration over the designated period of time incubated at 50° C. In certain embodiments, the designated period of time is 3 days, 7 days, 14 days, 21 days, 28 days, one month, two months, three months, or four months.

A property of a peptide to elicit a hypersensitive response, or not, upon infiltration or application of the peptide to plant tissues can be measured by applying the peptide in dry powder form or in solution form to a plant, particularly though not exclusively a plant leaf. Application rates include 1-500 ug/ml for liquid solution and 0.0001-0.5% (w/w for powder application. Exemplary application of the peptide in solution form is described in the accompanying Examples. Plants are considered HR-positive ("HR+") if they exhibit wide-spread macroscopic cell death visible to the naked eye, accompanied by wilting and browning of the affected tissue within 48 hours. Plants are considered HR-negative ("HR−") if they exhibit no discernible wilting or tissue death observable by naked eye.

In certain embodiments, material alteration of the one or more properties is intended to mean that there is less than 20% variation, less than 15% variation, less than 10% variation, or less than 5% variation in a recited property when comparing a peptide possessing the one or more extraneous amino acids to an otherwise identical peptide lacking the one or more extraneous amino acids. In certain embodiments, the number of extraneous amino acids at the N- or C-terminal ends is up to 20 amino acids at one or both ends, up to 15 amino acids at one or both ends, up to 10 amino acids at one or both ends, up to 7 amino acids at one or both ends, up to 5 amino acids at one or both ends, or up to 3 amino acids at one or both ends. Further, to the extent that a recited sequence is in the form of a consensus sequence where one or more of the denoted X or Xaa residues can be any of one or more amino acids, then multiple peptide sequences are embraced by the peptide consisting essentially of such a recited sequence, without regard to additional variations of such sequences that are afforded by the presence of extraneous amino acids at the N- and/or C-terminal ends thereof.

In various embodiments of the invention, the disclosed peptides may include a hydrophilic amino acid sequence, e.g., at either the N-terminal or C-terminal end of a designated peptide sequence. The hydrophilic amino acid sequence is at least 3, at least 4, at least 5, at least 6, at least 7, at least 8, at least 9, or at least 10 amino acids in length, and includes amino acid residues that contribute to a hydrophilic property of the amino acid sequence that is adjacent to the amino acid sequence of the designated peptide (i.e., the peptide that induces an active plant response). Different methods have been used in the art to calculate the relative hydrophobicity/hydrophilicity of amino acid residues and proteins (Kyte et al., "A Simple Method for Displaying the Hydropathic Character of a Protein," *J. Mol. Biol.* 157: 105-32 (1982); Eisenberg D, "Three-dimensional Structure of Membrane and Surface Proteins," *Ann. Rev. Biochem.* 53: 595-623 (1984); Rose et al., "Hydrogen Bonding, Hydrophobicity, Packing, and Protein Folding," *Annu. Rev. Biomol. Struct.* 22: 381-415 (1993); Kauzmann, "Some Factors in the Interpretation of Protein Denaturation," *Adv. Protein Chem.* 14: 1-63 (1959), which are hereby incorporated by reference in their entirety). Any one of these hydrophobicity scales can be used for the purposes of the present invention; however, the Kyte-Doolittle hydrophobicity scale is perhaps the most often referenced scale. These hydropathy scales provide a ranking list for the relative hydrophobicity of amino acid residues. For example, amino acids that contribute to hydrophilicity include Arg (R), Lys (K), Asp (D), Glu (E), Gln (Q), Asn (N), and His (H) as well as, albeit to a lesser extent, Ser (S), Thr (T), Gly (G), Pro (P), Tyr (Y), and Trp (W). For example, polyglutamate sequences can be used to enhance solubility of proteins and other drug molecules (Lilie et al, *Biological Chemistry* 394(8):995-1004(2013); Li et al., *Cancer Research* 58: 2404-2409(1998)), each of which is hereby incorporated by reference in its entirety).

The "hydropathy index" of a protein or amino acid sequence is a number representing its average hydrophilic or hydrophobic properties. A negative hydropathy index defines the hydrophilicity of the amino acid sequence of interest. The hydropathy index is directly proportional to the hydrophilicity of the amino acid sequence of interest; thus, the more negative the index, the greater its hydrophilicity. In certain embodiments, the added hydrophilic amino acid sequence described above has a hydropathy index of less than 0, −0.4, −0.9, −1.3, −1.6, −3.5, −3.9, or −4.5. In certain embodiments, the resulting entire peptide will have a hydropathy index of less than 0.7, 0.3, 0.2, 0.1, or 0.0, preferably less than −0.1, −0.2, −0.3, −0.4, more preferably less than −0.5, −0.6, −0.7, −0.8, −0.9, or −1.0.

In the peptides of the present invention, amino acids that contribute to a hydrophilic hydropathy index, for either the peptide as a whole or the added hydrophilic amino acid sequence, include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

As used herein, in this and in other aspects of the invention, the term "hydrophobic amino acid" is intended to refer to an amino acid that contributes hydrophobicity to the hydropathy index of a designated amino acid sequence. Amino acids that contribute to a hydrophobic hydropathy index, for either the peptide as a whole or a particular amino acid sequence thereof, include Ile (I), Val (V), Leu (L), Phe (F), Cys (C), Met (M), and Ala (A). In certain embodiments, the term "hydrophobic amino acid" may refer to any one of Ile (I), Val (V), Leu (L), Phe (F), Cys (C), Met (M), and Ala (A); or, alternatively, to any one of Ile (I), Val (V), Leu (L), Phe (F), and Ala (A). In certain other embodiments, the term "hydrophobic amino acid" may refer to one of Ile (I), Val (V), Leu (L), and Phe (F).

As used herein, the term "non-hydrophobic amino acid" is intended to mean an amino acid that is hydrophilic (or not hydrophobic) on one of the above-identified hydrophobicity scales. This term generally refers to those amino acids that contribute to a hydrophilic hydropathy index for either the peptide as a whole or the added hydrophilic amino acid sequence.

In one aspect of the invention, the peptide includes the amino acid sequence of:

```
(i)
                                            (SEQ ID NO: 1)
(L/I/V/F)-X-X-(L/I/V/F)-(L/I/V/F)-(L/I/V/F)-X-
(L/I/V/F)-(L/I/V/F)-X-X-X-(L/I/V/F),
or
(ii)
                                            (SEQ ID NO: 2)
L-X-X-L-L-L-X-(F/L)-(I/L)-X-X-X-L,
``` wherein X for both SEQ ID NO: 1 and 2 at position 3 is optional and, when present, is any amino acid; and each X at positions 2, 7, 10, 11, and 12 is any amino acid.

In a related aspect of the invention, the peptide includes the amino acid sequence of SEQ ID NO: 1 or 2 (shown above), wherein the peptide is free of cysteine or free of both cysteine and methionine; X at position 3 is optional and, when present, is any amino acid; and each X at positions 2, 7, 10, 11, and 12 is any amino acid.

According to one embodiment, X at position 3 is not present (i.e., the gap between the first hydrophobic amino acid and the first hydrophobic amino acid triplet is reduced from two to one amino acid residue. In this embodiment, it is contemplated that these peptides exclude the amino acid at only position 3.

In an alternative embodiment, X at position 3 is present (i.e., the gap between the hydrophobic amino acids is maintained at two amino acid residues).

The peptide length in this embodiment is less than 100 amino acids, or alternatively less than 90 amino acids, less than 80 amino acids, less than 70 amino acids, less than 60 amino acids, or less than about 50 amino acids. In certain embodiments, the peptide length is between 12 and about 50 amino acids in length.

In the embodiments described above, where X at each of positions 2, 3 (when present), 7, 10, 11, and 12 of SEQ ID NO: 1 and 2 can be any amino acid, in certain embodiments these residues are hydrophilic in nature. As described above, these hydrophilic amino acids include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

In certain embodiments, X at positions 2 and 3 (when present) is selected independently from Asp (D), Glu (E), and Gln (Q).

In certain embodiments, X at positions 7, 10, 11, and 12 is selected independently from Ala (A), Met (M), Gly (G), Ser (S), and Glu (E).

In this embodiment, the isolated peptide is stable when dissolved in water; resistant to chemical degradation in aqueous conditions in the presence of a pH buffer and a biocide, as described above; and/or has a solubility in an aqueous solution of at least about 1.0 mg/ml.

One set of peptides according to the first aspect of the invention have the amino acid sequence of:

```
                                               (SEQ ID NO: 3)
(Q/E)-(Q/E)-(L/I/V/F)-X-X-(L/I/V/F)-(L/I/V/F)-

(L/I/V/F)-X-(L/I/V/F)-(L/I/V/F)-X-X-X-(L/I/V/F)-

(D/G/Q/E)-(D/G/Q/E),,
``` wherein X at position 5 is optional and, when present, is any amino acid; and each X at positions 4, 9, 12, 13, and 14 is any amino acid. In one embodiment, X at position 5 is present. In another embodiment, X at position 5 is not present.

In the embodiments described above, where X at each of positions 4, 5 (when present), 9, 12, 13, and 14 of SEQ ID NO: 3 can be any amino acid, in certain embodiments these residues are hydrophilic in nature. As described above, these hydrophilic amino acids include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

In certain embodiments, X at positions 4 and 5 (when present) is selected independently from Asp (D), Glu (E), and Gln (Q).

In certain embodiments, X at positions 9 and 12 to 14 is selected independently from Ala (A), Met (M), Gly (G), Ser (S), and Glu (E).

In certain embodiments, these peptides also meet the structural features defining the peptides of SEQ ID NO: 1, in which case methionine and cysteine residues are not present.

Another set of peptides according to the first aspect of the invention have the amino acid of:

```
                                               (SEQ ID NO: 4)
(L/I/V/F)-X-X-(L/I/V/F)-(L/I/V/F)-(L/I/V/F)-X-

(L/I/V/F)-(L/I/V/F)-X-X-X-(L/I/V/F)-(D/G/Q/E)-

(D/G/Q/E),,
``` wherein X at position 3 is optional and, when present, is any amino acid; and each X at positions 2, 7, 10, 11, and 12 is any amino acid. In one embodiment, X at position 3 is present. In another embodiment, X at position 3 is not present.

In the embodiments described above, where X at each of positions 2, 3 (when present), 7, 10, 11, and 12 of SEQ ID NO: 4 can be any amino acid, in certain embodiments these residues are hydrophilic in nature. As described above, these hydrophilic amino acids include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

In certain embodiments, X at positions 2 and 3 (when present) is selected independently from Asp (D), Glu (E), and Gln (Q).

In certain embodiments, X at positions 7, 10, 11, and 12 is selected independently from Ala (A), Met (M), Gly (G), Ser (S), and Glu (E).

A further set of peptides according to the first aspect of the invention have the amino acid sequence of:

```
                                               (SEQ ID NO: 5)
(Q/E)-(Q/E)-(L/I/V/F)-X-X-(L/I/V/F)-(L/I/V/F)-

(L/I/V/F)-X-(L/I/V/F)-(L/I/V/F)-X-X-X-(L/I/V/F),,
``` wherein X at position 5 is optional and, when present, is any amino acid; and each X at positions 4, 9, 12, 13, and 14 is any amino acid. In one embodiment, X at position 5 is present. In another embodiment, X at position 5 is not present.

In the embodiments described above, where X at each of positions 4, 5 (when present), 9, 12, 13, and 14 of SEQ ID NO: 3 can be any amino acid, in certain embodiments these residues are hydrophilic in nature. As described above, these hydrophilic amino acids include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

In certain embodiments, X at positions 4 and 5 (when present) is selected independently from Asp (D), Glu (E), and Gln (Q).

In certain embodiments, X at positions 9 and 12 to 14 is selected independently from Ala (A), Met (M), Gly (G), Ser (S), and Glu (E).

Another aspect of the invention relates to an isolated peptide comprising the amino acid sequence of

```
                                               (SEQ ID NO: 6)
                       J-X-X-J-J-J-X-J-J-X-X-X-J
``` wherein X at position 3 is optional and, when present, is any amino acid; and each X at positions 2, 7, 10, 11, and 12 is any amino acid; one to three of the J residues at positions 1, 4, 5, 6, 8, 9, and 13 is a non-hydrophobic amino acid or A, and all other of the J residues are L, I, V, or F, and the peptide induces an active plant response, but does not induce a hypersensitive response, when applied to plant tissue. These active plant responses afford one or more of the following attributes: modified biochemical signaling; enhanced growth; pathogen resistance; and/or biotic or abiotic stress resistance.

In the embodiments described above, where X at each of positions 2, 3 (when present), 7, 10, 11, and 12 of SEQ ID NO: 6 can be any amino acid, in certain embodiments these residues are hydrophilic in nature. As described above, these hydrophilic amino acids include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

In certain embodiments, X at positions 2 and 3 (when present) is selected independently from Asp (D), Glu (E), and Gln (Q).

In certain embodiments, X at positions 7, 10, 11, and 12 is selected independently from Ala (A), Met (M), Gly (G), Ser (S), and Glu (E).

In this embodiment, the isolated peptide is stable when dissolved in water; resistant to chemical degradation in aqueous conditions in the presence of a pH buffer and a biocide, as described above; and/or has a solubility in an aqueous solution of at least about 1.0 mg/ml.

Exemplary peptides that meet the consensus structure of one or more of SEQ ID NO: 1 to 6 are identified in Table 1 and Table 2 below:

TABLE 1

Peptide Variants of Peptide P5/P5A
(SEQ ID NOS: 8 and 9)

| Peptide Name | Sequence | SEQ ID NO: |
|---|---|---|
| wildtype | SAGSEQQLDQLLAMFIMMMLQQ | 7 |
| P5 | SAGSEQQLDLLLMFIMMMLQQ | 8 |
| P5A | SAGSEQQLDQLLLMFIMMMLQQ | 9 |
| P5-2 | SAGSEQQLDLLLMFIAAALQQ | 10 |
| P5-3 | SAGSEQQLDLLLAFIAAALQQ | 11 |
| P5-4 | SAGSEQQLELLLAFIAAALQQ | 12 |
| P5-7 | SEEEEELDLLLAFIAAAL | 13 |
| P5-8 | SEEEEELDLLLAFIAAALQQ | 14 |
| P5-9 | LDLLLAFIAAALEEEEEE | 15 |
| P5-10 | LDLLLAFIEEELEEEE | 16 |
| P5-11 | SEEELDLLLAFIAAALEE | 17 |
| P5-12 | SEEELDLLLAFIEEELEE | 18 |
| P5-13 | SEEELDLLLAFIAAALDD | 19 |
| P5-14 | SEEEEELDLLLAFIAAALGG | 20 |
| P5-1000 | SEEEEEEELDLLLAFIAAALAA | 21 |
| P5-1001 | SEEEEEELDLLLAFIAAALSS | 22 |
| P5-1002 | SAGSEQQLDLLLGFIGGGLQQ | 23 |
| P5-1003 | SAGSEQQLDLLLSFISSSLQQ | 24 |
| P5-15 | SEEEEELDLLLAFIAAALQ | 25 |
| P5-16 | SEEEEELDLLLAFIAAALS | 26 |
| P5-17 | SEEEEELDLLLAFIAAALA | 27 |
| P5-18 | SEEEEELDLLLAFIAAALE | 28 |
| P5-19 | SELELLLAFIAAALEEEEE | 29 |
| P5-22 | SEEELELLLAFIAAALEEEE | 30 |
| P5-1004 | SELDLLLAFIAAALEEEEE | 31 |
| P5-1005 | SEEEEELDLLLALIAAALQQ | 32 |
| P5-21 | SEEQLELLLAFIAAALQQEE | 33 |

TABLE 1-continued

Peptide Variants of Peptide P5/P5A
(SEQ ID NOS: 8 and 9)

| Peptide Name | Sequence | SEQ ID NO: |
|---|---|---|
| P5-26 | SEEQLDLLLAFIAAALQEE | 34 |
| P5-1006 | SELELLLAFIEEELEE | 35 |
| P5-20 | SELELLLEFIEEELEE | 36 |
| P5-1007 | SELELLLEFIEEELE | 37 |
| P5-1008 | SELELLLELIEEELE | 38 |
| P5-48 | *SE*EQLDLLLEFIEEELQQ*EE* | 39 |
| P5-1009 | SELDLLLAFIDDDLEE*EEE* | 40 |
| P5-29 | *SE*EELDLLLMFIMMMLEE | 42 |
| P5-31 | *SEE*EQLDLLLMFIMMMLEE | 43 |
| P5-33 | *SEE*EQLDLLLMFIMMMLQEE | 44 |
| P5-47 | *SEE*QLDLLLMFIMMMLQQ*EE* | 45 |
| P5-1010 | LELLLEFIEEELE | 46 |
| P5-1011 | LELLLEFIEEELEE | 47 |
| P5-1012 | SELELLLEFIEEEL | 48 |
| P5A variant | LDQLLLMFIMMMLQQ | 49 |
| P5-23 | *SEEEE*ELDQLLLAFIAAALQQ | 50 |
| P5-24 | *SEEEE*ELDQLLLAFIAAAL | 51 |
| P5-25 | *SEEE*EQLDQLLLAFIAAALQQ | 52 |
| P5-27 | *SEE*QLDQLLLAFIAAALQE*E* | 53 |
| P5-28 | SEEQLDQLLLAFIAAALEE | 54 |
| P5-30 | SEEELDQLLLMFIMMMLEE | 55 |
| P5-32 | SEEEQLDQLLLMFIMMMLEE | 56 |
| P5-34 | SEEEQLDQLLLMFIMMMLQEE | 57 |
| P5-46 | *SEE*QLDQLLLMFIMMMLQQ*EE* | 58 |
| P5A variant M to A | LDQLLLAFIAAALQQ | 59 |
| P5A variant M to E | LDQLLLEFIEEELQQ | 60 |
| P5A variant | QLDQLLLMFIMMMLQQ | 61 |
| P5A variant M to A | QLDQLLLAFIAAALQQ | 62 |
| P5A variant M to E | QLDQLLLEFIEEELQQ | 63 |
| P5A variant | QQLDQLLLMFIMMMLQQ | 64 |
| P5A variant M to A | QQLDQLLLAFIAAALQQ | 65 |
| P5A variant M to E | QQLDQLLLEFIEEELQQ | 66 |
| P5A variant | LDQLLLMFIMMML | 67 |
| P5A variant M to A | LDQLLLAFIAAAL | 68 |
| P5A variant M to E | LDQLLLEFIEEEL | 69 |
| P5A variant Q to E | SAGSEEELDQLLLMFIMMMLEE | 70 |
| P5 variant Q to E | SAGSEEELDLLLMFIMMMLEE | 41 |

TABLE 1-continued

Peptide Variants of Peptide P5/P5A
(SEQ ID NOS: 8 and 9)

| Peptide Name | Sequence | SEQ ID NO: |
| --- | --- | --- |
| P5 mut 8E P5-35 | SAGSEQQEDLLLMFIMMMLQQ | 71 |
| P5 mut 10E P5-36 | SAGSEQQLDELLMFIMMMLQQ | 72 |
| P5 mut 11E P5-37 | SAGSEQQLDLELMFIMMMLQQ | 73 |
| P5 mut 12E P5-38 | SAGSEQQLDLLEMFIMMMLQQ | 74 |
| P5 mut 13E P5-39 | SAGSEQQLDLLLEFIMMMLQQ | 75 |
| P5 mut 14E P5-40 | SAGSEQQLDLLLMEIMMMLQQ | 76 |
| P5 mut 15E P5-41 | SAGSEQQLDLLLMFEMMMLQQ | 77 |
| P5 mut 16E P5-42 | SAGSEQQLDLLLMFIEMMLQQ | 78 |
| P5 mut 17E P5-43 | SAGSEQQLDLLLMFIMEMLQQ | 79 |
| P5 mut 18E P5-44 | SAGSEQQLDLLLMFIMMELQQ | 80 |
| P5 mut 19E P5-45 | SAGSEQQLDLLLMFIMMMEQQ | 81 |
| P5 mut 9K | SAGSEQQLKLLLMFIMMMLQQ | 82 |
| P5 SS mut | SAGSESSLDLLLMFIMMMLQQ | 83 |
| P5 SS mut | SAGSEQQLDLLLMFIMMMLSS | 84 |
| P5 GG mut | SAGSEGGLDLLLMFIMMMLQQ | 85 |
| P5 GG mut | SAGSEQQLDLLLMFIMMMLGG | 86 |
| P5 single mut 8V | SAGSEQQVDLLLMFIMMMLQQ | 87 |
| P5 single mut 10V | SAGSEQQLDVLLMFIMMMLQQ | 88 |
| P5 single mut 11V | SAGSEQQLDLVLMFIMMMLQQ | 89 |
| P5 single mut 12V | SAGSEQQLDLLVMFIMMMLQQ | 90 |
| P5 single mut 13V | SAGSEQQLDLLLVFIMMMLQQ | 91 |
| P5 single mut 14V | SAGSEQQLDLLLMVIMMMLQQ | 92 |
| P5 single mut 15V | SAGSEQQLDLLLMFVMMMLQQ | 93 |
| P5 single mut 16V | SAGSEQQLDLLLMFIVMMLQQ | 94 |
| P5 single mut 17V | SAGSEQQLDLLLMFIMVMLQQ | 95 |
| P5 single mut 18V | SAGSEQQLDLLLMFIMMVLQQ | 96 |
| P5 single mut 19V | SAGSEQQLDLLLMFIMMMVQQ | 97 |
| P5A single mut 8E, P5-53 | SAGSEQQEDQLLLMFIMMMLQQ | 98 |
| P5A single mut 11E, P5-54 | SAGSEQQLDQELLMFIMMMLQQ | 99 |
| P5A single mut 12E | SAGSEQQLDQLELMFIMMMLQQ | 100 |
| P5A single mut 13E | SAGSEQQLDQLLEMFIMMMLQQ | 101 |
| P5A single mut 14E | SAGSEQQLDQLLLEFIMMMLQQ | 102 |
| P5A single mut 15E | SAGSEQQLDQLLLMEIMMMLQQ | 103 |
| P5A single mut 16E | SAGSEQQLDQLLLMFEMMMLQQ | 104 |
| P5A single mut 17E | SAGSEQQLDQLLLMFIEMMLQQ | 105 |
| P5A single mut 18E | SAGSEQQLDQLLLMFIMEMLQQ | 106 |
| P5A single mut 19E | SAGSEQQLDQLLLMFIMMELQQ | 107 |

TABLE 1-continued

Peptide Variants of Peptide P5/P5A
(SEQ ID NOS: 8 and 9)

| Peptide Name | Sequence | SEQ ID NO: |
| --- | --- | --- |
| P5A single mut 20E | SAGSEQQLDQLLLMFIMMMEQQ | 108 |
| P5A single mut 9K | SAGSEQQLKQLLLMFIMMMLQQ | 109 |
| P5A single mut 10E | SAGSEQQLDELLLMFIMMMLQQ | 110 |
| P5A single mut 10S | SAGSEQQLDSLLLMFIMMMLQQ | 111 |
| P5A single mut 10A | SAGSEQQLDALLLMFIMMMLQQ | 112 |
| P5A SS mut | SAGSESSLDQLLLMFIMMMLQQ | 113 |
| P5A SS mut | SAGSEQQLDQLLLMFIMMMLSS | 114 |
| P5A GG mut | SAGSEGGLDQLLLMFIMMMLQQ | 115 |
| P5A GG mut | SAGSEQQLDQLLLMFIMMMLGG | 116 |
| P5A single mut 8V | SAGSEQQVDQLLLMFIMMMLQQ | 117 |
| P5A single mut 11V | SAGSEQQLDQVLLMFIMMMLQQ | 118 |
| P5A single mut 12V | SAGSEQQLDQLVLMFIMMMLQQ | 119 |
| P5A single mut 13V | SAGSEQQLDQLLVMFIMMMLQQ | 120 |
| P5A single mut 14V | SAGSEQQLDQLLLVFIMMMLQQ | 121 |
| P5A single mut 15V | SAGSEQQLDQLLLMVIMMMLQQ | 122 |
| P5A single mut 16V | SAGSEQQLDQLLLMFVMMMLQQ | 123 |
| P5A single mut 17V | SAGSEQQLDQLLLMFIVMMLQQ | 124 |
| P5A single mut 18V | SAGSEQQLDQLLLMFIMVMLQQ | 125 |
| P5A single mut 19V | SAGSEQQLDQLLLMFIMMVLQQ | 126 |
| P5A single mut 20V | SAGSEQQLDQLLLMFIMMMVQQ | 127 |
| P5-1013 | SAGSEQQLDQLLLMFIMMML | 128 |
| P5-1014 | QQLDQLLLMFIMMML | 129 |
| P5-55 | SAGSEQQLDQLLLAFIAAALQQ | 130 |
| P5-1015 | SAGSEQQLDQLLLEFIEEELQQ | 131 |
| P5-1016 | QQLDLLLMFIMMMLQQ | 132 |
| P5-1017 | LDLLLMFIMMMLQQ | 133 |
| P5-1018 | SAGSEQQLDLLLMFIMMML | 134 |
| P5-1019 | QQLDLLLMFIIMMML | 135 |
| P5-1020 | LDLLLMFIMMML | 136 |
| P5-1021 | SAGSEQQLDLLLEFIEEELQQ | 137 |
| Cleavable tag seq | HHHHHHRQQLDLLLAFIAAALQQ | 138 |
| P5-5 | QLELLLAFIAAALQQ | 139 |
| P5-6 | SAGSEQQLDLLLAFIAAAL | 140 |
| P5-49 | SAGSEQQEDLLLAFIAAALQQ | 510 |
| P5-50 | SAGSEQQLDELLAFIAAALQQ | 511 |
| P5-51 | SAGSEQQEDELLAFIAAALQQ | 512 |
| P5-52 | SAGSEQQEDELLMFIMMMLQQ | 513 |

TABLE 1-continued

Peptide Variants of Peptide P5/P5A
(SEQ ID NOS: 8 and 9)

| Peptide Name | Sequence | SEQ ID NO: |
|---|---|---|
| P5-56 | *SEEQ*E*ELLLAFIAAALQQ*EE | 514 |
| P5-57 | *SEEQ*LE*ELLAFIAAALQQ*EE | 515 |
| P5-58 | *SEEQ*E*EELLAFIAAALQQ*EE | 516 |
| P5-59, P5-R | SAGSEQQLDLLLMFIMMMLQQR | 517 |
| P5-60, P5-21-R | SEEQLELLLAFIAAALQQEER | 518 |
| P5-61 | SAGSEQQEDLLLAFIALQQ | 519 |
| P5-62 | SAGSEQQLDELLAFIALQQ | 520 |
| P5-63 | SAGSEQQLDLLLEFIALQQ | 521 |
| P5-64 | SAGSEQQLDLLLAEIALQQ | 522 |
| P5-65 | SAGSEQQLDLLLAFIEALQQ | 523 |
| P5-66 | SAGSEQQLDLLLAFIAEALQQ | 524 |
| P5-67 | SAGSEQQLDLLLAFIEAALQQ | 525 |
| P5-68 | SAGSEQQLDLLLAFIAAELQQ | 526 |
| P5-69 | SAGSEQQLDLLLAEIAAALQQ | 527 |
| P5-70 | SAGSEQQLDLLLEFIAAALQQ | 528 |
| P5-71 | SAGSEQQEDLLLAFIAAALQQ | 529 |
| P5-72 | SAGSEQQLDELLAFIAAALQQ | 530 |
| P5-73 | SQAGSEQLDLLLMFIMMMLQQ | 531 |
| P5-74 | AEQGSSQLDLLLMFIMMMLQQ | 532 |
| P5-75 | NQGISEKQQLDLLLMFIMMMLQQ | 533 |
| P5-76 | NQGISEKQQLDLLLAFIAAALQQ | 534 |
| P5-77 | NFGTPDSTVQNPQDASKPNQLDLLLMFIMMMLQQ | 535 |
| P5-78 | NFGTPDSTVQNPQDASKPNQLDLLLAFIAAALQQ | 536 |
| P5-79 | ITPDGQGGGQIGDNPQLDLLLMFIMITMLQQ | 537 |
| P5-80 | ITPDGQGGGQIGDNPQLDLLLAFIAAALQQ | 538 |
| P5-87 | *SEE*QLDLLLAFIAAALQQ*EE* | 539 |
| P5-88 | *SEE*QLELLLAFIAAALQ*EE* | 540 |
| P5-89 | SAGSEEELDLLLMFIMMMLQQ | 541 |
| P5-90 | SAGSEQQLDLLLMFIMMMLEE | 542 |
| P5-91 | *SEE*QQLDLLLMFIMMMLQQ*EE* | 543 |
| P5-92 | *SEEEE*QLDQLLLAFIAAALQQR | 544 |
| P5-1022 | QLEQLLAFIAAALQQ | 545 |
| P5-1023 | QLDLLLAFIAAALQQ | 546 |

Select peptides in Table 1 include N- or C-terminal solubility tags, indicated by italic print, including SEEEEEEE, SEEEEEE, SEEEEE, SEEEE, SEEE, SEE, EE, EE, and EEE. Peptides comprising the sequences shown in Table 1 but lacking these specific solubility tags (or having a different solubility tag) are also contemplated herein.

TABLE 2

Peptide Variants of Peptide P5/P5A (SEQ ID NOS: 8 and 9)

| P5/P5A Core/Core Variants | SEQ ID NO: |
|---|---|
| LDLLLMFIMMML | 136 |
| LDQLLLMFIMMML | 67 |
| LDLLL(A/E)FIMMML | 141 |
| LDLLLMFI(A/E)MML | 142 |
| LDLLLMFIM(A/E)ML | 143 |
| LDLLLMFIMM(A/E)L | 144 |
| LDLLL(A/E)FI(A/E)MML | 145 |
| LDLLL(A/E)FIM(A/E)ML | 146 |
| LDLLL(A/E)FIMM(A/E)L | 147 |
| LDLLLMFI(A/E)(A/E)ML | 148 |
| LDLLLMFI(A/E)M(A/E)L | 149 |
| LDLLLMFIM(A/E)(A/E)L | 150 |
| LDLLLMFI(A/E)(A/E)(A/E)L | 151 |
| LDLLL(A/E)FIM(A/E)(A/E)L | 152 |
| LDLLL(A/E)FI(A/E)M(A/E)L | 153 |
| LDLLL(A/E)FI(A/E)(A/E)ML | 154 |
| LDLLL(A/E)FI(A/E)(A/E)(A/E)L | 155 |
| LDQLLL(A/E)FIMMML | 156 |
| LDQLLLMFI(A/E)MML | 157 |
| LDQLLLMFIM(A/E)ML | 158 |
| LDQLLLMFIMM(A/E)L | 159 |
| LDQLLL(A/E)FI(A/E)MML | 160 |
| LDQLLL(A/E)FIM(A/E)ML | 161 |
| LDQLLL(A/E)FIMM(A/E)L | 162 |
| LDQLLLMFI(A/E)(A/E)ML | 163 |
| LDQLLLMFI(A/E)M(A/E)L | 164 |
| LDQLLLMFIM(A/E)(A/E)L | 165 |
| LDQLLLMFI(A/E)(A/E)(A/E)L | 166 |
| LDQLLL(A/E)FIM(A/E)(A/E)L | 167 |
| LDQLLL(A/E)FI(A/E)M(A/E)L | 168 |
| LDQLLL(A/E)FI(A/E)(A/E)ML | 169 |
| LDQLLL(A/E)FI(A/E)(A/E)(A/E)L | 170 |
| (E/V)DLLLMFIMMML | 171 |
| (E/V)DLLL(A/E)FIMMML | 172 |
| (E/V)DLLLMFI(A/E)MML | 173 |
| (E/V)DLLLMFIM(A/E)ML | 174 |
| (E/V)DLLLMFIMM(A/E)L | 175 |
| (E/V)DLLL(A/E)FI(A/E)MML | 176 |
| (E/V)DLLL(A/E)FIM(A/E)ML | 177 |
| (E/V)DLLL(A/E)FIMM(A/E)L | 178 |
| (E/V)DLLLMFI(A/E)(A/E)ML | 179 |
| (E/V)DLLLMFI(A/E)M(A/E)L | 180 |
| (E/V)DLLLMFIM(A/E)(A/E)L | 181 |
| (E/V)DLLLMFI(A/E)(A/E)(A/E)L | 182 |
| (E/V)DLLL(A/E)FIM(A/E)(A/E)L | 183 |
| (E/V)DLLL(A/E)FI(A/E)M(A/E)L | 184 |
| (E/V)DLLL(A/E)FI(A/E)(A/E)ML | 185 |
| (E/V)DLLL(A/E)FI(A/E)(A/E)(A/E)L | 186 |
| (E/V)DQLLLMFIMMML | 187 |
| (E/V)DQLLL(A/E)FIMMML | 188 |
| (E/V)DQLLLMFI(A/E)MML | 189 |
| (E/V)DQLLLMFIM(A/E)ML | 190 |
| (E/V)DQLLLMFIMM(A/E)L | 191 |
| (E/V)DQLLL(A/E)FI(A/E)MML | 192 |
| (E/V)DQLLL(A/E)FIM(A/E)ML | 193 |
| (E/V)DQLLL(A/E)FIMM(A/E)L | 194 |
| (E/V)DQLLLMFI(A/E)(A/E)ML | 195 |
| (E/V)DQLLLMFI(A/E)M(A/E)L | 196 |
| (E/V)DQLLLMFIM(A/E)(A/E)L | 197 |
| (E/V)DQLLLMFI(A/E)(A/E)(A/E)L | 198 |
| (E/V)DQLLL(A/E)FIM(A/E)(A/E)L | 199 |
| (E/V)DQLLL(A/E)FI(A/E)M(A/E)L | 200 |
| (E/V)DQLLL(A/E)FI(A/E)(A/E)ML | 201 |
| (E/V)DQLLL(A/E)FI(A/E)(A/E)(A/E)L | 202 |
| LD(E/V)LLMFIMMML | 203 |
| LD(E/V)LL(A/E)FIMMML | 204 |
| LD(E/V)LLMFI(A/E)MML | 205 |
| LD(E/V)LLMFIM(A/E)ML | 206 |
| LD(E/V)LLMFIMM(A/E)L | 207 |
| LD(E/V)LL(A/E)FI(A/E)MML | 208 |

TABLE 2-continued

Peptide Variants of Peptide P5/P5A
(SEQ ID NOS: 8 and 9)

| P5/P5A Core/Core Variants | SEQ ID NO: |
|---|---|
| LD(E/V)LL(A/E)FIM(A/E)ML | 209 |
| LD(E/V)LL(A/E)FIMM(A/E)L | 210 |
| LD(E/V)LLMFI(A/E)(A/E)ML | 211 |
| LD(E/V)LLMFI(A/E)M(A/E)L | 212 |
| LD(E/V)LLMFIM(A/E)(A/E)L | 213 |
| LD(E/V)LLMFI(A/E)(A/E)(A/E)L | 214 |
| LD(E/V)LL(A/E)FIM(A/E)(A/E)L | 215 |
| LD(E/V)LL(A/E)FI(A/E)M(A/E)L | 216 |
| LD(E/V)LL(A/E)FI(A/E)(A/E)ML | 217 |
| LD(E/V)LL(A/E)FI(A/E)(A/E)(A/E)L | 218 |
| LDQ(E/V)LLMFIMMML | 219 |
| LDQ(E/V)LL(A/E)FIMMML | 220 |
| LDQ(E/V)LLMFI(A/E)MML | 221 |
| LDQ(E/V)LLMFIM(A/E)ML | 222 |
| LDQ(E/V)LLMFIMM(A/E)L | 223 |
| LDQ(E/V)LL(A/E)FI(A/E)MML | 224 |
| LDQ(E/V)LL(A/E)FIM(A/E)ML | 225 |
| LDQ(E/V)LL(A/E)FIMM(A/E)L | 226 |
| LDQ(E/V)LLMFI(A/E)(A/E)ML | 227 |
| LDQ(E/V)LLMFI(A/E)M(A/E)L | 228 |
| LDQ(E/V)LLMFIM(A/E)(A/E)L | 229 |
| LDQ(E/V)LLMFI(A/E)(A/E)(A/E)L | 230 |
| LDQ(E/V)LL(A/E)FIM(A/E)(A/E)L | 231 |
| LDQ(E/V)LL(A/E)FI(A/E)M(A/E)L | 232 |
| LDQ(E/V)LL(A/E)FI(A/E)(A/E)ML | 233 |
| LDQ(E/V)LL(A/E)FI(A/E)(A/E)(A/E)L | 234 |
| LDL(E/V)LMFIMMML | 235 |
| LDL(E/V)L(A/E)FIMMML | 236 |
| LDL(E/V)LMFI(A/E)MML | 237 |
| LDL(E/V)LMFIM(A/E)ML | 238 |
| LDL(E/V)LMFIMM(A/E)L | 239 |
| LDL(E/V)L(A/E)FI(A/E)MML | 240 |
| LDL(E/V)L(A/E)FIM(A/E)ML | 241 |
| LDL(E/V)L(A/E)FIMM(A/E)L | 242 |
| LDL(E/V)LMFI(A/E)(A/E)ML | 243 |
| LDL(E/V)LMFI(A/E)M(A/E)L | 244 |
| LDL(E/V)LMFIM(A/E)(A/E)L | 245 |
| LDL(E/V)LMFI(A/E)(A/E)(A/E)L | 246 |
| LDL(E/V)LL(A/E)FIM(A/E)(A/E)L | 247 |
| LDL(E/V)LL(A/E)FI(A/E)M(A/E)L | 248 |
| LDL(E/V)LL(A/E)FI(A/E)(A/E)ML | 249 |
| LDL(E/V)L(A/E)FI(A/E)(A/E)(A/E)L | 250 |
| LDQL(E/V)LMFIMMML | 251 |
| LDQL(E/V)L(A/E)FIMMML | 252 |
| LDQL(E/V)LMFI(A/E)MML | 253 |
| LDQL(E/V)LMFIM(A/E)ML | 254 |
| LDQL(E/V)LMFIMM(A/E)L | 255 |
| LDQL(E/V)L(A/E)FI(A/E)MML | 256 |
| LDQL(E/V)L(A/E)FIM(A/E)ML | 257 |
| LDQL(E/V)L(A/E)FIMM(A/E)L | 258 |
| LDQL(E/V)LMFI(A/E)(A/E)ML | 259 |
| LDQL(E/V)LMFI(A/E)M(A/E)L | 260 |
| LDQL(E/V)LMFIM(A/E)(A/E)L | 261 |
| LDQL(E/V)LMFI(A/E)(A/E)(A/E)L | 262 |
| LDQL(E/V)LL(A/E)FIM(A/E)(A/E)L | 263 |
| LDQL(E/V)LL(A/E)FI(A/E)M(A/E)L | 264 |
| LDQL(E/V)LL(A/E)FI(A/E)(A/E)ML | 265 |
| LDQL(E/V)L(A/E)FI(A/E)(A/E)(A/E)L | 266 |
| LDLL(E/V)MFIMMML | 267 |
| LDLL(E/V)(A/E)FIMMML | 268 |
| LDLL(E/V)MFI(A/E)MML | 269 |
| LDLL(E/V)MFIM(A/E)ML | 270 |
| LDLL(E/V)MFIMM(A/E)L | 271 |
| LDLL(E/V)(A/E)FI(A/E)MML | 272 |
| LDLL(E/V)(A/E)FIM(A/E)ML | 273 |
| LDLL(E/V)(A/E)FIMM(A/E)L | 274 |
| LDLL(E/V)MFI(A/E)(A/E)ML | 275 |
| LDLL(E/V)MFI(A/E)M(A/E)L | 276 |
| LDLL(E/V)MFIM(A/E)(A/E)L | 277 |
| LDLL(E/V)MFI(A/E)(A/E)(A/E)L | 278 |
| LDLL(E/V)LL(A/E)FIM(A/E)L | 279 |
| LDLL(E/V)LL(A/E)FI(A/E)M(A/E)L | 280 |
| LDLL(E/V)LL(A/E)FI(A/E)(A/E)ML | 281 |
| LDLL(E/V)(A/E)FI(A/E)(A/E)(A/E)L | 282 |

TABLE 2-continued

Peptide Variants of Peptide P5/P5A
(SEQ ID NOS: 8 and 9)

| P5/P5A Core/Core Variants | SEQ ID NO: |
|---|---|
| LDQLL(E/V)MFIMMML | 283 |
| LDQLL(E/V)(A/E)FIMMML | 284 |
| LDQLL(E/V)MFI(A/E)MML | 285 |
| LDQLL(E/V)MFIM(A/E)ML | 286 |
| LDQLL(E/V)MFIMM(A/E)L | 287 |
| LDQLL(E/V)(A/E)FI(A/E)MML | 288 |
| LDQLL(E/V)(A/E)FIM(A/E)ML | 289 |
| LDQLL(E/V)(A/E)FIMM(A/E)L | 290 |
| LDQLL(E/V)MFI(A/E)(A/E)ML | 291 |
| LDQLL(E/V)MFI(A/E)M(A/E)L | 292 |
| LDQLL(E/V)MFIM(A/E)(A/E)L | 293 |
| LDQLL(E/V)MFI(A/E)(A/E)(A/E)L | 294 |
| LDQLL(E/V)LL(A/E)FIM(A/E)(A/E)L | 295 |
| LDQLL(E/V)LL(A/E)FI(A/E)M(A/E)L | 296 |
| LDQLL(E/V)LL(A/E)FI(A/E)(A/E)ML | 297 |
| LDQLL(E/V)(A/E)FI(A/E)(A/E)(A/E)L | 298 |
| LDLLL(E/V)FIMMML | 299 |
| LDLLL(E/V)FI(A/E)MML | 300 |
| LDLLL(E/V)FIM(A/E)ML | 301 |
| LDLLL(E/V)FIMM(A/E)L | 302 |
| LDLLL(E/V)FI(A/E)(A/E)ML | 303 |
| LDLLL(E/V)FI(A/E)M(A/E)L | 304 |
| LDLLL(E/V)FIM(A/E)(A/E)L | 305 |
| LDLLL(E/V)FI(A/E)(A/E)(A/E)L | 306 |
| LDQLLL(E/V)FIMMML | 307 |
| LDQLLL(E/V)FI(A/E)MML | 308 |
| LDQLLL(E/V)FIM(A/E)ML | 309 |
| LDQLLL(E/V)FIMM(A/E)L | 310 |
| LDQLLL(E/V)FI(A/E)(A/E)ML | 311 |
| LDQLLL(E/V)FI(A/E)M(A/E)L | 312 |
| LDQLLL(E/V)FIM(A/E)(A/E)L | 313 |
| LDQLLL(E/V)FI(A/E)(A/E)(A/E)L | 314 |
| LDLLLM(E/V)IMMML | 315 |
| LDLLL(A/E)(E/V)IMMML | 316 |
| LDLLLM(E/V)I(A/E)MML | 317 |
| LDLLLM(E/V)IM(A/E)ML | 318 |
| LDLLLM(E/V)IMM(A/E)L | 319 |
| LDLLL(A/E)(E/V)I(A/E)MML | 320 |
| LDLLL(A/E)(E/V)IM(A/E)ML | 321 |
| LDLLL(A/E)(E/V)IMM(A/E)L | 322 |
| LDLLLM(E/V)I(A/E)(A/E)ML | 323 |
| LDLLLM(E/V)I(A/E)M(A/E)L | 324 |
| LDLLLM(E/V)IM(A/E)(A/E)L | 325 |
| LDLLL(A/E)(E/V)IM(A/E)(A/E)L | 326 |
| LDLLL(A/E)(E/V)I(A/E)M(A/E)L | 327 |
| LDLLL(A/E)(E/V)I(A/E)(A/E)ML | 328 |
| LDLLLM(E/V)I(A/E)(A/E)(A/E)L | 329 |
| LDQLLLM(E/V)IMMML | 330 |
| LDQLLL(A/E)(E/V)IMMML | 331 |
| LDQLLLM(E/V)I(A/E)MML | 332 |
| LDQLLLM(E/V)IM(A/E)ML | 333 |
| LDQLLLM(E/V)IMM(A/E)L | 334 |
| LDQLLL(A/E)(E/V)I(A/E)MML | 335 |
| LDQLLL(A/E)(E/V)IM(A/E)ML | 336 |
| LDQLLL(A/E)(E/V)IMM(A/E)L | 337 |
| LDQLLLM(E/V)I(A/E)(A/E)ML | 338 |
| LDQLLLM(E/V)I(A/E)M(A/E)L | 339 |
| LDQLLLM(E/V)IM(A/E)(A/E)L | 340 |
| LDQLLL(A/E)(E/V)IM(A/E)(A/E)L | 341 |
| LDQLLL(A/E)(E/V)I(A/E)M(A/E)L | 342 |
| LDQLLL(A/E)(E/V)I(A/E)(A/E)ML | 343 |
| LDQLLLM(E/V)I(A/E)(A/E)(A/E)L | 344 |
| LDLLLMF(E/V)MMML | 345 |
| LDLLL(A/E)F(E/V)MMML | 346 |
| LDLLLMF(E/V)(A/E)MML | 347 |
| LDLLLMF(E/V)M(A/E)ML | 348 |
| LDLLLMF(E/V)MM(A/E)L | 349 |
| LDLLL(A/E)F(E/V)(A/E)MML | 350 |
| LDLLL(A/E)F(E/V)M(A/E)ML | 351 |
| LDLLL(A/E)F(E/V)MM(A/E)L | 352 |
| LDLLLMF(E/V)(A/E)(A/E)ML | 353 |
| LDLLLMF(E/V)(A/E)M(A/E)L | 354 |
| LDLLLMF(E/V)M(A/E)(A/E)L | 355 |
| LDLLLMF(E/V)(A/E)(A/E)(A/E)L | 356 |

TABLE 2-continued

Peptide Variants of Peptide P5/P5A
(SEQ ID NOS: 8 and 9)

| P5/P5A Core/Core Variants | SEQ ID NO: |
|---|---|
| LDLLL(A/E)F(E/V)M(A/E)(A/E)L | 357 |
| LDLLL(A/E)F(E/V)(A/E)M(A/E)L | 358 |
| LDLLL(A/E)F(E/V)(A/E)(A/E)ML | 359 |
| LDLLL(A/E)F(E/V)(A/E)(A/E)(A/E)L | 360 |
| LDQLLLMF(E/V)MMML | 361 |
| LDQLLL(A/E)F(E/V)MMML | 362 |
| LDQLLLMF(E/V)(A/E)MML | 363 |
| LDQLLLMF(E/V)M(A/E)ML | 364 |
| LDQLLLMF(E/V)MM(A/E)L | 365 |
| LDQLLL(A/E)F(E/V)(A/E)MML | 366 |
| LDQLLL(A/E)F(E/V)M(A/E)ML | 367 |
| LDQLLL(A/E)F(E/V)MM(A/E)L | 368 |
| LDQLLLMF(E/V)(A/E)(A/E)ML | 369 |
| LDQLLLMF(E/V)(A/E)M(A/E)L | 370 |
| LDQLLLMF(E/V)M(A/E)(A/E)L | 371 |
| LDQLLLMF(E/V)(A/E)(A/E)(A/E)L | 372 |
| LDQLLL(A/E)F(E/V)M(A/E)(A/E)L | 373 |
| LDQLLL(A/E)F(E/V)(A/E)M(A/E)L | 374 |
| LDQLLL(A/E)F(E/V)(A/E)(A/E)ML | 375 |
| LDQLLL(A/E)F(E/V)(A/E)(A/E)(A/E)L | 376 |
| LDLLLMFI(E/V)MML | 377 |
| LDLLL(A/E)FI(E/V)MML | 378 |
| LDLLLMFI(E/V)(A/E)ML | 379 |
| LDLLLMFI(E/V)M(A/E)L | 380 |
| LDLLL(A/E)FI(E/V)(A/E)ML | 381 |
| LDLLL(A/E)FI(E/V)(A/E)ML | 382 |
| LDLLL(A/E)FI(E/V)M(A/E)L | 383 |
| LDLLLMFI(E/V)(A/E)(A/E)L | 384 |
| LDLLL(A/E)FI(E/V)(A/E)(A/E)L | 385 |
| LDQLLLMFI(E/V)MML | 386 |
| LDQLLL(A/E)FI(E/V)MML | 387 |
| LDQLLLMFI(E/V)(A/E)ML | 388 |
| LDQLLLMFI(E/V)M(A/E)L | 389 |
| LDQLLL(A/E)FI(E/V)(A/E)ML | 390 |
| LDQLLL(A/E)FI(E/V)M(A/E)L | 391 |
| LDQLLLMFI(E/V)(A/E)(A/E)L | 392 |
| LDQLLL(A/E)FI(E/V)(A/E)(A/E)L | 393 |
| LDLLLMFIM(E/V)ML | 394 |
| LDLLL(A/E)FIM(E/V)ML | 395 |
| LDLLLMFIM(E/V)(A/E)L | 396 |
| LDLLLMFI(A/E)(E/V)ML | 397 |
| LDLLL(A/E)FIM(E/V)(A/E)L | 398 |
| LDLLL(A/E)FI(A/E)(E/V)ML | 399 |
| LDLLLMFI(A/E)(E/V)(A/E)L | 400 |
| LDLLL(A/E)FI(A/E)(E/V)(A/E)L | 401 |
| LDQLLLMFIM(E/V)ML | 402 |
| LDQLLL(A/E)FIM(E/V)ML | 403 |
| LDQLLLMFIM(E/V)(A/E)L | 404 |
| LDQLLLMFI(A/E)(E/V)ML | 405 |
| LDQLLL(A/E)FIM(E/V)(A/E)L | 406 |
| LDQLLL(A/E)FI(A/E)(E/V)ML | 407 |
| LDQLLLMFI(A/E)(E/V)(A/E)L | 408 |
| LDQLLL(A/E)FI(A/E)(E/V)(A/E)L | 409 |
| LDLLLMFIMM(E/V)L | 410 |
| LDLLL(A/E)FIMM(E/V)L | 411 |
| LDLLLMFI(A/E)M(E/V)L | 412 |
| LDLLLMFIM(A/E)(E/V)L | 413 |
| LDLLL(A/E)FI(A/E)M(E/V)L | 414 |
| LDLLL(A/E)FIM(A/E)(E/V)L | 415 |
| LDLLLMFI(A/E)(A/E)(E/V)L | 416 |
| LDLLL(A/E)FI(A/E)(A/E)(E/V)L | 417 |
| LDQLLLMFIMM(E/V)L | 418 |
| LDQLLL(A/E)FIMM(E/V)L | 419 |
| LDQLLLMFI(A/E)M(E/V)L | 420 |
| LDQLLLMFIM(A/E)(E/V)L | 421 |
| LDQLLL(A/E)FI(A/E)M(E/V)L | 422 |
| LDQLLL(A/E)FIM(A/E)(E/V)L | 423 |
| LDQLLLMFI(A/E)(A/E)(E/V)L | 424 |
| LDQLLL(A/E)FI(A/E)(A/E)(E/V)L | 425 |
| LDLLLMFIMKM(E/V) | 426 |
| LDLLL(A/E)FIMKM(E/V) | 427 |
| LDLLLMFI(A/E)MM(E/V) | 428 |
| LDLLLMFIM(A/E)M(E/V) | 429 |
| LDLLLMFIMM(A/E)(E/V) | 430 |

TABLE 2-continued

Peptide Variants of Peptide P5/P5A (SEQ ID NOS: 8 and 9)

| P5/P5A Core/Core Variants | SEQ ID NO: |
|---|---|
| LDLLL(A/E)FI(A/E)MM(E/V) | 431 |
| LDLLL(A/E)FIM(A/E)M(E/V) | 432 |
| LDLLL(A/E)FIMM(A/E)(E/V) | 433 |
| LDLLLMFI(A/E)(A/E)M(E/V) | 434 |
| LDLLLMFI(A/E)M(A/E)(E/V) | 435 |
| LDLLLMFIM(A/E)(A/E)(E/V) | 436 |
| LDLLLMFI(A/E)(A/E)(A/E)(E/V) | 437 |
| LDLLL(A/E)FIM(A/E)(A/E)(E/V) | 438 |
| LDLLL(A/E)FI(A/E)M(A/E)(E/V) | 439 |
| LDLLL(A/E)FI(A/E)(A/E)M(E/V) | 440 |
| LDLLL(A/E)FI(A/E)(A/E)(A/E)(E/V) | 441 |
| LDQLLLMFIMMM(E/V) | 442 |
| LDQLLL(A/E)FIMMM(E/V) | 443 |
| LDQLLLMFI(A/E)MM(E/V) | 444 |
| LDQLLLMFIM(A/E)M(E/V) | 445 |
| LDQLLLMFIMM(A/E)(E/V) | 446 |
| LDQLLL(A/E)FI(A/E)MM(E/V) | 447 |
| LDQLLL(A/E)FIM(A/E)M(E/V) | 448 |
| LDQLLL(A/E)FIMM(A/E)(E/V) | 449 |
| LDQLLLMFI(A/E)(A/E)M(E/V) | 450 |
| LDQLLLMFI(A/E)M(A/E)(E/V) | 451 |
| LDQLLLMFIM(A/E)(A/E)(E/V) | 452 |
| LDQLLLMFI(A/E)(A/E)(A/E)(E/V) | 453 |
| LDQLLL(A/E)FIM(A/E)(A/E)(E/V) | 454 |
| LDQLLL(A/E)FI(A/E)M(A/E)(E/V) | 455 |
| LDQLLL(A/E)FI(A/E)(A/E)M(E/V) | 456 |
| LDQLLL(A/E)FI(A/E)(A/E)(A/E)(E/V) | 457 |
| LKLLLMFIMMML | 458 |
| LKLLL(A/E)FIMMML | 459 |
| LKLLLMFI(A/E)MML | 460 |
| LKLLLMFIM(A/E)ML | 461 |
| LKLLLMFIMM(A/E)L | 462 |
| LKLLL(A/E)FI(A/E)MML | 463 |
| LKLLL(A/E)FIM(A/E)ML | 464 |
| LKLLL(A/E)FIMM(A/E)L | 465 |
| LKLLLMFI(A/E)(A/E)ML | 466 |
| LKLLLMFI(A/E)M(A/E)L | 467 |
| LKLLLMFIM(A/E)(A/E)L | 468 |
| LKLLLMFI(A/E)(A/E)(A/E)L | 469 |
| LKLLL(A/E)FIM(A/E)(A/E)(E/V) | 470 |
| LKLLL(A/E)FI(A/E)M(A/E)(E/V) | 471 |
| LKLLL(A/E)FI(A/E)(A/E)M(E/V) | 472 |
| LKLLL(A/E)FI(A/E)(A/E)(A/E)L | 473 |
| LKQLLLMFIMMML | 474 |
| LKQLLL(A/E)FIMMML | 475 |
| LKQLLLMFI(A/E)MML | 476 |
| LKQLLLMFIM(A/E)ML | 477 |
| LKQLLLMFIMM(A/E)L | 478 |
| LKQLLL(A/E)FI(A/E)MML | 479 |
| LKQLLL(A/E)FIM(A/E)ML | 480 |
| LKQLLL(A/E)FIMM(A/E)L | 481 |
| LKQLLLMFI(A/E)(A/E)ML | 482 |
| LKQLLLMFI(A/E)M(A/E)L | 483 |
| LKQLLLMFIM(A/E)(A/E)L | 484 |
| LKQLLLMFI(A/E)(A/E)(A/E)L | 485 |
| LKQLLL(A/E)FIM(A/E)(A/E)(E/V) | 486 |
| LKQLLL(A/E)FI(A/E)M(A/E)(E/V) | 487 |
| LKQLLL(A/E)FI(A/E)(A/E)M(E/V) | 488 |
| LKQLLL(A/E)FI(A/E)(A/E)(A/E)L | 489 |
| LD(E/S/A)LLLMFIMMML | 490 |
| LD(E/S/A)LLL(A/E)FIMMML | 491 |
| LD(E/S/A)LLLMFI(A/E)MML | 492 |
| LD(E/S/A)LLLMFIM(A/E)ML | 493 |
| LD(E/S/A)LLLMFIMM(A/E)L | 494 |
| LD(E/S/A)LLL(A/E)FI(A/E)MML | 495 |
| LD(E/S/A)LLL(A/E)FIM(A/E)ML | 496 |
| LD(E/S/A)LLL(A/E)FIMM(A/E)L | 497 |
| LD(E/S/A)LLLMFI(A/E)(A/E)ML | 498 |
| LD(E/S/A)LLLMFI(A/E)M(A/E)L | 499 |
| LD(E/S/A)LLLMFIM(A/E)(A/E)L | 500 |
| LD(E/S/A)LLLMFI(A/E)(A/E)(A/E)L | 501 |
| LD(E/S/A)LLL(A/E)FIM(A/E)(A/E)L | 502 |
| LD(E/S/A)LLL(A/E)FI(A/E)M(A/E)L | 503 |

TABLE 2-continued

Peptide Variants of Peptide P5/P5A
(SEQ ID NOS: 8 and 9)

| P5/P5A Core/Core Variants | SEQ ID NO: |
|---|---|
| LD(E/S/A)LLL(A/E)FI(A/E)(A/E)ML | 504 |
| LD(E/S/A)LLL(A/E)FI(A/E)(A/E)(A/E)L | 505 |

In certain embodiments, the peptide includes one or more mutations relative to the corresponding wildtype amino acid sequence of SAGSEQQLDQLLAMFIMMMLQQ (SEQ ID NO: 7), which corresponds to amino acid residues 33-54 of the HreX protein of *Xanthomonas campestris* pv. *pelargonii* (see U.S. Pat. No. 6,960,705

TABLE 3-continued

| Peptide & Optimized Host | Nucleotide Sequence | SEQ ID NO: |
|---|---|---|
| P5-21 in E. coli | AGCGAAGAACAGCTGGAACTGCTGCTGGCATT TATTGCAGCAGCACTGCAGCAGGAAGAA | 507 |
| P5 in Zea mays | TCCGCCGGCTCCGAGCAGCAGCTGGACCTGCT GCTGATGTTCATCATGATGATGCTGCAGCAG | 508 |
| P5-21 in Zea mays | TCCGAGGAGCAGCTGGAGCTGCTGCTGGCCTT CATCGCCGCCGCCCTGCAGCAGGAGGAG | 509 |

With knowledge of the encoded amino acid sequence listed herein and the desired transgenic organism, additional codon-optimized DNA sequences and RNA sequences can be generated with nothing more than routine skill.

Expression (including transcription and translation) of a peptide or fusion polypeptide of the invention by the DNA construct may be regulated with respect to the level of expression, the tissue type(s) where expression takes place and/or developmental stage of expression. A number of heterologous regulatory sequences (e.g., promoters and enhancers) are available for controlling the expression of the DNA construct in plants. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394, each of which is hereby incorporated by reference in its entirety), the nopaline synthase (NOS) promoter (Ebert et al., *Proc. Natl. Acad. Sci. (U.S.A.)* 84:5745-5749 (1987), which is hereby incorporated by reference in its entirety), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), which is hereby incorporated by reference in its entirety) and the CaMV 35S promoter (Odell et al., *Nature* 313:810-812 (1985), which is hereby incorporated by reference in its entirety), the figwort mosaic virus 35S-promoter (U.S. Pat. No. 5,378,619, which is hereby incorporated by reference in its entirety), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628 (1987), which is hereby incorporated by reference in its entirety), the sucrose synthase promoter (Yang et al., *Proc. Natl. Acad. Sci. (U.S.A.)* 87:4144-4148 (1990), which is hereby incorporated by reference in its entirety), the R gene complex promoter (Chandler et al., *Plant Cell* 1:1175-1183 (1989), which is hereby incorporated by reference in its entirety), the chlorophyll a/b binding protein gene promoter, the CsVMV promoter (Verdaguer et al., *Plant Mol Biol.,* 37:1055-1067 (1998), which is hereby incorporated by reference in its entirety), and the melon actin promoter (PCT Publ. No. WO00/56863, which is hereby incorporated by reference in its entirety). Exemplary tissue-specific promoters include the tomato E4 and E8 promoters (U.S. Pat. No. 5,859,330, which is hereby incorporated by reference in its entirety) and the tomato 2AII gene promoter (Van Haaren et al., *Plant Mol Bio.,* 21:625-640 (1993), which is hereby incorporated by reference in its entirety).

In one preferred embodiment, expression of the DNA construct is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219 (1991), which is hereby incorporated by reference in its entirety), globulin (Belanger and Kriz, *Genet.* 129: 863-872 (1991), GenBank Accession No. L22295, each of which is hereby incorporated by reference in its entirety), gamma zein Z 27 (Lopes et al., *Mol Gen Genet.* 247:603-613 (1995), which is hereby incorporated by reference in its entirety), L3 oleosin promoter (U.S. Pat. No. 6,433,252, which is hereby incorporated by reference in its entirety), phaseolin (Bustos et al., *Plant Cell* 1(9):839-853 (1989), which is hereby incorporated by reference in its entirety), arcelin5 (U.S. Application Publ. No. 2003/0046727, which is hereby incorporated by reference in its entirety), a soybean 7S promoter, a 7Sα promoter (U.S. Application Publ. No. 2003/0093828, which is hereby incorporated by reference in its entirety), the soybean 754 conglycinin promoter, a 75α promoter (Beachy et al., *EMBO J.* 4:3047 (1985); Schuler et al., *Nucleic Acid Res.* 10(24):8225-8244 (1982), each of which is hereby incorporated by reference in its entirety), soybean trypsin inhibitor (Riggs et al., *Plant Cell* 1(6):609-621 (1989), which is hereby incorporated by reference in its entirety), ACP (Baerson et al., *Plant Mol. Biol.,* 22(2):255-267 (1993), which is hereby incorporated by reference in its entirety), stearoyl-ACP desaturase (Slocombe et al., *Plant Physiol.* 104(4):167-176 (1994), which is hereby incorporated by reference in its entirety), soybean a' subunit of β-conglycinin (Chen et al., *Proc. Natl. Acad. Sci.* 83:8560-8564 (1986), which is hereby incorporated by reference in its entirety), Vicia faba USP (U.S. Application Publ. No. 2003/229918, which is hereby incorporated by reference in its entirety) and *Zea mays* L3 oleosin promoter (Hong et al., *Plant Mol. Biol.,* 34(3):549-555 (1997), which is hereby incorporated by reference in its entirety).

Nucleic acid molecules encoding the peptides of the present invention can be prepared via solid-phase synthesis using, e.g., the phosphoramidite method and phosphoramidite building blocks derived from protected 2'-deoxynucleosides. To obtain the desired oligonucleotide, the building blocks are sequentially coupled to the growing oligonucleotide chain in the order required by the sequence of the product. Upon the completion of the chain assembly, the product is released from the solid phase to solution, deprotected, collected, and typically purified using HPLC. The limits of solid phase synthesis are suitable for preparing oligonucleotides up to about 200 nt in length, which encodes peptides on the order of about 65 amino acids or less. The ends of the synthetized oligonucleotide can be designed to include specific restriction enzyme cleavage site to facilitate ligation of the synthesized oligonucleotide into an expression vector.

For longer peptides, oligonucleotides can be prepared via solid phase synthesis and then the synthetic oligonucleotide sequences ligated together using various techniques. Recombinant techniques for the fabrication of whole synthetic genes are reviewed, for example, in Hughes et al., "Chapter Twelve—Gene Synthesis: Methods and Applications," *Methods in Enzymology* 498:277-309 (2011), which is hereby incorporated by reference in its entirety.

Synthetic oligonucleotides of the present invention include both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2' amino-, and 2'fluoro-amino-modified RNA Ligands or Human IFN-gamma that Inhibit Receptor Binding," *J. Immunol.* 159:259-267 (1997); Pagratis et al., "Potent 2'-amino, and 2'-fluoro-2'-deoxy-ribonucleotide RNA Inhibitors of Keratinocyte Growth Factor," *Nat. Biotechnol.* 15:68-73 (1997), each which is hereby incorporated by reference in its entirety) and the L-nucleic acids (sometimes termed Spiegelmers®), enantiomeric to natural D-nucleic acids (Klussmann et al., "Mirror-image RNA that Binds D-adenosine," *Nat. Biotechnol.* 14:1112-1115 (1996) and Williams et al., "Bioactive and nuclease-resistant L-DNA Ligand of Vasopressin," *Proc. Natl. Acad. Sci. USA* 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds. The use of locked nucleic acids (LNA) is also contemplated. These nucleic acid molecules can be used for multiple purposes, including application to plants or plants seeds as naked oligonucleotides or for in vitro translation of encoding oligonucleotides for production of the peptides of the present invention.

Once a suitable expression vector is selected, the desired nucleic acid sequences are cloned into the vector using standard cloning procedures in the art, as described by Sambrook et al., Molecular Cloning: A Laboratory Manual, Cold Springs Laboratory, Cold Springs Harbor, N.Y. (1989), or U.S. Pat. No. 4,237,224 to Cohen and Boyer, which are hereby incorporated by reference in their entirety. The vector is then introduced to a suitable host.

A variety of host-vector systems may be utilized to recombinantly express the peptides of the present invention. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by *Agrobacterium*. The expression elements of these vectors vary in their strength and specificities. Depending upon the host-vector system utilized, any one of a number of suitable transcription and translation elements can be used to carry out this and other aspects of the present invention.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Alternatively, if the peptide of interest of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above. The use of purification tags, described above, can simplify this process.

In certain embodiments, purification is not required. Where purification is not performed, cell-free lysates can be recovered following centrifugation for removal of cellular debris. The resulting cell-free lysate can be treated with heat for a sufficient amount of time to deactivate any native proteases in the recovered fraction, e.g., 10 min at 100° C. If desired, one or more of biocidal agents, protease inhibitors, and non-ionic surfactants can be introduced to such a cell-free preparation (see U.S. Application Publ. No. 20100043095 to Wei, which is hereby incorporated by reference in its entirety).

Once the peptides of the present invention are recovered, they can be used to prepare a composition that includes a carrier, and one or more additives selected from the group consisting of a bacteriocidal or biocidal agent, a protease inhibitor, a non-ionic surfactant, a fertilizer, an herbicide, an insecticide, a fungicide, a nematicide, biological inoculants, plant regulators, and mixtures thereof.

In certain embodiments, the compositions include greater than about 1 nM of the peptide, greater than about 10 nM of the peptide, greater than about 20 nM of the peptide, greater than about 30 nM of the peptide, greater than about 40 nM of the peptide, greater than about 50 nM of the peptide, greater than about 60 nM of the peptide, greater than about 70 nM of the peptide, greater than 80 about nM of the peptide, greater than about 90 nM of the peptide, greater than about 100 nM of the peptide, greater than about 150 nM of the peptide, greater than about 200 nM of the peptide, or greater than about 250 nM of the peptide. In certain embodiments, the compositions include less than about 1 nM of the peptide. For example, certain peptides can be present at a concentration of less than about 2 ng/ml, less than about 1.75 ng/ml, less than about 1.5 ng/ml, less than about 1.25 ng/ml, less than about 1.0 ng/ml, less than about 0.75 ng/ml, less than about 0.5 ng/ml, less than about 0.25 ng/ml, or even less than about 0.1 ng/ml.

Suitable carriers include water, aqueous solutions optionally containing one or more co-solvents, slurries, and solid carrier particles. Exemplary solid carriers include mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, and products of vegetable origin, such as cereal meal, tree bark meal, wood meal and nutshell meal, cellulose powders, starches and starch derivatives, as well as other mono-, di-, and poly-saccharides.

Suitable fertilizers include, without limitation, ammonium sulfate, ammonium phosphate, ammonium nitrate, ureas, and combinations thereof.

Suitable insecticides include, without limitation, members of the neonicotinoid class such as imidicloprid, clothianidin, and thiamethoxam; members of the organophosphate class such as chlorpyrifos and malathion; members of the pyrethroid class such as permethrin; other natural insecticides such as nicotine, nornicotine, and pyrethrins; members of the carbamate class such as aldicarb, carbofuran, and carbaryl; members of the macrocyclic lactone class such as various abamectin, avermectin, and ivermectin products; members of the diamide class such as chlorantraniliprole, cyantraniliprole, and flubendiamide; chitin synthesis inhibitors, particularly those of the benzoylurea class such as lufenuron and diflubenzuron; and any combination thereof, including combinations of two or more, three or more, or four or more insecticides. Additional insecticides are listed in the Compendium of Pesticide Common Names, which is database operated by Alan Wood and available in electronic form at the alanwood.net internet site.

Suitable fungicides include, without limitation, members of the strobilurin class such as azoxystrobin, pyraclostrobin, trifloxystrobin, picoxystrobin, and fluoxastrobin; members of the triazole class such as ipconazole, metconazole, tebuconazole, triticonazole, tetraconazole, difenoconazole, flutriafol, propiconazole and prothioconazole; members of the succinate dehydrogenase class such as carboxin, fluxapyroxad, boscalid and sedaxane: members of the phenylamide class such as metalaxyl, mefenoxam, benalaxyl, and oxadiyxl; members of the phenylpyrrole class such as fludioxonil; members of the phthalimide class such as captan; members of the dithiocarbamate class such as mancozeb and thiram; members of the benzimidazole class such as thiabendazole; and any combination thereof, including combinations of two or more, three or more, or four or more fungicides. Additional fungicides are listed in the Compendium of Pesticide Common Names, which is a database operated by Alan Wood and available in electronic form at the alanwood.net internet site.

Suitable nematicides include, without limitation, chemicals of the carbamate class such as aldicarb, aldoxycarb, oxamyl, carbofuran, and cleothocarb; and chemicals of the organophosphate class such as thionazin, ethoprophos, fenamiphos, fensulfothion, terbufos, isazofos, and ebufos. Additional nematicides are listed in the Compendium of Pesticide Common Names, which is a database operated by Alan Wood and available in electronic form at the alanwood.net internet site.

Suitable bactericides include, without limitation, those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie; Proxel® GXL from ICI). Additional bactericides are listed in the Compendium of Pesticide Common Names, which is a database operated by Alan Wood and available in electronic form at the alanwood.net internet site.

Suitable inoculants include, without limitation, *Bradyrhizobium* spp., particularly *Bradyrhizobium japonicum* (BASF Vault® products), *Bacillus subtilis, Bacillus firmus, Bacillus pumilis, Streptomyces lydicus, Trichoderma* spp., *Pasteuria* spp., other cultures of rhizobial cells (BASF Nodulator® and Rhizo-Flo®), and any combination thereof, including combinations of two or more, three or more, or four or more inoculants. The inoculants can be recombinant in nature, as described hereinafter, to facilitate expression and optionally secretion of a polypeptide of the invention. Alternatively, these inoculants can be otherwise commercially available forms that are unable to express/secrete a polypeptide of the invention.

Plant regulators are chemical substances, whether natural or synthetic, that either stimulate or inhibit plant biochemical signaling. These are usually, but not exclusively, recognized by receptors on the surface of the cell, causing a cascade of reactions in the cell. Suitable plant regulators include, without limitation, ethephon; ethylene; salicylic acid; acetylsalicylic acid; jasmonic acid; methyl jasmonate; methyl dihydrojasmonate; chitin; chitosan; abscisic acid; any auxin compound or inhibitor, including but not limited to (4-chlorophenoxy)acetic acid, (2,4-dichlorophenoxy)acetic acid, and 2,3,5-triiodobenzoic acid; any cytokinin, including but not limited to kinetin and zeatin; gibberellins; brassinolide; and any combination thereof, including combinations of two or more, three or more, or four or more regulators.

Other suitable additives include buffering agents, wetting agents, coating agents, and abrading agents. These materials can be used to facilitate application of the compositions in accordance with the present invention. In addition, the compositions can be applied to plant seeds with other conventional seed formulation and treatment materials, including clays and polysaccharides.

Compositions or systems use for plant seed treatment include: one or more of the peptides of the present invention, preferably though not exclusively one of P5, P5-8, P5-21, P5-25, P5-27, P5-35, or P5-46 (SEQ ID NOS: 8, 14, 33, 52, 53, 71, and 58 respectively) in combination with one or more insecticides, nematicides, fungicides, other inoculants, or other plant regulators, including combinations of multiple insecticides, or multiple nematicides, multiple fungicides, multiple other inoculants, or multiple plant regulators. Suitable insecticides, nematicides, fungicides, inoculants, and plant regulators for these combination treatments include those identified above. These compositions are presented in the form of a single composition at the time of seed treatment. In contrast, a system used for seed treatment may involve multiple treatments, e.g., a composition containing the peptides is used in one treatment and a composition containing the one or more insecticides, nematicides, fungicides, plant regulators and/or bactericides, is used in a separate treatment. In the latter embodiment, both of these treatments are carried out at about the same time, i.e., before planting or at about the time of planting.

One such example includes one or more of peptides of the present invention, including (without limitation) one of P5, P5-8, P5-21, P5-25, P5-27, P5-35, or P5-46 (SEQ ID NOS: 8, 14, 33, 52, 53, 71, and 58 respectively), in combination with Poncho™ (clothianidin) available from Bayer Crop Science, Poncho™ VOTiVO (clothianidin and *Bacillus firmus* biological nematicide) available from Bayer Crop Science, and Gaucho™ (imidicloprid) available from Bayer Crop Science.

Another example includes one or more of peptides of the present invention, including (without limitation) one of P5, P5-8, P5-21, P5-25, P5-27, P5-35, or P5-46 (SEQ ID NOS: 8, 14, 33, 52, 53, 71, and 58 respectively), in combination with Cruiser™ (thiamethoxam) available from Syngenta, CruiserMaxx™ (thiamethoxam, mefenoxam, and fludioxynil) available from Syngenta, Cruiser Extreme™ (thiamethoxam, mefenoxam, fludioxynil, and azoxystrobin) available from Syngenta, Avicta™ (thiamethoxam and abamectin) available from Syngenta, and Avicta™ Complete (thiamethoxam, abamectin, and Clariva Complete™ which contains the *Pasteuria nishizawae*—Pn1 biological inoculant) available from Syngenta, and Avicta Complete™ Corn (thiamethoxam, mefenoxam, fludioxynil, azoxystrobin, thiabendazole and abamectin) available from Syngenta.

Another example includes one or more of peptides of the present invention, including (without limitation) one of P5, P5-8, P5-21, P5-25, P5-27, P5-35, or P5-46 (SEQ ID NOS: 8, 14, 33, 52, 53, 71, and 58 respectively), in combination with Vault Liquid plus Integral (*Bradyrhizobium* species and *Bacillus subtilis* strain MBI 600 inoculants) available from BASF, Vault NP (*Bradyrhizobium japonicum* inoculant) available from BASF, and Subtilex NG (*Bacillus subtilis* biological inoculant) available from BASF.

As an alternative to using peptides or compositions to apply the peptides of the present invention to plants, the use of beneficial microbes to deliver the peptide to the plant or plant seed, or the locus where the plant seed is planted in soil (and where the mature plant is grown), is also contemplated. Thus, a further aspect of the invention involves the engineering and application of beneficial microbes to produce peptides of the present invention. Beneficial microbes execute a number of useful activities, reviewed in Glick, "Plant Growth-Promoting Bacteria: Mechanisms and Applications," *Scientifica*, Article ID 963401 (2012), which is hereby incorporated by reference in its entirety. Beneficial microbes can provide nutrition to a plant. This may come in the form of amino acids and other nitrogen-containing compounds through the process of nitrogen fixation. Beneficial microbes may also liberate phosphate from inaccessible mineral deposits in the soil and make these available. For example, bacteria can synthesize siderophores which bind and solubilize inaccessible iron deposits. These iron-siderophore complexes can be absorbed by plants. Microbes can produce analogs of plant signaling hormones which stimulate growth and reduce stress signaling. Finally, beneficial microbes can compete with pathogenic organisms by removing resources including iron as well as synthesis of antibiotic compounds. Beneficial microbes may exhibit other behaviors and are not limited to the behaviors listed above. Beneficial organisms are classified as epiphytic (living on or near the surface of plant tissues) or endophytic (living within plant tissues).

Suitable beneficial bacterium include, without limitation, *Pseudomonas* (e.g., *P. fluorescens, P. aureofaciens, P. chlororaphis, P. solanacearum,* and *P. syringae*), *Sphingomonas* (e.g., *S. phyllosphaerae, S. roseiflava, S. melonis, S. azotifigens,* and *S. mali*) (see also Innerebner et al., "Protection of *Arabidopsis thaliana* Against Leaf-Pathogenic *Pseudomonas syringae* by *Sphingomonas* Strains in a Controlled Model System," *Appl. Environ. Microbiol.* 77:3202-3210 (2011), which is hereby incorporated by reference in its entirety), *Bacillus* (*B. firmus, B. licheniformis, B. megaterium, B. mucilaginous, B. pumilus, B. subtilis,* and *B. subtilis* var. *amyloliquefaciens*), *Streptomyces* (e.g., *S. griseoviridis* and *S. lydicus*), *Rhizobium* (e.g., *R. meliloti, R. trifolii, R. leguminosarum, R. phaseolin, R. lupine,* and *R. japonicum*), *Frankia* (e.g., *F. alni*), and *Azospirillum* (e.g., *A. brasilense* and *A. lipoferum*).

Additional beneficial bacterium, include, without limitation, *Agrobacterium radiobacter, Azotobacter chroococcum, Burkholderia cepacia, Delftia acidovorans, Paenobacillus macerans, Pantoea agglomerans,* and *Serratia entomophilia.*

In certain embodiments, the beneficial microbe may be a filamentous fungal host cell. In some embodiments, the host cell may be a cell of a strain that has a history of use for production of proteins that has GRAS status, i.e., a Generally Recognized as Safe, by the FDA.

In some embodiments, beneficial fungal microbes may be of a strain of *Aspergillus niger* which include ATCC 22342, ATCC 44733, ATCC 14331, ATCC 11490, NRRL 3112, and strains derived therefrom. In some embodiments, beneficial fungal microbes may be strains of *Trichoderma* (e.g. *T. harzianum, T. viride, T. koningi, T. reesei* and *T. hamatum*) which include functional equivalents of RL-P37 (Sheir-Neiss et al. (1984) *Appl. Microbiol. Biotechnology* 20:46-53, which is hereby incorporated by reference in its entirety). Other useful beneficial fungal microbes include, without limitation, NRRL 15709, ATCC 13631, ATCC 26921 (QM 9414) ATCC 32098, ATCC 32086, and ATCC 56765 (RUT-30). In some embodiments, beneficial fungal microbes may be strains of non-filamentous fungal yeasts, including, without limitation, strains of *Rhodotorula* (e.g., *R. graminis* WP1 and *R. mucilaginosa*) (see U.S. Pat. No. 8,728,781 and Xin et al., "Characterization of Three Endophytic, Indole-3-Acetic Acid-Producing Yeasts Occurring in *Populus* Trees," *Mycol. Res.* 113:973-980 (2009), which are hereby incorporated by reference in their entirety).

Peptide expression systems can be created using existing plasmid systems by one skilled in the art. One notable guideline is that regulation of peptide expression should be well controlled. High peptide concentrations detected by the plant will likely trigger an intense immune response with widespread cell death characteristic of the hypersensitive response. In contrast, lower peptide expression levels should stimulate the immunity while minimizing cell death. This effect may be further balanced by careful choice of secretion sequences. Expression of peptides in *Pseudomonas fluorescens* may be accomplished using the expression strains and tools described by Retallack et al., "Reliable protein production in a *Pseudomonas fluorescens* expression system," *Protein Expression and Purification* 81:157-65 (2012), which is hereby incorporated by reference in its entirety. Expression of peptides in *Bacillus subtilis* can be accomplished through vectors utilizing a subtilisin (aprE) promoter system. This can optionally be augmented using signal peptides to direct secretion of the peptide outside of the microbe. These functions are implemented in the "*Bacillus Subtilis* Secretory Protein Expression System" manual available from Clontech. Expression of proteins in *Streptomyces* has been demonstrated using plasmids as described by Fernandez-Abalos et al., "Posttranslational processing of the xylanase Xys1L from *Streptomyces halstedii* JM8 is carried out by secreted serine proteases," Microbiology 149:1623-32 (2003), which is hereby incorporated by reference in its entirety. Additional peptide expression systems can be produced by one skilled in the art.

Once engineered microbes are raised, e.g., in a fermentation apparatus, the engineered microbes can be recovered and then provided in either a dry composition or a liquid composition or suspension. For liquid compositions or suspensions, the microbes can be mixed in water, or a buffer solution, and applied as a spray treatment to the plants or the locus where plants are grown. Alternatively, the solution can be used as a seed treatment prior to planting the seeds. For dry compositions, the microbes can be dried with or without inert carrier particles, and the dry composition can be applied to seeds, the locus where seeds will be planted or plants are being grown, or directly to plants.

Colony forming units (c.f.u.) are used to quantify microbes. 1 c.f.u. of a microbe generates a single colony when spread onto a solid nutrient agar compatible with the organism and corresponds to one healthy, replication competent cell. In a dry powder formulation, the concentration of microbes can exceed $5\times10^{10}$ cfu/gram of material. Suitable concentrations for a dry formulation include $>10^{11}$, $>5\times10^{10}$, $>10^{10}$, $>10^9$, $>10^8$, $10^7$, or $>10^6$ cfu/gram. Likewise, microbes can be provided as a liquid suspension. Suitable concentrations for a liquid formulation include $>10^{10}$, $>10^9$, $>10^8$, $>10^7$, $>10^6$, $>10^5$ cfu/ml.

The present invention further relates to methods of imparting disease resistance to plants, enhancing plant growth, effecting pest control, imparting biotic or abiotic stress tolerance to plants, and/or modulating plant biochemical signaling. According to one embodiment, these methods involve applying an effective amount of an isolated peptide of the invention, or a composition of the invention to a plant or plant seed or the locus where the plant is growing or is expected to grow. As a consequence of such application, the peptide contacts cells of the plant or plant seed, and induces in the plant or a plant grown from the plant seed disease resistance, growth enhancement, tolerance to biotic stress, tolerance to abiotic stress, or altered biochemical signaling. According to an alternative embodiment, the peptide or composition of the invention can be applied to plants such that seeds recovered from such plants themselves are able to impart disease resistance in plants, to enhance plant growth, to affect insect control, to impart tolerance to biotic or abiotic stress, and/or to modulate biochemical signaling, to modulate maturation. According to yet another embodiment, these methods involve applying a recombinant inoculant to the plant seeds or plants, or the locus where the plant is growing or is expected to grow. As a consequence of such application, the recombinant inoculant expresses or secretes a peptide of the invention and the peptide contacts cells of the plant or plant seeds and induces in the plant or a plant grown from the plant seed disease resistance, growth enhancement, tolerance to biotic stress, tolerance to abiotic stress, or altered biochemical signaling.

In these embodiments, it is also possible to select plants or plant seeds or the locus to which the isolated peptide or composition of the invention is applied. For example, for fields known to contain a high nematode content, the plants or plant seeds to be grown in such fields, or the fields (locus), can be selectively treated by applying the isolated peptide or composition or recombinant inoculant of the invention as described herein; whereas no such treatment may be necessary for plants or plant seeds grown in fields containing low nematode content. Similarly, for fields having reduced irrigation, the plants or plant seeds to be grown in such fields, or the fields (locus), can be selectively treated by applying the isolated peptide or composition or recombinant inoculant of the invention as described herein; whereas no such treatment may be necessary for plants or plant seeds grown in fields having adequate irrigation. Likewise, for fields prone to flooding, the plants or plant seeds to be grown in such fields, or the fields (locus), can be selectively treated by applying the isolated peptide or composition or recombinant inoculant of the invention as described herein; whereas no such treatment may be necessary for plants or plant seeds grown in fields that are not prone to flooding. As yet another example of such selection, for fields prone to insect attack at certain times of the growing season, the plants or plant seeds to be grown in such fields, or the fields (locus), can be selectively treated by applying the isolated peptide or composition of the invention as described herein; whereas the same field may not be treated at ineffective times of the growing season or other fields that are not prone to such attack may go untreated. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

As an alternative to applying an isolated peptide or a composition containing the same to plants or plant seeds in order to impart disease resistance in plants, to effect plant growth, to control insects, to impart stress resistance and/or modulated biochemical signaling to the plants or plants grown from the seeds, transgenic plants or plant seeds can be utilized. When utilizing transgenic plants, this involves providing a transgenic plant transformed with a DNA molecule encoding a peptide of the invention and growing the plant under conditions effective to permit that DNA molecule to impart disease resistance to plants, to enhance plant growth, to control insects, to impart tolerance to biotic or abiotic stress, and/or to modulate biochemical signaling. Alternatively, a transgenic plant seed transformed with a DNA molecule encoding a peptide of the invention can be provided and planted in soil. A plant is then propagated from the planted seed under conditions effective to permit that DNA molecule to express the peptide and thereby impart disease resistance to the transgenic plant, to enhance plant growth, to control insects, to impart tolerance to biotic or abiotic stress, and/or to modulate biochemical signaling. This transgenic approach can be used in combination with the recombinant inoculant, or topical application of the isolated peptide or composition.

The present invention further relates to methods of improving desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These methods involve applying an effective amount of an isolated peptide of the present invention or a composition according to the present invention to a plant or the locus where the plant is growing. As a consequence of such application, the peptide contacts cells of the plant or plant seed, and induces desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Alternatively, an effective amount of an isolated peptide of the present invention or a composition according to the present invention can be applied to a harvested fruit or vegetable. As a consequence of such application, the peptide contacts cells of the harvested fruit or vegetable, and induces post-harvest disease resistance or desiccation resistance to the treated fruit or vegetables, and/or improved longevity of fruit or vegetable ripeness for the treated fruit or vegetables.

As an alternative to applying an isolated peptide or a composition containing the same to plants or plant seeds in order to induce desiccation resistance to cuttings removed from ornamental plants, post-harvest disease resistance or desiccation resistance to fruit or vegetables harvested from plants, and/or improved longevity of fruit or vegetable ripeness for fruit or vegetables harvested from plants, transgenic plants or plant seeds can be utilized. When utilizing transgenic plants, this involves providing a transgenic plant transformed with a DNA molecule encoding a peptide of the invention and growing the plant under conditions effective to permit that DNA molecule to induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants. Alternatively, a transgenic plant seed transformed with a DNA molecule encoding a peptide of the invention can be provided and planted in soil. A plant is then propagated from the planted seed under conditions effective to permit that DNA molecule to express the peptide and thereby induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants.

In these embodiments, it is also possible to select transgenic plants or plant seeds for carrying out the present invention. For example, for fields known to contain a high nematode content, the transgenic plants or plant seeds can be selectively grown in such fields; whereas non-transgenic plants or plant seeds can be grown in fields containing low nematode content. Similarly, for fields having reduced irrigation, the transgenic plants or plant seeds can be selectively grown in such fields; whereas non-transgenic plants or plant seeds can be grown in fields having adequate irrigation. Likewise, for fields prone to flooding, the transgenic plants or plant seeds can be grown in such fields; whereas non-transgenic plants or plant seeds can be grown in fields that are not prone to flooding. As yet another example of such selection, for fields prone to insect attack at certain times of the growing season, the transgenic plants or plant seeds can be selectively grown in such fields; whereas non-transgenic plants or plant seeds can be grown in fields that are not prone to such insect attack. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

The present invention further relates to methods of improving desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These methods involve applying an effective amount of an isolated peptide of the present invention or a composition according to the present invention to a plant or the locus where the plant is growing. As a consequence of such application, the peptide contacts cells of the plant or plant seed, and induces desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Alternatively, an effective amount of an isolated peptide of the present invention or a composition according to the present invention can be applied to a harvested fruit or vegetable. As a consequence of such application, the peptide contacts cells of the harvested fruit or vegetable, and induces post-harvest disease resistance or desiccation resistance to the treated fruit or vegetables, and/or improved longevity of fruit or vegetable ripeness for the treated fruit or vegetables.

In these embodiments, it is also possible to select plants, cuttings, fruits, vegetables, or the locus to which the isolated peptide or composition of the invention is applied. For example, for harvested cuttings or fruit or vegetables that are being shipped great distances or stored for long periods of time, then these can be selectively treated by applying the isolated peptide or composition of the invention as described herein; whereas harvested cuttings or fruit or vegetables that are being shipped locally and intended to be consumed without substantially periods of storage can be excluded from such treatment.

As an alternative to applying an isolated peptide or a composition containing the same to plants or plant seeds in order to induce desiccation resistance to cuttings removed from ornamental plants, post-harvest disease resistance or desiccation resistance to fruit or vegetables harvested from plants, and/or improved longevity of fruit or vegetable ripeness for fruit or vegetables harvested from plants, transgenic plants or plant seeds can be utilized. When utilizing transgenic plants, this involves providing a transgenic plant transformed with a DNA molecule encoding a peptide of the invention and growing the plant under conditions effective to permit that DNA molecule to induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants. Alternatively, a transgenic plant seed transformed with a DNA molecule encoding a peptide of the invention can be provided and planted in soil. A plant is then propagated from the planted seed under conditions effective to permit that DNA molecule to express the peptide and thereby induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants.

In these embodiments, it is also possible to select transgenic plants or plant seeds for carrying out the present invention. For example, transgenic plants or plant seeds can be selected for growing when it is known that harvested cuttings or fruit or vegetables are intended to be shipped great distances or stored for long periods of time post-harvest; whereas non-transgenic plants or plant seeds can be selected for growing when it is known that harvested cuttings or fruit or vegetables are intended to be shipped locally and/or consumed without substantially periods of storage.

Suitable plants include dicots and monocots, including agricultural, silvicultural, ornamental and horticultural plants, whether in a natural or genetically modified form. Exemplary plants include, without limitation, alfalfa, apple, apricot, asparagus, avocados, bananas, barley, beans, beech (*Fagus* spec.), begonia, birch, blackberry, blueberry, cabbage, camphor, canola, carrot, castor oil plant, cherry, cinnamon, citrus, cocoa bean, coffee, corn, cotton, cucumber, cucurbit, eucalyptus, fir, flax, fodder beet, fuchsia, garlic, geranium, grapes, ground nut, hemp, hop, juneberry, *juncea* (*Brassica juncea*), jute, lentil, lettuce, linseed, melon, mustard, nectarine, oak, oats, oil palm, oil-seed rape, olive, onion, paprika, pea, peach, pear, pelargonium, peppers, petunia, pine (*Pinus* spec.), plum, poplar (*Populus* spec.), pome fruit, potato, rape, raspberry, rice, rubber tree, rye, sorghum, soybean, spinach, spruce, squash, strawberry, sugar beet, sugar cane, sunflower, tea, teak, tobacco, tomato, triticale, turf, watermelon, wheat and willow (*Salix* spec.), *Arabidopsis thaliana*, Saintpaulia, poinsettia, chrysanthemum, carnation, and zinnia.

With respect to modified biochemical signaling, this includes both enhancement of certain plant biochemical pathways and diminishment of certain other plant biochemical pathways. Biochemical signaling pathways that can be altered in accordance with the present invention include gene expression and protein production, production of metabolites, and production of signaling molecules/secondary metabolites. Exemplary biochemical signaling pathways and their modifications include, without limitation, induction of nitric oxide production, peroxide production, and other secondary metabolites; agonist of the ethylene signaling pathway and induction of ethylene-responsive gene expression (see Dong et al., *Plant Phys.* 136:3628-3638 (2004); Li et al., *Planta* 239:831-46 (2014); Chang et al., *PLoS One* 10,e0125498 (2015), each of which is hereby incorporated by reference in its entirety); agonist of the salicylic acid signaling pathway and induction of salicylic acid-responsive gene expression (see Dong et al., *Plant J.* 20:207-215 (1999), which is hereby incorporated by reference in its entirety); agonist of the abscisic acid pathway and induction of abscisic acid-responsive gene expression (see Dong et al., *Planta* 221: 313-327 (2005), which is hereby incorporated by reference in its entirety); agonist of the gibberellin signaling pathway and induction of gibberellin-responsive gene expression (see Li et al., *Planta* 239:831-46 (2014), which is hereby incorporated by reference in its entirety); antagonist of jasmonic acid signaling and inhibiting expression of jasmonic acid-responsive genes (see Dong et al., *Plant Phys.* 136:3628-3638 (2004), which is hereby incorporated by reference in its entirety); inducing protease inhibitor expression (see Laluk and Mengiste, *Plant J.* 68:480-494 (2011); Xia et al., *Chin. Sci. Bull* 56: 2351-2358 (2011), each of which is hereby incorporated by reference in its entirety); inducing reactive oxygen species production in plant tissues; inducing immune-related and antimicrobial peptide production, such as, without limitation, peroxidase, superoxide dismutase, chitinase, and β-1,3-glucanase (Wang et al., *J. Agric. Food Chem.* 59:12527-12533 (2011), which is hereby incorporated by reference in its entirety); and inducing expansin gene expression and production (see Li et al., *Planta* 239:831-46 (2014), which is hereby incorporated by reference in its entirety).

With respect to disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: pathogenic *Pseudomonas* spp., pathogenic *Erwinia* spp., pathogenic *Xanthomonas* spp., and pathogenic *Ralstonia* spp. Plants can be made resistant, inter alia, to the following fungi by use of the method of the present invention: *Fusarium* spp. and *Phytophthora* spp.

With regard to the use of the peptides or compositions of the present invention to enhance plant growth, various forms of plant growth enhancement or promotion can be achieved. This can occur as early as when plant growth begins from seeds or later in the life of a plant. For example, plant growth according to the present invention encompasses greater yield, increased plant vigor, increased vigor of seedlings (i.e., post-germination), increased plant weight, increased biomass, increased number of flowers per plant, higher grain and/or fruit yield, increased quantity of seeds produced, increased percentage of seeds germinated, increased speed of germination, increased plant size, decreased plant height (for wheat), greater biomass, more and bigger fruit, earlier fruit coloration, earlier bud, fruit and plant maturation, more tillers or side shoots, larger leaves, delayed leaf senescence, increased shoot growth, increased root growth, altered root/shoot allocation, increased protein content, increased oil content, increased carbohydrate content, increased pigment content, increased chlorophyll content, increased total photosynthesis, increased photosynthesis efficiency, reduced respiration (lower $O_2$ usage), compensation for yield-reducing treatments, increased durability of stems (and resistance to stem lodging), increased durability of roots (and resistance to root lodging), better plant growth in low light conditions, and combinations thereof. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

With regard to the use of the peptides or compositions of the present invention to control pests (including but not limited to insects and nematodes, which are biotic stressors), such pest control encompasses preventing pests from contacting plants to which the peptide or composition of the invention has been applied, preventing direct damage to plants by feeding injury, causing pests to depart from such plants, killing pests proximate to such plants, interfering with insect larval feeding on such plants, preventing pests from colonizing host plants, preventing colonizing insects from releasing phytotoxins, interfering with egg deposition on host plants, etc. The present invention also prevents subsequent disease damage to plants resulting from pest infection.

The present invention is effective against a wide variety of insects (biotic stressors). European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide. The present invention is also effective against nematodes, another class of economically important biotic stressors. Soybean Cyst Nematode (*Heterodera glycines*) is a major pest of soybeans. Reniform Nematode (*Rotylenchulus reniformis*) is a major pest of cotton as can parasitize additional crop species, notably soy and corn. Additional nematode pests include the root knot nematodes of the genus *Meloidogyne* (particularly in cotton, wheat, and barley), cereal cyst nematodes of the genus *Heterodera* (particularly in soy, wheat, and barley), root lesion nematodes of the genus *Pratylenchus*, seed gall nematodes of the genus *Anguina* (particularly in wheat, barley, and rye), and stem nematodes of the genus *Ditylenchus*. Other biotic stressors include arachnids, weeds, and combinations thereof.

With regard to the use of the peptides or compositions of the present invention to impart abiotic stress resistance to plants, such abiotic stress encompasses any environmental factor having an adverse effect on plant physiology and development. Examples of such environmental stress include climate-related stress (e.g., drought, flood, frost, cold temperature, high temperature, excessive light, and insufficient light), air pollution stress (e.g., carbon dioxide, carbon monoxide, sulfur dioxide, $NO_R$, hydrocarbons, ozone, ultraviolet radiation, acidic rain), chemical (e.g., insecticides, fungicides, herbicides, heavy metals), nutritional stress (e.g., over- or under-abundance of fertilizer, micronutrients, macronutrients, particularly potassium, nitrogen derivatives, and phosphorus derivatives), and improved healing response to wounding. Use of peptides of the present invention imparts resistance to plants against such forms of environmental stress.

A further aspect of the present invention relates to the use of the peptides of the present invention as a safener in combination with one or more of the active agents (i.e., in a composition or in separate compositions) for the control of aquatic weeds in a body of water as described in U.S. Publ. No. 20150218099 to Mann, which is hereby incorporated by reference in its entirety.

Yet another aspect of the present invention relates to the use of the peptides of the present invention as a plant strengthener in a composition for application to plants grown under conditions of reduced water irrigation, which composition also includes at least one antioxidant and at least one radiation manager, and optionally at least one plant growth regulator, as described in U.S. Publ. No. 20130116119 to Rees et al., which is hereby incorporated by reference in its entirety.

The methods of the present invention involving application of the peptide or composition can be carried out through a variety of procedures when all or part of the plant is treated, including leaves, stems, roots, propagules (e.g., cuttings), fruit, etc. This may (but need not) involve infiltration of the peptide into the plant. Suitable application methods include high or low pressure spraying, injection, and leaf abrasion proximate to when peptide application takes place. When treating plant seeds, in accordance with the application embodiment of the present invention, the hypersensitive response elicitor protein or polypeptide can be applied by low or high pressure spraying, coating, immersion (e.g., soaking), or injection. Other suitable application procedures can be envisioned by those skilled in the art provided they are able to effect contact of the hypersensitive response elicitor polypeptide or protein with cells of the plant or plant seed. Once treated with the peptides or compositions of the present invention, the seeds can be planted in natural or artificial soil and cultivated using conventional procedures to produce plants. After plants have been propagated from seeds treated in accordance with the present invention, the plants may be treated with one or more applications of the peptides or compositions of the invention to impart disease resistance to plants, to enhance plant growth, to control insects on the plants, to impart biotic or abiotic stress tolerance, to improve desiccation resistance of removed cuttings, to impart post-harvest disease resistance or desiccation resistance to harvested fruit or vegetables, and/or improved longevity of fruit or vegetable ripeness for harvested fruit or vegetables.

Where the peptides are applied in the form of a recombinant beneficial microbe, these microbes can be applied in the form of an aqueous solution comprising a suspension of such beneficial microbes, which is then applied to the plant by spraying, coating, or immersion as described above. When treating plant seeds, in accordance with the application embodiment of the present invention, the microbes can be applied by low or high pressure spraying, coating, immersion (e.g., soaking), or injection. Other suitable application procedures can be envisioned by those skilled in the art provided they are able to effect contact of the beneficial microbes with cells of the plant or plant seed. In accordance with the application embodiment of the present invention, the beneficial microbes can be applied to plants or plant seeds in dry form. By way of example, dry application of microbes can be accomplished using bacterial or fungal products such as Kodiak® HB, available from Chemtura, and T-22™ HC, available from BioWorks. Once treated with the microbes of the present invention, the seeds can be planted in natural or artificial soil and cultivated using conventional procedures to produce plants. After plants have been propagated from seeds treated in accordance with the present invention, the plants may be treated with one or more applications of the microbes of the invention or the peptides, fusion proteins, or compositions of the invention, to impart disease resistance to plants, to enhance plant growth, to control insects on the plants, to impart biotic or abiotic stress tolerance, to improve desiccation resistance of removed cuttings, to impart post-harvest disease resistance or desiccation resistance to harvested fruit or vegetables, and/or improved longevity of fruit or vegetable ripeness for harvested fruit or vegetables.

The peptides or compositions of the invention can be applied to plants or plant seeds in accordance with the present invention alone or in a mixture with other materials. Alternatively, the peptides or compositions can be applied separately to plants with other materials being applied at different times.

In the alternative embodiment of the present invention involving the use of transgenic plants and transgenic seeds, a peptide of the invention need not be applied topically to the plants or seeds. Instead, transgenic plants transformed with a DNA molecule encoding a peptide of the invention are produced according to procedures well known in the art. A vector suitable for expression in plants (i.e., containing translation and transcription control sequences operable in plants) can be microinjected directly into plant cells by use of micropipettes to transfer mechanically the recombinant DNA. Crossway, *Mol. Gen. Genetics,* 202:179-85 (1985), which is hereby incorporated by reference in its entirety. The genetic material may also be transferred into the plant cell using polyethylene glycol. Krens, et al., *Nature,* 296:72-74 (1982), which is hereby incorporated by reference in its entirety.

Another approach to transforming plant cells with a gene encoding the peptide of the invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859-63 (1982), which is hereby incorporated by reference in its entirety. The DNA molecule may also be introduced into the plant cells by electroporation. Fromm et al., *Proc. Natl. Acad. Sci. USA,* 82:5824 (1985), which is hereby incorporated by reference in its entirety. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C. *Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. J. Schell, *Science,* 237:1176-83 (1987), which is hereby incorporated by reference in its entirety.

After transformation, the transformed plant cells must be regenerated. Plant regeneration from cultured protoplasts is described in Evans et al., *Handbook of Plant Cell Cultures,* Vol. 1: (MacMillan Publishing Co., New York, 1983); and Nasil I. R. (ed.), *Cell Culture and Somatic Cell Genetics of Plants,* Acad. Press, Orlando, Vol. 1, 1984, and Vol. Ill (1986), which are hereby incorporated by reference in their entirety.

It is known that practically all plants can be regenerated from cultured cells or tissues. Means for regeneration varies from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, control of insects on the plant, abiotic or biotic stress tolerance, improved desiccation resistance of removed cuttings, post-harvest disease resistance or desiccation resistance in harvested fruit or vegetables, and/or improved longevity of fruit or vegetable ripeness for harvested fruit or vegetables.

Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, to control insects, to impart abiotic or biotic stress tolerance, to improve desiccation resistance of removed cuttings, to impart post-harvest disease resistance or desiccation resistance in harvested fruit or vegetables, and/or to impart improved longevity of fruit or vegetable ripeness for harvested fruit or vegetables.

When transgenic plants and plant seeds are used in accordance with the present invention, they additionally can be treated with the same materials as are used to treat the plants and seeds to which a peptide of the invention or composition of the invention is applied. These other materials, including peptides or composition of the invention, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the peptides or compositions of the invention to impart disease resistance, enhance growth, control insects, abiotic or biotic stress tolerance, desiccation resistance of removed cuttings, post-harvest disease resistance or desiccation resistance in harvested fruit or vegetables, and/or improved longevity of fruit or vegetable ripeness for harvested fruit or vegetables.

Such transgenic plants may also be treated with conventional plant treatment agents, e.g., bacteriocidal or biocidal agents, protease inhibitors, non-ionic surfactants, fertilizers, herbicides, insecticides, fungicides, nematicides, biological inoculants, plant regulators, and mixtures thereof, as described above.

Examples

The following examples are provided to illustrate embodiments of the present invention but are by no means intended to limit its scope.

Example 1—Determination of a Minimal HR-Eliciting Sequence

The minimal eliciting sequence derived from was developed based on the sequence of the hrex gene from *Xanthomonas campestris* pv. *pelargonii*. A number of truncated and mutated sequences were synthesized and tested for Hypersensitive Response induction (results in Table 4). HR in tobacco was tested as described in Wei, *Science* 257:85-88 (1992), which is hereby incorporated by reference in its entirety. Briefly, peptides were dissolved at a concentration of 500 μg/ml in aqueous solution. Four serial dilutions were performed with an equal volume of water, yielding peptide samples at 500, 250, 125, 62.5, 31.25 μg/ml peptide solutions. *Nicotiana tabacum* cultivar xanthi plants were used at 5-7 weeks old (preflowering). Leaves were lightly punctured with a toothpick in a middle leaf panel. Peptide solutions were then infused via needle-less syringe into the wound, filling the panel. Each peptide sample was infused into a leaf of 2 different plants. The leaves were observed and scored over the next 48 hours for withering and browning, lesions typical of programmed cell death. These studies had three main goals: (1) determine the minimal sequence sufficient for HR elicitation (2) increase the solution stability of the peptides; (3) make disruptive mutations to verify the residues which are most important for HR elicitation; (4) make conservative mutations to identify the degree of specificity for particular amino acids.

The wild-type sequence from *Xanthomonas campestris* pv. *pelargonii* contains several methionine residues, which are prone to oxidation. Mutant peptides (P5-2, and P5-3) contain Met to Ala mutations, but these mutations do not affect the elicitation of HR, suggesting that the methionine residues are dispensable for HR activation.

Based on the P5 and P5a sequences (SEQ ID NOS: 8 and 9), disruptive or conservative single mutations were introduced at specific residues within the sequence. In the case of Leucine residues, these were mutated to glutamic acid (disruptive due to the introduction of a negative charge) or valine (conservative). The intervening sequences, depending on the identity of the amino acid in question, were mutated to have a negative charge (aspartic acid or glutamic acid), have a hydrophobic sidechain (valine), a minimal sidechain (alanine), or a small polar sidechain (serine). These mutant peptides were tested for elicitation of the hypersensitive response. Additional mutations are chosen based on the initial HR results. For those amino acids that were important for HR elicitation, more conservative mutations were chosen to determine the specificity of interactions. The leucine residues were mutated to isoleucine, valine, phenylalanine or tyrosine, with the latter 2 residues being less conservative. As above, these mutants were tested for HR elicitation.

TABLE 4

| Peptide name | Sequence | SEQ ID NO: | HR: |
|---|---|---|---|
| P5 | SAGSEQQLDLLLMFIMMMLQQ | 8 | + |
| P5a | SAGSEQQLDQLLLMFIMMMLQQ | 9 | + |
| P5-2 | SAGSEQQLDLLLMFIAAALQQ | 10 | + |
| P5-3 | SAGSEQQLDLLLAFIAAALQQ | 11 | + |
| P5-4 | SAGSEQQLELLLAFIAAALQQ | 12 | + |
| P5-5 | QLELLLAFIAAALQQ | 139 | + |
| P5-6 | SAGSEQQLDLLLAFIAAAL | 140 | - |
| P5-7 | SEEEEELDLLLAFIAAAL | 13 | - |
| P5-8 | SEEEEELDLLLAFIAAALQQ | 14 | Weak+ |
| P5-9 | LDLLLAFIAAALEEEEEE | 15 | - |
| P5-10 | LDLLLAFIEEELEEEE | 16 | - |
| P5-11 | SEEELDLLLAFIAAALEE | 17 | - |
| P5-12 | SEEELDLLLAFIEEELEE | 18 | - |
| P5-13 | SEEELDLLLAFIAAALDD | 19 | - |
| P5-14 | SEEEEELDLLLAFIAAALGG | 20 | Weak+ |
| P5-15 | SEEEEELDLLLAFIAAALQ | 25 | - |
| P5-16 | SEEEEELDLLLAFIAAALS | 26 | - |
| P5-17 | SEEEEELDLLLAFIAAALA | 27 | - |
| P5-18 | SEEEEELDLLLAFIAAALE | 28 | - |
| P5-19 | SELELLLAFIAAALEEEEE | 29 | + |
| P5-20 | SELELLLEFIEEELEE | 36 | - |
| P5-21 | SEEQLELLLAFIAAALQQEE | 33 | + |
| P5-22 | SEEELELLLAFIAAALEEEE | 30 | + |
| P5-23 | SEEEEELDQLLLAFIAAALQQ | 50 | Weak+ |
| P5-24 | SEEEEELDQLLLAFIAAAL | 51 | - |
| P5-25 | SEEEQLDQLLLAFIAAALQQ | 52 | - |
| P5-26 | SEEQLDLLLAFIAAALQEE | 34 | + |
| P5-27 | SEEQLDQLLLAFIAAALQEE | 53 | - |
| P5-28 | SEEQLDQLLLAFIAAALEE | 54 | Weak+ |
| P5-29 | SEEELDLLLMFIMMMLEE | 42 | + |
| P5-30 | SEEELDQLLLMFIMMMLEE | 55 | + |
| P5-31 | SEEEQLDLLLMFIMMMLEE | 43 | + |
| P5-32 | SEEEQLDQLLLMFIMMMLEE | 56 | + |
| P5-33 | SEEEQLDLLLMFIMMMLQEE | 44 | + |
| P5-34 | SEEEQLDQLLLMFIMMMLQEE | 57 | + |
| P5-35 | SAGSEQQEDLLLMFIMMMLQQ | 71 | Weak+ |
| P5-36 | SAGSEQQLDELLMFIMMMLQQ | 72 | + |
| P5-37 | SAGSEQQLDLELMFIMMMLQQ | 73 | - |
| P5-38 | SAGSEQQLDLLEMFIMMMLQQ | 74 | - |
| P5-39 | SAGSEQQLDLLLEFIMMMLQQ | 75 | Strong+ |
| P5-40 | SAGSEQQLDLLLMEIMMMLQQ | 76 | Strong+ |
| P5-41 | SAGSEQQLDLLLMFEMMMLQQ | 77 | - |
| P5-42 | SAGSEQQLDLLLMFIEMMLQQ | 78 | Weak+ |
| P5-43 | SAGSEQQLDLLLMFIMEMLQQ | 79 | Strong+ |
| P5-44 | SAGSEQQLDLLLMFIMMELQQ | 80 | Weak+ |
| P5-45 | SAGSEQQLDLLLMFIMMMEQQ | 81 | - |
| P5-46 | SEEQLDQLLLMFIMMMLQQEE | 58 | + |
| P5-47 | SEEQLDLLLMFIMMMLQQEE | 45 | + |
| P5-48 | SEEQLDLLLEFIEEELQQEE | 39 | - |
| P5-49 | SAGSEQQEDLLLAFIAAALQQ | 510 | - |
| P5-50 | SAGSEQQLDELLAFIAAALQQ | 511 | Weak+ |
| P5-51 | SAGSEQQEDELLAFIAAALQQ | 512 | - |
| P5-52 | SAGSEQQEDELLMFIMMMLQQ | 513 | - |
| P5-53 | SAGSEQQEDQLLLMFIMMMLQQ | 98 | - |
| P5-54 | SAGSEQQLDQELLMFIMMMLQQ | 99 | - |
| P5-55 | SAGSEQQLDQLLLAFIAAALQQ | 130 | - |
| P5-56 | SEEQEELLAFIAAALQQEE | 514 | - |
| P5-57 | SEEQLEELLAFIAAALQQEE | 515 | + |

TABLE 4-continued

| Peptide name | Sequence | SEQ ID NO: | HR: |
|---|---|---|---|
| P5-58 | SEEQEEELLAFIAAALQQEE | 516 | - |
| P5-61 | SAGSEQQEDLLLAFIALQQ | 519 | - |
| P5-62 | SAGSEQQLDELLAFIALQQ | 520 | - |
| P5-63 | SAGSEQQLDLLLEFIALQQ | 521 | - |
| P5-64 | SAGSEQQLDLLLAEIALQQ | 522 | - |
| P5-65 | SAGSEQQLDLLLAFIEALQQ | 523 | - |
| P5-66 | SAGSEQQLDLLLAFIAEALQQ | 524 | Weak+ |
| P5-67 | SAGSEQQLDLLLAFIEAALQQ | 525 | - |
| P5-68 | SAGSEQQLDLLLAFIAAELQQ | 526 | - |
| P5-69 | SAGSEQQLDLLLAEIAAALQQ | 527 | - |
| P5-70 | SAGSEQQLDLLLEFIAAALQQ | 528 | - |
| P5-71 | SAGSEQQEDLLLAFIAAALQQ | 529 | - |
| P5-72 | SAGSEQQLDELLAFIAAALQQ | 530 | - |
| P5-73 | SQAGSEQLDLLLMFIMMMLQQ | 531 | + |
| P5-74 | AEQGSSQLDLLLMFIMMMLQQ | 532 | + |
| P5-75 | NQGISEKQQLDLLLMFIMMMLQQ | 533 | Strong+ |
| P5-76 | NQGISEKQQLDLLLAFIAAALQQ | 534 | Weak+ |
| P5-77 | NFGTPDSTVQNPQDASKPNQLDLLLMFIMMMLQQ | 535 | Weak+ |
| P5-78 | NFGTPDSTVQNPQDASKPNQLDLLAFIAAALQQ | 536 | Weak+ |
| P5-79 | ITPDGQGGGQIGDNPQLDLLLMFIMMMLQQ | 537 | Strong+ |
| P5-80 | ITPDGQGGGQIGDNPQLDLLLAFIAAALQQ | 538 | Weak+ |
| P5-87 | SEEQLDLLLAFIAAALQQEE | 539 | - |
| P5-88 | SEEQLELLLAFIAAALQEE | 540 | + |

Example 2—Stability Tests of Variant Peptides

Peptides were assessed for one or more of solubility, stability against chemical degradation, effect of bulking agents on solution stability, oxidation protection and solution stability studies.

Stability against chemical degradation was assessed in various pH buffers by creating 0.2% AI solutions of pure, chemically synthesized peptide in deionized water, 0.25% weight to volume of Proxel® GXL (biocide), and 50 millimolar (mM) of nine buffers (separately) as follows: Citrate, pH 5.6, MES pH 6.0, MOPS pH 6.5, Citrate pH 7.2, EDDS pH 7.3, imidazole pH 7.5, EDTA pH 8, Phosphate pH 8, and TES pH 8. The solutions were observed on HPLC for evidence of degradation (% loss of the peptide signal over time, relative to the time 0 sample) over a period of weeks at elevated temperature (50° C.). Precipitation of P5 and P5-5 was noted in several samples, particularly those with pH<7. Other peptides, notably P5-9 and P5-21 remained in solution. These correlate with the lower hydrophobicity values for P5-9.

Figure 2:
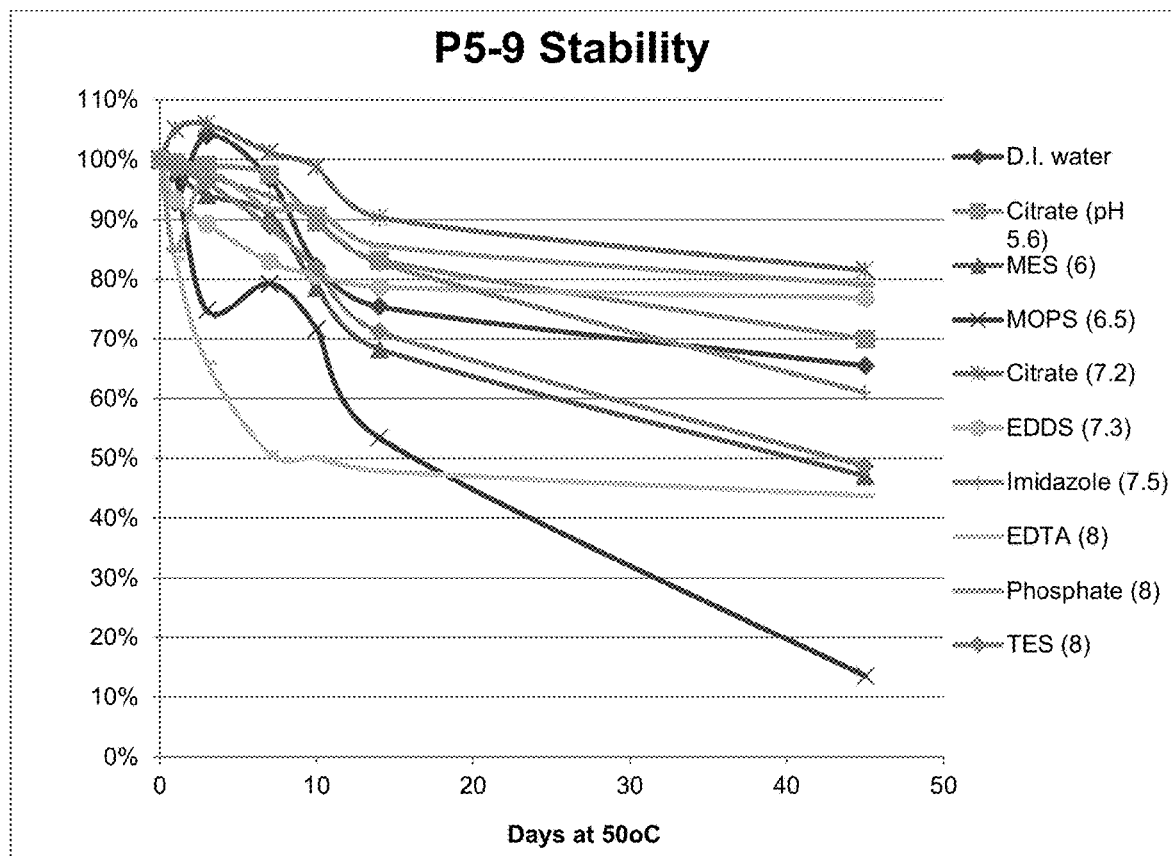
FIG. 2 shows a solubility and stability test of peptide P5-9 (SEQ ID NO: 15) in deionized water and the following 50 mM buffer solutions: citrate, pH 5.6; MES, pH 6.0; MOPS, pH 6.5; citrate, pH 7.2; EDDS, pH 7.3; imidazole, pH 7.5; EDTA, pH 8; sodium phosphate, pH 8.0; and TES, pH 8.0. Peptide P5-9 exhibited better solubility performance at 500 ug/ml as well as better stability compared with P5. In both citrate at pH 7.2 and phosphate at pH 8.0, peptide P5-9 exhibited around 80% remaining after 45 days.

Peptide P5 exhibited poor solubility below pH 7.0, which distorted the experimental results (not shown). For the buffer solutions above pH 7.0, generally poor stability was observed, with the best results in an EDTA buffer at pH 8.0 (about 40% remaining after 14 days (FIG. 1). P5-9 contains a C-terminal glutamate sequence for solubility enhancement and mutations of methionine residues for increased resistance to oxidation. This peptide exhibited better solubility performance at 500 ug/ml as well as better stability compared with P5 (FIG. 2). Citrate at pH 7.2 and Phosphate at pH 8.0 exhibited above 80% remaining after 14 days. Notably, after 45 days, 81% of the original peptide remained for the citrate pH 7.2 sample and 79% for the phosphate pH 8.0.

Figure 3:
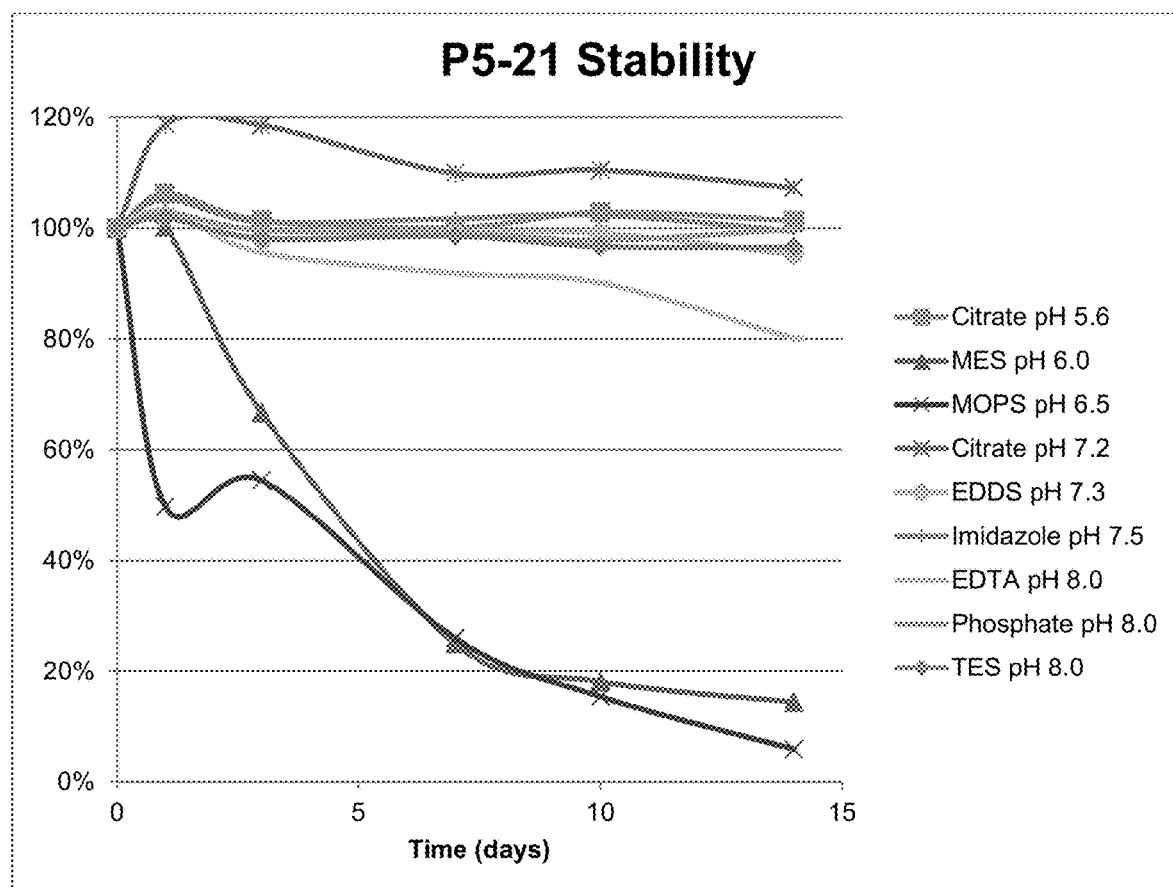
FIG. 3 shows a solubility and stability test of peptide P5-21 (SEQ ID NO: 33) in the following 50 mM buffer solutions: citrate, pH 5.6; MES, pH 6.0; MOPS, pH 6.5; citrate, pH 7.2; EDDS, pH 7.3; imidazole, pH 7.5; EDTA, pH 8; sodium phosphate, pH 8.0; and TES, pH 8.0. Peptide P5-21 exhibited good solubility at pH 5.6 and higher, as well as excellent stability (>90% after 14 days) for all buffers pH >7.0 except EDTA (around 80%).

P5-21 is a minimal sequence necessary for HR elicitation containing both N- and C-terminal solubility enhancing sequences and methionine to alanine mutations. It exhibited good solubility at pH 5.6 and higher as well as excellent stability (>90%) for all buffers pH >7.0 except EDTA (around 80%). Results are shown in FIG. 3.

Samples of material P5, P5-21, and P5-25 bulked with maltodextrin and either phosphate buffer (pH 8.0) or citrate buffer (pH 7.2) were tested for stability at room temperature for 48 hours. No significant degradation (more than 5% loss) was observed.

Solution stability studies were carried out by creating 0.09% AI solutions of pure, chemically synthesized peptide in deionized water, 50 mM of pH buffer, 0.25% Proxel GXL, and 0-50% isopropanol. Peptides solutions were analyzed by HPLC for % loss of the peptide signal over time during incubation at 50° C., relative to the time 0 sample. Peptides were analyzed until the remaining peptide concentration decreased to 80% of original (20% degradation). Results are summarized in Table 5 below.

TABLE 5

Formulation Stability of P5 Variants

| Peptide | SEQ ID NO: | Formulation: | Time before 20% degradation (days) |
|---|---|---|---|
| P5 | 8 | 50 mM phosphate pH 8.0 30% IPA 5 mM DTPA | 21 |
| P5-21 | 33 | 50 mM citrate pH 7.2 20% IPA | 41 |
| P5-25 | 52 | 50 mM citrate pH 7.2 | 53 |
| P5-27 | 53 | 50 mM imidazole pH 7.5 50% IPA | 50 |

IPA: isopropanol,
DTPA: diethylenetriaminepentaacetic acid

Example 3—Induction of Resistance to Tobacco Mosaic Virus

Peptides were tested for the induction of resistance to tobacco mosaic virus (TMV) in tobacco. Briefly, three tobacco plants at 6-8 weeks old were selected per group (samples and controls). The bottom-most leaf of the plant was covered and the plant was sprayed with a solution of water (untreated control—UTC), peptide, or Proact (positive control). The spray was applied until the leaves were fully wetted, indicated by liquid dripping from the leaves. The plants were then allowed to dry and the leaf covering was removed.

Three days post-treatment, the previously-covered leaf and a leaf on the opposite side of the plant were then lightly dusted with diatomaceous earth and 20 ul of a 1.7 ug/ml solution of purified tobacco mosaic virus was applied. The TMV solution was then spread across the leaf surface by lightly rubbing solution and the diatomaceous earth across the surface of the leaves. Two minutes after inoculation, the diatomaceous earth was rinsed off the leaves with water. 3 days after TMV inoculation, the leaves were scored based on the number of TMV lesions observed. The leaf was also scored for signs of the hypersensitive response, including yellowing and wilting of the affected leaves.

Effectiveness described in Table 6 refers to the % decline in TMV lesions on treated vs UTC plants. A reduction of TMV on covered leaves indicates a systemic immune response in the plant while reduction on uncovered leaves indicates a local response. Asterisks indicate that the P-value derived from a T-test was <0.05.

TABLE 6

Summary of TMV Resistance

| Peptide | SEQ ID NO: | Concentration (ug/ml) | Effectiveness Uncovered (%) | Effectiveness Covered (%) |
|---|---|---|---|---|
| P5 | 8 | 10 | 68* | 50 |
| P5-2 | 10 | 20 | 25 | 90* |
| P5-3 | 11 | 20 | 55 | 70* |
| P5-4 | 12 | 20 | 97* | 98* |
| P5-5 | 139 | 20 | 84* | 97* |
| P5-6 | 140 | 20 | 62 | 36 |
| P5-7 | 13 | 20 | 71 | 91* |
| P5-8 | 14 | 20 | 99* | 99* |
| P5-21 | 33 | 20 | 94* | 81* |
| P5-22 | 30 | 20 | 82 | 62 |
| P5-25 | 52 | 20 | 91* | 93* |
| P5-46 | 58 | 20 | 85* | 74* |
| P5-47 | 45 | 20 | 87* | 78* |

Example 4—Induction of Nematode Resistance in Soy Plants

The effectiveness of peptide treatment in suppressing the growth of soybean cyst nematodes (SCN) was assessed in soy. Soy was planted in a 1:1 sand/Turface mixture in a greenhouse (temperature held at 28° C.), with 10 plants per treatment group. 14 days after planting, plants were sprayed with a 2.0 µg/ml solution of peptide or a control solution without peptide. 4,000 freshly harvested SCN eggs were added to the plants 48 hours after peptide application. 30 days after pathogen introduction, the plants were harvested and the cysts were collected and counted using an elutriator.

In two separate trials, application of P5 (SEQ ID NO: 8) at 2.0 ug/ml caused a significant reduction in SCN populations. In trial #1, the control population contained an average of 133.5 cysts per plant compared with an average of 69.7 cysts per plant for the P5 treatment group (P=0.004). In trial #2, the control population contained an average of 104.9 cysts per plant compared with an average of 54.5 cysts per plant for the P5 treatment group (P=0.019). These results suggest that the peptides of the current invention strongly activate soy plant defenses against nematode infiltration.

Additional experiments will be performed to examine the effectiveness of peptide treatment in suppressing the growth of soybean cyst nematodes using one or more of the other peptides in Tables 1 and 2, including, without limitation, P5-21 and P5-25. See Example 8 below.

Example 5—Drought Resistance in Corn

The effectiveness of peptide treatment in reducing drought stress was assessed in corn and soy. 3.5 inch pots were filled with Sunshine #1 soil (SunGro Horticulture), fertilized with a 20-10-20 mixture. The soil was soaked and drained overnight. Seeds (either corn or soy, manually inspected to ensure uniform seed size) were planted at a depth of 1 inch for germination. Plants were grown in a greenhouse under 16 hour light days at >70° F. and 8 hour dark nights at >65° F. Prior to drought conditions, the plants were well-watered.

When the plants reached the V1 stage, plants were culled to achieve a uniform height (abnormally large and small plants were removed). Plants were then randomly assigned to control (spray without peptide) or treatment (spray with peptide) groups and heights were measured. Peptide was made up in a solution of 0.2 ug/ml or 2 ug/ml in distilled water+0.01% Tween-20, and applied as a fine mist from a spray bottle until the solution drips from the leaves. After the peptide solutions were dried, the plants were again randomized in a randomized complete block design. Drought stress was initiated after the peptide treatment. This was caused by maintaining the water level at 25-50% of the maximum capacity for water (capacity was decided as the weight of the pot filled with saturated soil minus the weight of the filled pot prior to adding water).

The drought test phase ended after 2-3 weeks. At that time, the plant height was again measured and the growth rate was calculated as the difference between this and the previously-recorded height. The above-ground part portions of the plants were harvested and weighed. The above-ground portion was also dried in an oven at 70° C. for 72 hours and a dry weight was obtained. All calculations were compared with matched untreated control plants.

The drought testing procedure was carried out in corn using a treatment of P5 (SEQ ID NO: 8). Treatment with 2.0 ug/ml of peptide caused a 3.09% increase in the growth rate, a 10.04% increase in the dry weight (P<0.05), and a 4.01% increase in fresh weight.

As shown in Table 7, additional peptides caused a drought resistance phenotype.

TABLE 7

Summary of Drought Resistance

| Peptide | SEQ ID NO: | Concentration (ug/ml) | Dry Weight Increase (%) | Fresh Weight Increase (%) |
|---|---|---|---|---|
| P5-46 | 58 | 2.0 | 3.71 | 9.05** |
| P5-76 | 534 | 0.2 | 5.33* | 2.00 |
| P5-35 | 71 | 2.0 | −6.57* | −6.05* |

*P < 0.1,
**P < 0.05

Experimental results for P5-21 and P5-25 were not statistically significant. One notable result is P5-35. Although this result is a negative phenotype under treatment, this shows that the peptide has some bioactivity. It has been shown previously with other harpin proteins that over-application can result in a negative response. Future experiments could show that lower concentration application of this peptide can cause a positive biological response. See Example 10 below.

Example 6—Root Knot Nematode (RKN) Resistance in Tomato

'Rutgers' tomato seedlings were transplanted into pasteurized sandy soil in 5 inch clay pots. The plants were spray-treated with a peptide solution until the leaves were saturated immediately after transplanting. 2 days after transplant, the plants were inoculated with root knot nematode (*Meloidogyne incognita*) eggs (5000 eggs per pot). Plants were maintained in a greenhouse for about 60 days post-inoculation, corresponding to 2 life cycles for the nematode. Two additional spray applications were made 21 and 42 days after transplanting.

For these trials, controls treatments included a commercial standard (Vydate) positive control; an untreated, RKN-inoculated control; and an untreated uninoculated control. At the end of each trial, the following measures were taken: root gall rating classification (based on % of roots with galling, 1—minimal: <5% roots with galls, 2—slight:5-25% roots with galls, 3—moderate: 26-50% roots with galls, 4—heavy: over 50% of roots with galls) and counting of the number of RKN eggs per gram of root.

For spray-treatment with P5 at 46.7 ug/ml, a significant reduction in root galling was observed (4 in untreated plants vs 2-3 in treated plants). Likewise, a reduction in egg counts was observed: an average of 165,600 for untreated plants vs 52,000 for treated plants, a 69% decrease, p=0.02.

Example 7—Drought Resistance in Soy

The effectiveness of peptide treatment in reducing drought stress was assessed in soy. 3.5 inch pots were filled with Sunshine #1 soil (SunGro Horticulture), fertilized with a 20-10-20 mixture. The soil was soaked and drained overnight. Seeds (soy, manually inspected to ensure uniform seed size) were planted at a depth of half inch for germination. Plants were grown in a greenhouse under 16 hour light days at >70° F. and 8 hour dark nights at >65° F. Prior to drought conditions, the plants were well-watered.

When the plants reached the growth stage when first trifoliate expanded, plants were culled to achieve a uniform height (abnormally large and small plants were removed). Plants were then randomly assigned to control (spray without peptide) or treatment (spray with peptide) groups and heights were measured. Peptide was made up in a solution of 0.2 ug/ml or 2 ug/ml in distilled water+0.04% Tween-20, and applied as a fine mist from a spray bottle until the solution drips from the leaves. After the peptide solutions were dried, the plants were again randomized in a randomized complete block design. Cyclic drought stress was initiated after the peptide treatment. Plants were subjected to at least three drought cycles of drought stress (3-5 days of withholding water and 1 day irrigated with saturating amount of water) before harvesting.

The drought test phase ended after 2-3 weeks. At that time, the plant height was again measured and the growth rate was calculated as the difference between this and the previously-recorded height. The above-ground part portions of the plants were harvested and weighed to obtain fresh weight. The above-ground portion was also dried in an oven at 70° C. for 72 hours to obtain dry weight. All calculations were compared with matched untreated control plants.

Results are shown in Table 8 below. Asterisks indicate statistical significance by P-value (*: P<0.1 and **: P<0.05).

TABLE 8

Summary of Drought Resistance

| Peptide | SEQ ID NO: | Concentration (ug/ml) | Dry Weight Increase (%) | Fresh Weight Increase (%) |
|---|---|---|---|---|
| P5-27 | 53 | 2.0 | 2.04 | 4.07* |
| P5-33 | 44 | 2.0 | 5.02** | 4.10 |

TABLE 8-continued

Summary of Drought Resistance

| Peptide | SEQ ID NO: | Concentration (ug/ml) | Dry Weight Increase (%) | Fresh Weight Increase (%) |
|---|---|---|---|---|
| P5-75 | 533 | 0.2 | 3.73 | 8.78** |
| P5-75 | 533 | 2.0 | 4.37 | 8.55** |

Example 8—Comparison of Peptides with Chemical Nematode Agents in Soy

The effectiveness of peptides was tested in soy (Sheyenne variety) and compared with current anti-nematode chemicals. Briefly, soy seeds were commercially coated with peptide at rates of 10, 30, or 90 ug peptide per seed or with chemical nematicides Avicta Complete, Clariva Complete, Poncho/Votivo, or Velum total. 3 soy seeds were planted in a mixture of topsoil and sand (pasteurized) in a 10 cm diameter pot and were inoculated with 1500 eggs per pot at planting. 10 replicate pots were used per experimental condition. After plants emerged from the soil, the plants were thinned to one plant per pot. Plants were harvested about 45 days after planting. The following measures were taken: (1) Fresh shoot and root weights; (2) Root condition graded 0-10 for the presence of disease; (3) Nematode cysts per plant; (4) Nematode eggs per plant; and optionally (5) Male nematodes. The following values were calculated: eggs per gram of root, cysts per gram of root, and eggs per cyst.

P5 (SEQID: 8) did not exhibit a significant reduction in cysts or eggs, but did cause a ~30% reduction in the number of male nematodes. However, the chemical treatments caused a greater reduction in the male nematodes.

P5-21 (SEQID: 33) caused a reduction in cysts per gram root: 91% at 10 ug, 80% at 30 ug, and 86% at 90 ug. These were numerically greater than the results for Clariva Complete (76%) and Avicta Complete (78%). The results were statistically significantly greater than those of Poncho/Votivo (58%). There was also a significant reduction in eggs per gram root: 93% for a bug treatment, 74% for a 30 ug treatment, 92% for a 90 ug treatment. These were numerically greater than those of Clariva Complete (75%) and Avicta Complete (72%) for all tested rates. The results for P5-21 at bug and 90 ug were statistically significantly greater than the results for Poncho/Votivo (49%).

P5-25 (SEQID: 52) also caused a strong reduction in cysts per gram of root: 92% at 10 ug, 82% at 30 ug, and 91% at 90 ug. These were numerically greater than the results for Clariva Complete (76%) and Avicta Complete (78%). The results at bug and 90 ug were statistically significantly greater than Poncho/Votivo (58%). Likewise, there was a significant reduction in the eggs per gram root: 94% at 10 ug, 85% at 30 ug, and 93% at 90 ug. These results were numerically better than Clariva Complete (75%) and Avicta Complete (72%). The results were also statistically significantly greater than those of Poncho/Votivo (49%).

Example 9—Stimulation by P5 of Anti-Nematode Root Secretions in Soy

Soybean seeds coated with P5 (SEQ ID NO: 8) or a mock treatment were wetted and germinated in brown paper for 48 hours. Seedlings were then placed in a beaker with 3 ml distilled water per seedling for 24 hours. The liquid exudate was then collected and 1 ml was added to each well of a 24-well plate. 300 soybean cyst nematode *Heterodera glycines* eggs were added into a plastic micro-sieve mesh and placed on each of the 24 wells. After incubating for 3 days, the number of hatched nematodes at the well bottom was counted. In the mock-treated exudate wells, counts revealed an average of 40 hatched nematodes. In the p5-treated exudate wells, an average of 30 hatched nematodes was counted. This was a statistically significant difference ($P<0.05$).

Example 10—Corn Drought Performance in the Field

Peptide P5 (SEQ ID: 8) was tested for its efficacy in reducing drought stress under field conditions. Briefly, a site was chosen in Hughson, Calif., where rainfall is minimal and irrigation is required for growing. Corn hybrid seeds 639STX (Heine Seed Company) were coated with P5 at 12, 35, or 105 ug peptide per seed or a mock treatment. The planting field was divided 3 row (30" spacing)×25 foot plots. Corn was planted at a rate of 32,000 viable seeds per acre (6.5 inches between seeds on 30 inch rows. Four border rows (10 ft) were planted on all sides of the trial to mitigate environmental effects. Each treatment group was replicated 4 times and arrayed in a Randomized Complete Block design.

Irrigation was managed in the following way: The site was initially irrigated to assure a good plant stand and early growth. Two drought periods were initiated. The first started at the V-3 plant growth stage and ended when leaf curling was visible in the plants. The second drought period started at tassel emergence and ended at the end of pollen shed. During both drought periods, the plants were monitored to avoid reaching a permanent wilting point.

Treatment with P5 resulted in an increase of 20.2 bushels per acre (Bu/Ac) for 12 ug/seed treatment, an increase of 11.4 Bu/Ac for 35 ug/seed treatment, and an increase of 19.7 Bu/Ac for a 105 ug/seed treatment rate. These results compared with an average yield of 123.6 Bu/Ac for untreated control. The growers also observed an increase in metrics associated with the size of the corn ear. The number of rows per corn ear increased from 12.3 (UTC) to 12.7 for 12 ug/seed, remained unchanged for 35 ug/seed, and increased to 13.1 for 105 ug/seed. The mass of the corn ears also increased from 90.1 grams per ear (UTC) to 104.8 g for 12 ug/seed, 98.4 g for 35 ug/seed, and 104.5 g for 105 ug/seed. The number of kernels per row was 25.9 for UTC. This increased to 28.6 for 12 ug/seed, decreased slightly to 25.3 for 35 ug/seed, and increased to 28.9 for 105 ug/seed. These results indicate a potent effect on water conservation in corn.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. An isolated peptide that is between 13 and 50 amino acids in length, the peptide comprising the amino acid sequence of:

(SEQ ID NO: 2)
L-X-X-L-L-L-X-(F/L)-(I/L)-X-X-X-L wherein

X at position 3 is optional and, when present, is selected from Asp (D), isoD, Glu (E), y-glutamate, Gln (Q), Asn (N), Ser (S), and Gly (G), and each X at positions 2, 7, 10, 11, and 12 is independently selected from Met (M), Ala (A), Asp (D), isoD, Glu (E), y-glutamate, Gln (Q), Asn (N), Ser (S), and Gly (G); or (ii)
(SEQ ID NO: 3)
(Q/E)-(Q/E)-(L/I/V/F)-X-X-(L/I/V/F)-(L/I/V/F)-

(L/I/V/F)-X-(L/I/V/F)-(L/I/V/F)-X-X-X-

(L/I/V/F)-(D/G/Q/E)-(D/G/Q/E), wherein

X at position 5 is optional and, when present, is selected from Asp (D), isoD, Glu (E), y-glutamate, Gln (Q), Asn (N), Ser (S), and Gly (G), and each X at positions 4, 9, 12, 13, and 14 is independently selected from Met (M), Ala (A), Asp(D), isoD, Glu (E), y-glutamate, Gln (Q), Asn (N), Ser (S), and Gly (G); or (iii)
(SEQ ID NO: 4)
(L/I/V/F)-X-X-(L/I/V/F)-(L/I/V/F)-(L/I/V/F)-X-

(L/I/V/F)-(L/I/V/F)-X-X-X-(L/I/V/F)-

(D/G/Q/E)-(D/G/Q/E), wherein

X at position 3 is optional and, when present, is selected from Asp (D), isoD, Glu (E), y-glutamate, Gln (Q), Asn (N), Ser (S), and Gly (G), and each X at positions 2, 7, 10, 11, and 12 is independently selected from Met (M), Ala (A), Asp (D), isoD, Glu (E), y-glutamate, Gln (Q), Asn (N), Ser (S), and Gly (G); or (iv)
(SEQ ID NO: 5)
(Q/E)-(Q/E)-(L/I/V/F)-X-X-(L/I/V/F)-(L/I/V/F)-

(L/I/V/F)-X-(L/I/V/F)-(L/I/V/F)-X-X-X-

(L/I/V/F), wherein

X at position 5 is optional and, when present, is selected from Asp (D), isoD, Glu (E), y-glutamate, Gln (Q), Asn (N), Ser (S), and Gly (G), and each X at positions 4, 9, 12, 13, and 14 is independently selected from Met (M), Ala (A), Asp (D), isoD, Glu (E), y-glutamate, Gln (Q), Asn (N), Ser (S), and Gly (G), wherein the peptide induces an active plant response, but does not induce a hypersensitive response, when applied to plant tissue, or wherein the peptide induces a hypersensitive plant response when applied to plant tissue.

2. The isolated peptide according to claim 1, wherein X at position 3 of SEQ ID NO: 2 or 4 is not present; or X at position 5 of SEQ ID NO: 3 or 5 is not present.

3. The isolated peptide according to claim 1, wherein X at position 3 of SEQ ID NO: 2 or 4 is present, and selected from D, isoD, E, y-glutamate, and Q; or wherein X at position 5 of SEQ ID NO: 3 or 5 is present, and selected from D, isoD, E, y-glutamate, and Q.

4. The isolated peptide according to claim 1, wherein X at position 2 of SEQ ID NO: 2 or 4 is selected from the group consisting of D, isoD, E, and y-glutamate; or X at position 4 of SEQ ID NO: 3 or 5 is selected from the group consisting of D, isoD, E, and y-glutamate.

5. The isolated peptide according to claim 1, wherein the peptide is free of cysteine and methionine.

6. The isolated peptide according to claim 1, wherein X at position 7 of SEQ ID NO: 2 or 4 is selected from the group consisting of A, M, G, S, or E; or X at position 9 of SEQ ID NO: 3 or 5 is selected from the group consisting of A, M, G, S, or E.

7. The isolated peptide according to claim 1, wherein each X at positions 10, 11, and 12 of SEQ ID NO: 2 or 4 is selected independently from the group consisting of M, A, G, S, and E; or each X at positions 12, 13, and 14 of SEQ ID NO: 3 or 5 is selected independently from the group consisting of M, A, G, S, and E.

8. The isolated peptide according to claim 1 further comprising a hydrophilic amino acid sequence at either the N-terminal or C-terminal end of SEQ ID NO: 2, 3, 4, or 5.

9. The isolated peptide according to claim 8, wherein the hydrophilic amino acid sequence comprises from two to ten hydrophilic amino acid residues.

10. The isolated peptide according to claim 1, wherein the peptide comprises the amino acid sequence of:

(i)
(SEQ ID NO: 3)
(Q/E)-(Q/E)-(L/I/V/F)-X-X-(L/I/V/F)-(L/I/V/F)-

(L/I/V/F)-X-(L/I/V/F)-(L/I/V/F)-X-X-X-

(L/I/V/F)-(D/G/Q/E)-(D/G/Q/E), wherein
X at position 5 is optional and, when present, is selected from D, isoD, E, y-glutamate, Q, N, S, and G, and
each X at positions 4, 9, 12, 13, and 14 is independently selected from M, A, D, isoD, E, y-glutamate, Q, N, S, and G; or (ii)
(SEQ ID NO: 4)
(L/I/V/F)-X-X-(L/I/V/F)-(L/I/V/F)-(L/I/V/F)-X-

(L/I/V/F)-(L/I/V/F)-X-X-X-(L/I/V/F)-(D/G/Q/E)-

(D/G/Q/E), wherein
X at position 3 is optional and, when present, is selected from D, isoD, E, y-glutamate, Q, N, S, and G, and
each X at positions 2, 7, 10, 11, and 12 is independently selected from M, A, D, isoD, E, y-glutamate, Q, N, S, and G; or (iii)
(SEQ ID NO: 5)
(Q/E)-(Q/E)-(L/I/V/F)-X-X-(L/I/V/F)-(L/I/V/F)-

(L/I/V/F)-X-(L/I/V/F)-(L/I/V/F)-X-X-X-

(L/I/V/F), wherein
X at position 5 is optional and, when present, is selected from D, isoD, E, y-glutamate, Q, N, S, and G, and
each X at positions 4, 9, 12, 13, and 14 is independently selected from M, A, D, isoD, E, y-glutamate, Q, N, S, and G.

11. The isolated peptide according to claim 10, wherein the peptide comprises the amino acid sequence of:

(i)
(SEQ ID NO: 3)
(Q/E)-(Q/E)-(L/I/V/F)-X-X-(L/I/V/F)-(L/I/V/F)-

(L/I/V/F)-X-(L/I/V/F)-(L/I/V/F)-X-X-X-(L/I/V/F)-

(D/G/Q/E)-(D/G/Q/E), wherein
X at position 5 is optional and, when present, is selected from D, isoD, E, y-glutamate, Q, N, S, and G, and
each X at positions 4, 9, 12, 13, and 14 is independently selected from M, A, D, isoD, E, y-glutamate, Q, N, S, and G; or (ii)
(SEQ ID NO: 5)
(Q/E)-(Q/E)-(L/I/V/F)-X-X-(L/I/V/F)-(L/I/V/F)-

(L/I/V/F)-X-(L/I/V/F)-(L/I/V/F)-X-X-X-(L/I/V/F), wherein
X at position 5 is optional and, when present, is selected from D, isoD, E, y-glutamate, Q, N, S, and G, and
each X at positions 4, 9, 12, 13, and 14 is independently selected from M, A, D, isoD, E, y-glutamate, Q, N, S, and G.

12. The isolated peptide according to claim 10, wherein the peptide comprises the amino acid sequence of:

(SEQ ID NO: 4)
(L/I/V/F)-X-X-(L/I/V/F)-(L/I/V/F)-(L/I/V/F)-X-

(L/I/V/F)-(L/I/V/F)-X-X-X-(L/I/V/F)-(D/G/Q/E)-

(D/G/Q/E), wherein
X at position 3 is optional and, when present, is selected from D, isoD, E, y-glutamate, Q, N, S, and G; and
each X at positions 2, 7, 10, 11, and 12 is independently selected from M, A, D, isoD, E, y-glutamate, Q, N, S, and G.

13. The isolated peptide according to claim 11, wherein the peptide consists essentially of the amino acid sequence of SEQ ID NO: 3 or SEQ ID NO: 5.

14. The isolated peptide according to claim 1, wherein the peptide comprises the amino acid sequence of one of SEQ ID NOS: 8-26, 28, 29, 31-33, 35-38, 40, 41, 46-48, 52, 62, 139, 545, or 546.

15. The isolated peptide according to claim 1, wherein the isolated peptide has an average Kyte-Doolittle hydropathy index of less than 0.7.

16. The isolated peptide according to claim 1, wherein the peptide induces an active plant response, but does not induce a hypersensitive response, when applied to plant tissue.

17. The isolated peptide according to claim 16, wherein the peptide comprises the amino acid sequence of one of SEQ ID NOS: 140, 13, 15-19, 25-28, 36, and 51-53.

18. The isolated peptide according to claim 1, wherein the peptide induces a hypersensitive response when applied to plant tissue.

19. The isolated peptide according to claim 18, wherein the peptide comprises the amino acid sequence of one of SEQ ID NOS: 8-12, 139, 14, 20, 29, 33, 30, 50, 34, 54, 42, 55, 43, 56, 44, and 57.

20. The isolated peptide according to claim 1, wherein the peptide is at least 90% pure.

21. The isolated peptide according to claim 1 wherein the peptide is a fusion polypeptide comprising a second amino acid sequence coupled via peptide bond to the amino acid sequence.

22. The isolated peptide according to claim 21, wherein the second amino acid sequence includes a purification tag.

23. The isolated peptide according to claim 22, wherein the second amino acid sequence further includes a cleavable linker sequence between the purification tag and the amino acid sequence.

24. The isolated peptide according to claim 21, wherein the peptide is a fusion polypeptide comprising a first amino acid sequence for said peptide linked to a second amino acid sequence for said peptide.

25. A fusion polypeptide comprising a plurality of amino acid sequences linked together in series, each of the plurality of amino acid sequences comprising the peptide according to claim 1.

26. A composition comprising one or more peptides according to claim 1, and a carrier.

27. The composition according to claim 26, wherein the composition is a clarified cell extract.

28. The composition according to claim 26 further comprising an additive selected from the group consisting of fertilizer, herbicide, insecticide, fungicide, nematicide, a bactericidal agent, a biological inoculant, a plant regulator, and mixtures thereof.

29. The composition according to claim 28, wherein the composition comprises:
one or more of peptides according to SEQ ID NOS: 8, 14, 33, 52, 53, 71, and 58; and either
(i) clothianidin, a combination of clothianidin and *Bacillus firmus*, imidicloprid, or a combination of imidicloprid and *Bacillus firmus*; or
(ii) thiamethoxam; a combination of thiamethoxam, mefenoxam, and fludioxynil; a combination of thiamethoxam, mefenoxam, fludioxynil and azoxystrobin; a combination of thiamethoxam and abamectin; a combination of thiamethoxam, abamectin, and a Pasteuria nematicide; or a combination of thiamethoxam, mefenoxam, fludioxynil, azoxystrobin, thiabendazole, and abamectin; or
(iii) a biological inoculant comprising a *Bradyrhizobium* spp., a *Bacillus* spp., and a combination thereof.

30. The composition according to claim 26, wherein the carrier is an aqueous carrier optionally further comprising one or more of a biocidal agent, a protease inhibitor, a non-ionic surfactant, or a combination thereof.

31. The composition according to claim 26, wherein the carrier is a solid carrier in particulate form.

32. The isolated peptide according to claim 1, wherein the peptide comprises the amino acid sequence of SEQ ID NO: 2.

33. The isolated peptide according to claim 32, wherein the amino acid at position 8 is F and the amino acid at position 9 is I.

34. The isolated peptide according to claim 32, wherein the peptide further comprises (Q/E)-(Q/E) residues immediately preceding SEQ ID NO: 2, (D/G/Q/E)-(D/G/Q/E) residues immediately following SEQ ID NO: 2, or both.

35. The isolated peptide according to claim 34, wherein the peptide contains up to 20 amino acids preceding SEQ ID NO: 2 and up to 5 amino acids following SEQ ID NO: 2.

36. The isolated peptide according to claim 32, wherein any Lys or Arg residues are changed to Glu and an Arg residue is introduced at the C-terminal end of said peptide.

37. An isolated peptide that is between 13 and 50 amino acids in length, the peptide comprising the amino acid sequence of:
(i) one of SEQ ID NOS: 8-26, 28, 29, 31-33, 35-38, 40, 41, 46-48, 52, 62, 139, 545, or 546; or
(ii) one of SEQ ID NOS: 8-26, 28, 29, 31-33, 35-38, 40, 41, 46-48, 52, 62, 139, 545, or 546 except that an Arg residue is introduced at the C-terminal end of said peptide.

38. The isolated peptide according to claim 37, wherein the peptide consists essentially of the amino acid sequence of:
(i) one of SEQ ID NOS: 8-26, 28, 29, 31-33, 35-38, 40, 41, 46-48, 52, 62, 139, 545, or 546; or
(ii) one of SEQ ID NOS: 8-26, 28, 29, 31-33, 35-38, 40, 41, 46-48, 52, 62, 139, 545, or 546 except that an Arg residue is introduced at the C-terminal end of said peptide.

39. The isolated peptide according to claim 38, wherein the peptide consists essentially of the amino acid sequence of SEQ ID NO: 33 or SEQ ID NO: 518.

40. A method of imparting disease resistance to plants comprising:
applying an effective amount of an isolated peptide according to claim 1 to a plant or plant seed or the locus where the plant is growing or is expected to grow, wherein said applying is effective to impart disease resistance.

41. A method of enhancing plant growth comprising:
applying an effective amount of an isolated peptide according to claim 1 to a plant or plant seed or the locus where the plant is growing or is expected to grow, wherein said applying is effective to enhance plant growth.

42. A method of increasing a plant's tolerance to biotic stress comprising:
applying an effective amount of an isolated peptide according to claim 1 to a plant or plant seed or the locus where the plant is growing or is expected to grow, wherein said applying is effective to increase the plant's tolerance to biotic stress factors selected from the group consisting of insects, arachnids, nematodes, weeds, and combinations thereof.

43. A method of increasing a plant's tolerance to abiotic stress comprising:
applying an effective amount of an isolated peptide according to claim 1 to a plant or plant seed or the locus where the plant is growing or is expected to grow, wherein said applying is effective to increase the plant's tolerance to abiotic stress factors selected from the group consisting of salt stress, water stress, ozone stress, heavy metal stress, cold stress, heat stress, nutritional stress, and combinations thereof.

* * * * *